US010173217B2

(12) United States Patent
Yamawaki et al.

(10) Patent No.: US 10,173,217 B2
(45) Date of Patent: Jan. 8, 2019

(54) SAMPLE PROCESSING METHOD, SAMPLE PROCESSING CHIP, AND SAMPLE PROCESSING APPARATUS

(71) Applicant: Sysmex Corporation, Kobe-shi, Hyogo (JP)

(72) Inventors: Koya Yamawaki, Kobe (JP); Ayato Tagawa, Kobe (JP); Tsuyoshi Nakano, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 118 days.

(21) Appl. No.: 15/454,397

(22) Filed: Mar. 9, 2017

(65) Prior Publication Data
US 2017/0259266 A1    Sep. 14, 2017

(30) Foreign Application Priority Data

Mar. 10, 2016  (JP) ................. 2016-046915

(51) Int. Cl.
*G01N 1/31* (2006.01)
*G01N 1/38* (2006.01)
(Continued)

(52) U.S. Cl.
CPC ...... *B01L 3/502784* (2013.01); *B01F 3/0807* (2013.01); *B01F 5/0647* (2013.01);
(Continued)

(58) Field of Classification Search
CPC .............. B01F 13/0062; B01F 13/0079; B01F 13/0081; B01F 3/0807; B01F 5/0647;
(Continued)

(56) References Cited

U.S. PATENT DOCUMENTS 6,517,234 B1    2/2003  Kopf-Sill et al.
2009/0129198 A1*  5/2009  Karaki ............... B01F 13/0079
                                                        366/145
(Continued)

FOREIGN PATENT DOCUMENTS

JP     2009-100761 A     5/2009
WO    WO 2014/039587 A1   3/2014

OTHER PUBLICATIONS

Kim, S. et al., "Temperature-Programmed Natural Convection for Micromixing and Biochemical Reaction in a Single Microfluidic Chamber", *Analytical Chemistry*, vol. 81, No. 11, Jun. 1, 2009, pp. 4510-4516.
(Continued)

*Primary Examiner* — Jennifer Wecker
(74) *Attorney, Agent, or Firm* — Brinks Gilson & Lione

(57) ABSTRACT

Disclosed is a sample processing method for processing a target component in a sample by use of a sample processing chip having a storage portion and a droplet forming flow path, the sample processing method including: storing, in the storage portion, a mixture of the target component and a predetermined amount of a diluent for causing the target component to be encapsulated by one molecule or by one particle into a droplet; heating the mixture in the storage portion to cause thermal convection in the storage portion thereby to mix the target component and the diluent together; and in the droplet forming flow path, forming droplets in a dispersion medium, each droplet containing the diluted target component and a reagent that reacts with the target component.

20 Claims, 24 Drawing Sheets

(51) Int. Cl.
- *G01N 1/44* (2006.01)
- *B01L 7/00* (2006.01)
- *B01L 3/00* (2006.01)
- *B01F 13/00* (2006.01)
- *B01F 5/06* (2006.01)
- *B01F 3/08* (2006.01)
- *B01F 5/00* (2006.01)

(52) U.S. Cl.
CPC ...... *B01F 13/0062* (2013.01); *B01F 13/0079* (2013.01); *B01F 13/0081* (2013.01); *B01L 7/00* (2013.01); *G01N 1/31* (2013.01); *G01N 1/38* (2013.01); *G01N 1/44* (2013.01); *B01L 2200/16* (2013.01); *B01L 2300/0663* (2013.01); *B01L 2300/087* (2013.01); *B01L 2300/0816* (2013.01); *B01L 2300/0867* (2013.01); *B01L 2300/0877* (2013.01); *B01L 2300/0883* (2013.01); *B01L 2300/0887* (2013.01); *B01L 2300/18* (2013.01); *B01L 2300/185* (2013.01); *B01L 2400/0445* (2013.01); *B01L 2400/0487* (2013.01)

(58) Field of Classification Search
CPC ......... B01L 2200/16; B01L 2300/0663; B01L 2300/0816; B01L 2300/0867; B01L 2300/087; B01L 2300/0877; B01L 2300/0883; B01L 2300/0887; B01L 2300/18; B01L 2300/185; B01L 2400/0445; B01L 2400/0487; B01L 3/502784; B01L 7/00; G01N 1/38; G01N 1/44

See application file for complete search history.

(56) References Cited

U.S. PATENT DOCUMENTS

| | | | |
|---|---|---|---|
| 2011/0092373 | A1 | 4/2011 | Colston et al. |
| 2014/0134623 | A1* | 5/2014 | Hiddessen ............... G01N 1/38 435/6.12 |
| 2017/0327867 | A1* | 11/2017 | Dohale ................. C12Q 1/686 |

OTHER PUBLICATIONS

Konry, T. et al., "Live Single Cell Functional Phenotyping in Droplet Nano-Liter Reactors", *Scientific Reports*, vol. 3, No. 1, 2013, 5 pages.

* cited by examiner

Depth of storage portion 173: about 540 μm

Example 1

Example 2

SAMPLE PROCESSING METHOD, SAMPLE PROCESSING CHIP, AND SAMPLE PROCESSING APPARATUS

CROSS REFERENCE TO RELATED APPLICATIONS

This application claims priority from prior Japanese Patent Application No. 2016-046915, filed on Mar. 10, 2016, entitled "SAMPLE PROCESSING METHOD, SAMPLE PROCESSING CHIP, AND SAMPLE PROCESSING APPARATUS", the entire content of which is incorporated herein by reference.

FIELD OF THE INVENTION

There are technologies for mixing a plurality of components together by use of a sample processing chip (for example, see U.S. Pat. No. 6,517,234).

BACKGROUND

U.S. Pat. No. 6,517,234 mentioned above discloses a technology for infusing a plurality of components into a liquid sending channel of a sample processing chip and mixing the plurality of components together in the liquid sending channel. The plurality of components is mixed together while being conveyed in a flow path called a liquid sending channel.

Such a technology for mixing a plurality of components together by use of a sample processing chip is used for mixing a target component to be processed and a diluent together in order to dilute the target component, for example. In recent years, there are demands for a technology for detecting the target component by one molecule or by one particle in a sample (hereinafter, referred to as "digital detection"). The target component is a nucleic acid, a protein, a cell, or the like, for example. In the digital detection, the target component is caused to be encapsulated by one molecule or by one particle into one droplet, for example. Since the target component is put by one molecule or by one particle into each of unit regions which are respectively composed of individual droplets, this technique is referred to as "partitioning" the target component by one molecule or by one particle. In order to partition the target component by one molecule or by one particle, it is required to dilute the target component with a dilute at a high dilution rate.

SUMMARY OF THE INVENTION

The scope of the present invention is defined solely by the appended claims, and is not affected to any degree by the statements within this summary.

In U.S. Pat. No. 6,517,234, a plurality of components are mixed together while being conveyed in a flow path. Thus, in order to sufficiently uniformly mix the plurality of components, the flow path structure and the conveyance control for the components or liquids to be mixed are complicated. Therefore, in order to perform a process for executing digital detection by use of a sample processing chip, it is desired to mix the target component and the diluent, without making complicated the flow path structure and the conveyance control for the target component and the diluent.

A sample processing method according to a first aspect of the present invention is a sample processing method for processing a target component in a sample by use of a sample processing chip having a storage portion and a droplet forming flow path, the sample processing method including: storing, in the storage portion, a mixture of the target component and a predetermined amount of a diluent for causing the target component to be encapsulated by one molecule or by one particle into a droplet; heating the mixture in the storage portion to cause thermal convection in the storage portion thereby to mix the target component and the diluent together; and in the droplet forming flow path, forming droplets in a dispersion medium, each droplet containing the diluted target component and a reagent that reacts with the target component.

A sample processing chip according to a second aspect of the present invention is a sample processing chip to be set in a sample processing apparatus and configured to process a target component in a sample supplied by the sample processing apparatus, the sample processing chip including: a dilution flow path including a storage portion in which to store a mixture of the target component and a predetermined amount of a diluent for causing the target component to be encapsulated by one molecule or by one particle into a droplet, the dilution flow path configured to mix the target component and the diluent together by causing thermal convection in the storage portion by heat generated by a heating portion disposed in the sample processing apparatus; and a droplet forming flow path configured to form droplets in a dispersion medium, each droplet containing the target component diluted in the dilution flow path and a reagent that reacts with the target component.

A sample processing apparatus according to a third aspect of the present invention is a sample processing apparatus configured to process a target component in a sample by use of the sample processing chip according to the second aspect, the sample processing apparatus including: a setting portion in which to set the sample processing chip; a liquid sending portion configured to supply to the sample processing chip a liquid containing the target component and a diluent for diluting the target component, and transfer the liquid and the diluent; and a heating portion configured to heat a mixture of the diluent and the target component supplied to the storage portion in the sample processing chip, to cause thermal convection in the storage portion.

DETAILED DESCRIPTION OF THE PREFERRED EMBODIMENTS

Hereinafter, embodiments will be described with reference to the drawings.

[Overview of Sample Processing Chip]

Figure 1:
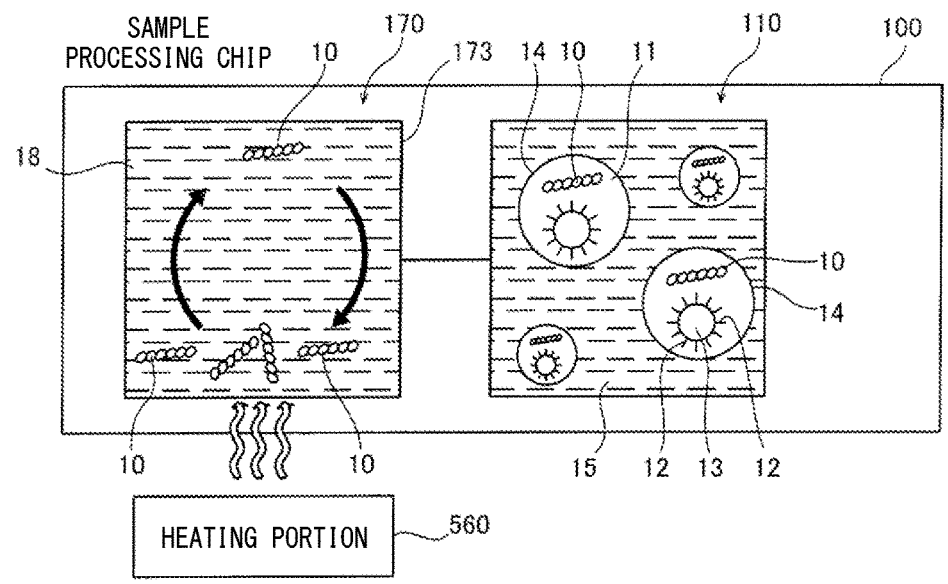
FIG. 1 is a diagram for explaining overview of a sample processing chip.

With reference to FIG. 1, overview of a sample processing chip according to the present embodiment will be described.

Figure 2:
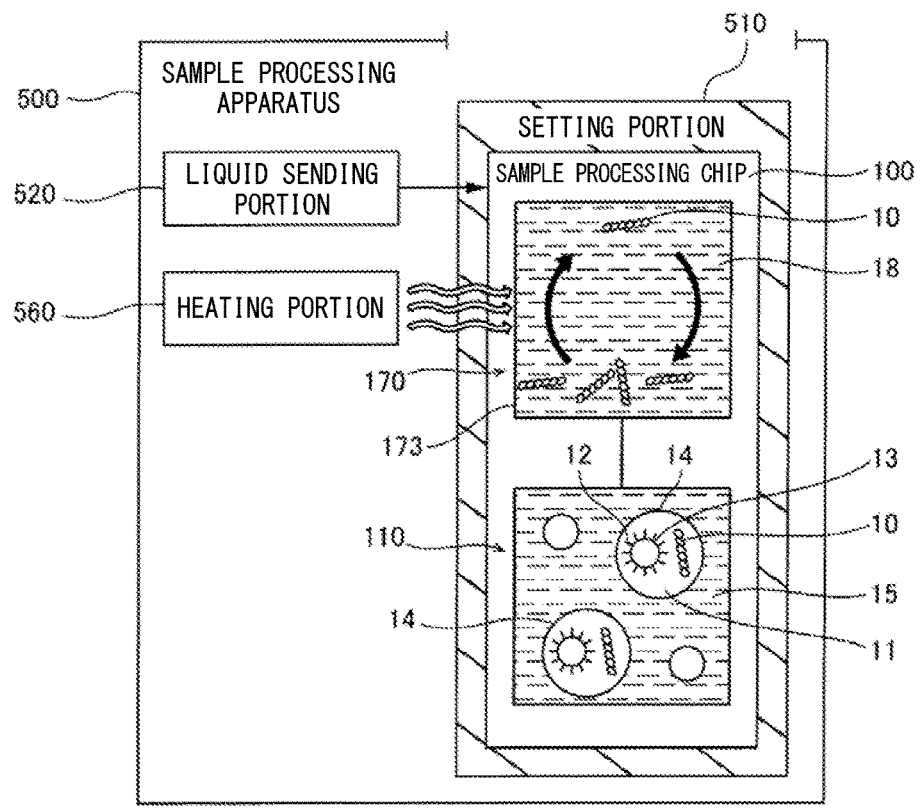
FIG. 2 is a diagram for explaining overview of the sample processing apparatus.

A sample processing chip 100 according to the present embodiment is a chip to be set in a sample processing apparatus 500 (see FIG. 2), and for processing a target component in a sample supplied by the sample processing apparatus 500. The sample processing chip 100 is configured to be able to receive a liquid containing a target component. The sample processing chip 100 is a cartridge-type chip that allows the sample processing apparatus 500 to perform sample processing by the sample processing chip 100 being set in the sample processing apparatus 500. The sample processing chip 100 is a microfluidic chip in which fine flow paths for performing desired process steps are formed as described later. Each flow path is a micro flow path whose cross-sectional dimensions (width, height, inner diameter) are each 0.1 μm to 1000 μm, for example.

The sample processing chip 100 is configured to perform predetermined sample processing for detecting the target component by one molecule or by one particle in a sample. The target component is a nucleic acid, a cell, or the like, for example. Into the sample processing chip 100, a liquid such as a body fluid or blood (whole blood, serum, or plasma) collected from a patient, or a liquid obtained by subjecting the collected body fluid or blood to a predetermined pretreatment is infused as a sample. For example, an extract of a nucleic acid from blood or the like through a predetermined pretreatment is infused into the sample processing chip 100. Extraction of the target component may be performed inside the sample processing chip 100.

The liquid containing the target component and infused into the sample processing chip 100 is sent through the sample processing chip 100 by the sample processing apparatus 500. While the liquid containing the target component is sent, a process composed of a plurality of steps is performed in a predetermined order. As a result of the plurality of process steps, a measurement specimen that is appropriate for detecting the target component is generated in the sample processing chip 100.

The sample processing chip 100 includes a dilution flow path 170 and a droplet forming flow path 110. The dilution flow path 170 and the droplet forming flow path 110 are serially arranged so that the liquid containing a target component 10 is supplied in this order. Between the dilution flow path 170 and the droplet forming flow path 110, another flow path may be provided.

Each flow path of the sample processing chip 100 may have any structure in which the liquid infused from the inlet portion of the sample processing chip 100 can flow therethrough. The flow path is formed as a groove formed in the surface of a base plate which is a component of the sample processing chip 100, or as a space formed inside the base plate, for example. Alternatively, the sample processing chip 100 provided with flow paths may be formed by mounting, to the base plate, fluid modules having respective flow paths formed therein.

Each flow path has a shape that is in accordance with a process to be performed in the flow path. The flow path is formed so as to have a flow path width, a flow path height or flow path depth, a flow path length, and a volume that are in accordance with the process to be performed in the flow path. The flow path is formed as a passage or channel in an elongated tube shape, for example. The channel can be in a linear shape, a curved shape, a zigzag shape, or the like. Although described later, the flow path may be in a shape in which flow path dimensions such as flow path width and height vary (see FIG. 33), may be in a shape in which part or the entirety of the flow path extends in a planar manner along the surface of the sample processing chip 100 (see FIG. 50), or may be in a shape in which the flowing-in liquid can be stored, for example.

When digital detection is to be executed with respect to a nucleic acid 10 as the target component, dilution of the nucleic acid 10 as the target component may be required in some cases. For digital detection, in the dilution flow path 170, the nucleic acid 10 as the target component is diluted with a diluent 18. In order to execute digital detection in the sample processing chip 100, in the dilution flow path 170, the nucleic acid 10 as the target component is diluted at a dilution rate of about 1000 fold to several ten thousand fold or several million fold, for example. In a microfluidic chip configured by fine micro flow paths, if the flow path structure and the conveyance control of the target component 10 and the diluent 18 are complicated, it is difficult to achieve the above-mentioned dilution rate for executing digital detection.

When the target component 10 is diluted with the diluent 18, it is preferable that the target component 10 is sufficiently mixed and dispersed in the mixture of the target component 10 and the diluent 18. The dilution flow path 170 includes a storage portion 173. The dilution flow path 170 is configured such that thermal convection is caused in the storage portion 173 by heat generated by a heating portion 560 disposed in the sample processing apparatus 500, thereby to mix the target component 10 and the diluent 18. In addition to this, the dilution flow path 170 can include a flow path for supplying liquid to the storage portion 173, and a flow path for sending out liquid from the storage portion 173.

The storage portion 173 is configured to store a mixture of: the target component 10; and a predetermined amount of the diluent 18 for causing the target component 10 to be encapsulated by one molecule or by one particle into a droplet. By the target component 10 being mixed with the predetermined amount of the diluent 18, limiting dilution of the target component is achieved. This is, statistically speaking, a state where the target component 10 is encapsulated by one molecule or by one particle in individual droplets 14 formed in the droplet forming flow path 110. The number of molecules or the number of particles of the target component 10 encapsulated in droplets 14 realized when the target component 10 is diluted at a certain concentration follows the Poisson distribution statistically, and can be calculated probabilistically. Even when the target component 10 is diluted in the storage portion 173 at a dilution rate calculated in advance, the number of the target component 10 encapsulated in individual droplets 14 may be 0, 1, or a plurality in some cases. However, if the number of the target component 10 encapsulated in each of a large number of droplets 14 formed in the droplet forming flow path 110 is greater than 0 and not greater than 1 on average, for example, then, the majority of the droplets 14 encapsulating the target component 10 statistically includes one molecule or one particle of the target component 10.

The storage portion 173 has a capacity that is in accordance with the diluent amount that can achieve a dilution rate for executing digital detection. The storage portion 173 has a simple shape, such as rectangle, rhombus, circle, or ellipse, for example. Accordingly, thermal convection can be easily caused in a wide range in the storage portion 173. The storage portion 173 does not require a complicated structure such as a meandering flow path that is adopted in a case where a plurality of components are mixed by a forced flow in a flow path. In the case of the dilution flow path 170, in a state where the diluent 18 and the nucleic acid 10 as the target component are stored in the storage portion 173, the nucleic acid 10 and the diluent 18 are mixed together through thermal convection. Therefore, a complicated control is not necessary to convey the target component 10 and the diluent 18.

The droplet forming flow path 110 is configured to form, in a dispersion medium 15, droplets 14 including: the target component 10 diluted in the dilution flow path 170; and a reagent 11 which reacts with the target component 10. Thus, the droplet forming flow path 110 causes the target component 10 to be encapsulated statistically by one molecule or by one particle into a droplet 14.

For example, when the target component 10 is a nucleic acid, the nucleic acid 10 is diluted in the dilution flow path 170, and then infused into the droplet forming flow path 110. The nucleic acid 10 as the target component has been diluted in the dilution flow path 170, and thus, when the nucleic acid 10 is to be encapsulated in a droplet 14, only one molecule of the nucleic acid 10 as the target component is encapsulated in the droplet 14. Since the nucleic acid 10 as the target component has been diluted in the dilution flow path 170, the nucleic acid 10 is not necessarily encapsulated in all the droplets 14 formed in the droplet forming flow path 110. For example, the nucleic acid 10 is encapsulated in about 20% droplets 14 among all the droplets 14 formed in the droplet forming flow path 110, and droplets 14 encapsulating both the nucleic acid 10 and a carrier 13 account for about 5% or less of all the droplets 14 formed in the droplet forming flow path 110.

For example, the mixture of the target component and the reagent is water-based, and the dispersion medium 15 is oil-based. As the dispersion medium 15, a liquid such as oil that is non-miscible with the mixture is used, for example. In the droplet forming flow path 110, for example, the mixture is supplied from a direction that crosses the flow direction of the dispersion medium 15, and the flow of the mixture is sheared by the flow of the dispersion medium 15, whereby droplets 14 of the mixture are formed in the dispersion medium 15. In the droplet forming flow path 110, droplets 14 may be formed by intermittently supplying a very small amount of the mixture into the flow of the dispersion medium 15. In the droplet forming flow path 110, emulsion in which droplets 14 of the mixture are dispersed in the dispersion medium 15 is formed.

When the target component 10 is a nucleic acid, in the droplet forming flow path 110, droplets 14 containing the mixture of: the nucleic acid 10 as the target component; the reagent 11 for amplification reaction of the nucleic acid 10; and the carrier 13 having added thereto a primer 12 which binds to the nucleic acid 10, are formed in the dispersion medium 15. For example, a liquid containing the nucleic acid 10, the reagent 11 for amplification reaction, and a liquid containing the carrier 13 are supplied to the droplet forming flow path 110, and mixed in the droplet forming flow path 110. These liquids may be supplied in a state of a mixture to the droplet forming flow path 110. The reagent 11 for amplification reaction includes a substance, such as DNA polymerase, that is necessary for PCR (polymerase chain reaction). As the carrier 13, a non-magnetic particle or a magnetic particle can be used.

The droplets 14 formed in the droplet forming flow path 110 may be transferred to another flow path in the sample processing chip 100 or may be discharged from the sample processing chip 100 so that the droplets 14 are transferred to an external apparatus that performs processes for executing digital detection. As examples of the processes for executing digital detection, sequentially performed are: a PCR process in which the nucleic acid 10 in the droplets 14 formed in the droplet forming flow path 110 is amplified in the droplets 14; a process of breaking the droplets 14 containing the carrier 13 in which the amplification product of the nucleic acid 10 is bound to the primer 12; a hybridization process in which the carriers 13 taken out of the broken droplets 14 are collected, and the amplification product on the collected carriers 13 and a labeled substance for detecting the amplification product are reacted to each other; and the like. The labeled substance is a substance that is designed so as to specifically bind to DNA as the detection target and that emits fluorescence as an optical signal. In this case, the nucleic acid can be detected on the basis of the labeling, by use of a flow cytometry or the like in which fluorescence generated upon application of laser is detected by a detector.

The sample processing chip 100 may further include flow paths for performing these respective processes. In that case, a large portion or the entirety of a series of sample processing for executing digital detection can be performed in the sample processing chip 100.

According to the sample processing chip 100 and a sample processing method of the present embodiment, in the storage portion 173 of the dilution flow path 170, the target component 10 and the diluent 18 are mixed together through thermal convection. Thus, for example, the storage portion 173 can be formed in a simple shape such as rectangle or rhombus. Accordingly, the storage portion 173 does not require a complicated structure such as a flow path having a meandering shape. In the dilution flow path 170, the target component 10 and the diluent 18 are mixed together through thermal convection in a state where the diluent 18 and the target component 10 are stored in the storage portion 173. Thus, the dilution flow path 170 does not require complicated control for conveying the target component 10 and the diluent 18. As a result, even when processes for executing digital detection are performed by use of the sample processing chip 100, it is possible to mix the target component 10 and the diluent 18 together, without making complicated the flow path structure and the conveyance control for the target component 10 and the diluent 18.

[Overview of Sample Processing Apparatus]

Next, overview of the sample processing apparatus according to the present embodiment will be described.

The sample processing apparatus 500 is a sample processing apparatus for processing a target component in a sample by use of the sample processing chip 100.

The sample processing apparatus 500 includes: a setting portion 510 in which to set the sample processing chip 100; a liquid sending portion 520; and the heating portion 560.

The setting portion 510 is formed in a shape corresponding to the sample processing chip 100, and supports the sample processing chip 100. The setting portion 510 has a structure in which at least one of the main surface and the rear surface of the sample processing chip 100 is open, in order to provide connection to the flow paths in the sample processing chip 100 and in order to dispose thereon units to be used in various process steps in the sample processing chip 100.

The liquid sending portion 520 has a function of supplying to the sample processing chip 100 a liquid containing the target component such as the nucleic acid 10 and the diluent 18 for diluting the target component 10, and of transferring the liquid and the diluent 18. The liquid sending portion 520 is formed as a combination of pumps and valve units, for example, and transfers the liquid in the sample processing chip 100 by pressure. Thus, after supplying the target component 10 and the diluent 18 into the storage portion 173, the liquid sending portion 520 can cause the target component 10 and the diluent 18 to be held in the storage portion 173. Accordingly, until mixing of the target component 10 and the diluent 18 through thermal convection is completed, the mixture of the target component 10 and the diluent 18 can be held in the storage portion 173.

The liquid sending portion 520 not only supplies and the diluent 18 and the liquid containing the target component 10, but also supplies to the sample processing chip 100 various kinds of reagents to be used in the sample processing chip 100, for example. The liquid sending portion 520 is connected to a reservoir that holds the liquid containing the nucleic acid, and reservoirs that hold various kinds of reagents including the diluent 18, for example, and supplies such liquid and reagents.

By supplying a positive pressure, the liquid sending portion 520 can advance liquid in the sample processing chip 100 in accordance with the order of steps, and can discharge liquid from the sample processing chip 100. The liquid sending portion 520 may transfer liquid in the sample processing chip 100 or discharge liquid therefrom, by supplying a negative pressure.

Control of the liquid sending portion 520 is performed by controlling the supply pressure of the liquid sending portion 520, by means of a flow rate sensor, a pressure sensor, and the like provided in the liquid supply route, for example. In a case where a quantitative pump such as a syringe pump or a diaphragm pump is used in the liquid sending portion 520, the flow rate sensor is not necessarily required.

The heating portion 560 heats the mixture of the target component 10 and the diluent 18 supplied to the storage portion 173 in the sample processing chip 100. The heating portion 560 heats the mixture in the storage portion 173 so as to realize temperature distribution in which a relatively warm region and a relatively cold region can be formed. By forming the temperature distribution in the mixture in the storage portion 173, the heating portion 560 causes thermal convection in the storage portion 173. The thermal convection of the mixture accelerates the mixing of the target component 10 and the diluent 18.

The heating portion 560 includes a thermoelectric element, such as a heating wire for example, that converts electric energy into thermal energy, and the heating portion 560 itself generates heat thereby heating the sample processing chip 100. The heating portion 560 may heat the sample processing chip 100 or the liquid in the storage portion 173 by use of light, electromagnetism, or the like, for example. By heating a part of the storage portion 173, for example, the heating portion 560 forms temperature distribution in the mixture in the storage portion 173. In a case where the heating portion 560 itself has temperature distribution, the heating portion 560 may heat the entirety of the storage portion 173.

In a case where a process other than the dilution process and the droplet forming process is further performed in the sample processing chip 100, the sample processing apparatus 500 may further include processing units that are used in process steps to be performed. Examples of the processing units to be used in various kinds of process steps include: a heater unit or a cooling unit that controls the temperature cycle of the liquid at the time of a PCR process; a magnet unit that causes magnetic force to act on the liquid; a camera unit that takes images of the liquid; and a detection unit. These processing units are provided so as to correspond to at least one of a plurality of flow paths, and are configured to operate when process steps are performed in the corresponding flow path. In that case, a large portion or the entirety of a series of sample processing for executing digital detection can be performed by the sample processing apparatus 500.

The sample processing apparatus 500 performs a series of sample processing for nucleic acid detection by use of the sample processing chip 100. That is, the sample processing apparatus 500 supplies the target component 10 and the diluent 18 to the dilution flow path 170 by means of the liquid sending portion 520. The sample processing apparatus 500 causes the heating portion 560 to provide heat to the storage portion 173, thereby to cause thermal convection in the storage portion 173 of the dilution flow path 170.

As described above, in the present embodiment, the sample processing apparatus 500 includes the heating portion 560 which heats the mixture of the target component 10 and the diluent 18 stored in the storage portion 173, thereby causing the target component 10 and the diluent 18 to be mixed together through thermal convection. Since the mixing is performed by use of thermal convection, the storage portion 173 of the dilution flow path 170 can be in a simple shape such as rectangle or rhombus, for example. Since in the dilution flow path 170, the target component 10 and the diluent 18 are mixed together through thermal convection in a state where the diluent 18 and the target component 10 are stored in the storage portion 173, complicated control is not required for conveyance of the target component 10 and the diluent 18. As a result, also when performing processes for executing digital detection by use of the sample processing chip 100, it is possible to mix the target component 10 and the diluent 18 together, without making complicated the flow path structure and the conveyance control of the target component 10 and the diluent 18.

[Configuration Example of Sample Processing Chip]

Figure 3:
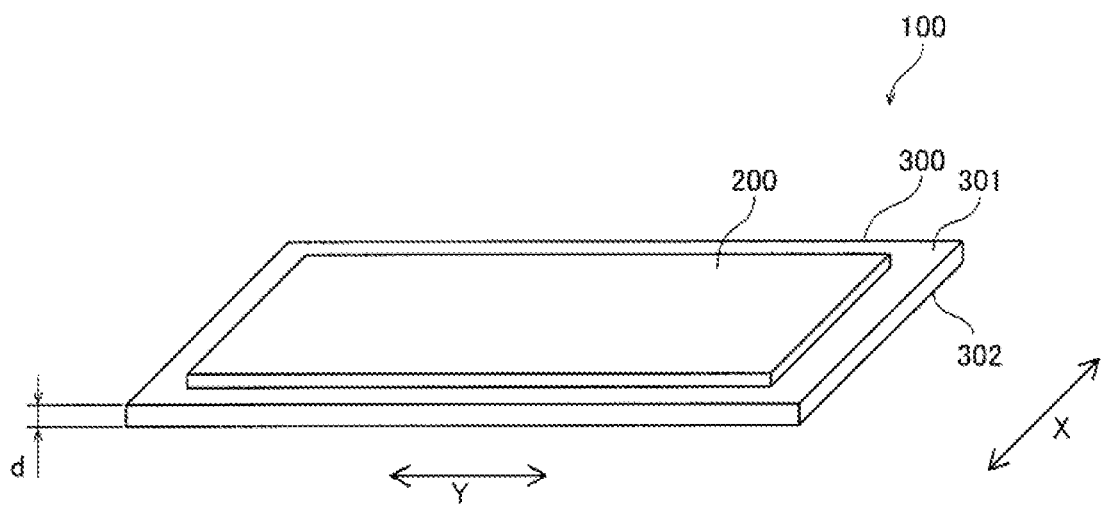
FIG. 3 is a perspective view showing a configuration example of the sample processing chip.

FIG. 3 shows a configuration example of the sample processing chip 100 according to the present embodiment. The sample processing chip 100 includes a fluid module 200 and a base plate 300. The fluid module 200 is set on the base plate 300. The fluid module 200 includes the dilution flow path 170 and the droplet forming flow path 110, for example.

Figure 4:
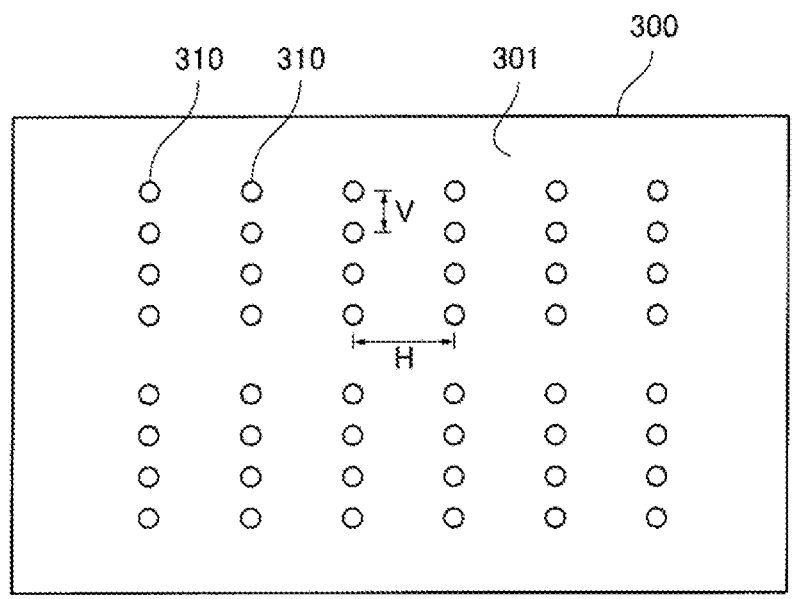
FIG. 4 is a plan view showing a configuration example of a base plate of the sample processing chip.

FIG. 4 shows a configuration example of the base plate 300. The base plate 300 has a flat plate shape, and has a first face 301 which is the main surface, and a second face 302 (see FIG. 3). The sample processing chip 100 is a plate-like member in which the fluid module 200 having a flat plate shape is set on the base plate 300. The first face 301 of the base plate 300 can be considered as the main surface of the sample processing chip 100. Hereinafter, the first face 301 may be referred to as "main surface 301". The second face 302 is the face opposite to the first face 301. In FIG. 3, the upper face of the base plate 300 is defined as the first face 301, but the first face 301 may be the lower face of the base plate 300. The base plate 300 is formed from a rigid material. For example, the base plate 300 is formed from glass. Accordingly, even when the pressure of liquid to be supplied to the fluid module 200 is increased in accordance with a process step, sufficient pressure-resisting ability of the base plate 300 can be assured. The base plate 300 has a rectangular shape that includes long sides extending in a longitudinal direction Y and short sides extending in a short direction X, for example.

A thickness d (see FIG. 3) of the base plate 300 is not less than 0.1 mm and not greater than 5 mm, for example. Accordingly, the base plate 300 can be formed so as to have a sufficiently large thickness, compared with the flow path height (on the order of about 10 μm to 500 μm) of each flow path formed in the fluid module 200. From a viewpoint of easy securement of sufficient pressure-resisting ability of the base plate 300, the thickness d of the base plate 300 is preferably not less than 1 mm and not greater than 5 mm.

The base plate 300 has through-holes 310 through which liquid is infused into the fluid module 200, for example. The through-holes 310 are each a through-hole that penetrates the base plate 300 in the thickness direction thereof. The through-holes 310 are not only connected to flow paths of the fluid module 200, but also can each function as a port 101 (see FIG. 7) for supplying a liquid or a reagent to the sample processing chip 100, or a port 102 (see FIG. 7) for collecting liquid from the sample processing chip 100. Accordingly, liquid can be infused via the base plate 300 which allows easier securement of pressure-resisting ability than the fluid module 200 having flow paths formed therein. Thus, liquid infusion at a sufficient pressure can be easily realized.

It should be noted that the port 101 and the port 102 of the sample processing chip 100 may not be configured by the through-hole 310. For example, the port 101 and the port 102 may be formed at the fluid module 200.

In the example shown in FIG. 4, the base plate 300 has two sets of 4 rows×6 columns of the through-holes 310. In a case where a plurality of sets of the through-holes 310 are provided to the base plate 300, the fluid modules 200 can be provided in a plurality of columns on the base plate 300. In this case, by use of a single sample processing chip 100, it is possible to perform sample processing in parallel. The number of the through-holes 310 and the number of sets of the through-holes 310 provided to the base plate 300 is not limited to those of the example shown in FIG. 4. The base plate 300 may have one set of 8 rows×6 columns of the through-holes 310.

The through-holes 310 are arranged at predetermined pitches on the base plate 300, for example. In the example shown in FIG. 4, the through-holes 310 are arranged at a pitch V in the vertical direction and at a pitch H in the horizontal direction. In this case, the fluid module 200 can be disposed on the base plate 300 at a desired position according to the pitch unit, and the flow paths can be connected to desired through-holes 310. Thus, even in a case where the structure such as the shape of a flow path of the fluid module 200 is to be changed, the structure on the base plate 300 side need not be changed, and thus flexible design change can be realized.

Figure 5:
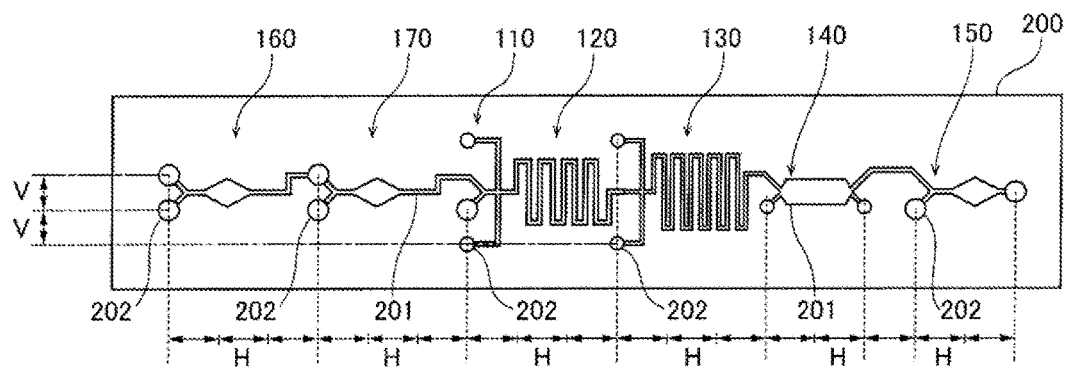
FIG. 5 is a plan view showing a configuration example of a fluid module.

FIG. 5 shows a configuration example of the fluid module 200. In this configuration example, the fluid module 200 further includes a first flow path 160, a second flow path 120, a third flow path 130, a fourth flow path 140, and a fifth flow path 150, in addition to the dilution flow path 170, and the droplet forming flow path 110.

The fluid module 200 includes: channels 201 which are each a flow path in which a liquid such as a sample or a reagent flows; and connection portions 202 which are each connected to a through-hole 310. Each connection portion 202 is used for infusing liquid into a channel 201, or for drawing out liquid from a channel 201. Each flow path is formed as a combination of these channels 201 and connection portions 202. Details of the fluid module 200 will be described later.

Each connection portion 202 is disposed at a position that corresponds to one of the through-holes 310 formed at the predetermined pitches V and H on the base plate 300, and is connected to the through-hole 310. That is, the connection portions 202 are arranged on the fluid module 200 at pitches of an integer multiple of the pitches V and H of the through-holes 310 in the base plate 300. The channels 201 are disposed so as to connect connection portions 202 arranged at the predetermined pitches.

Figure 6:
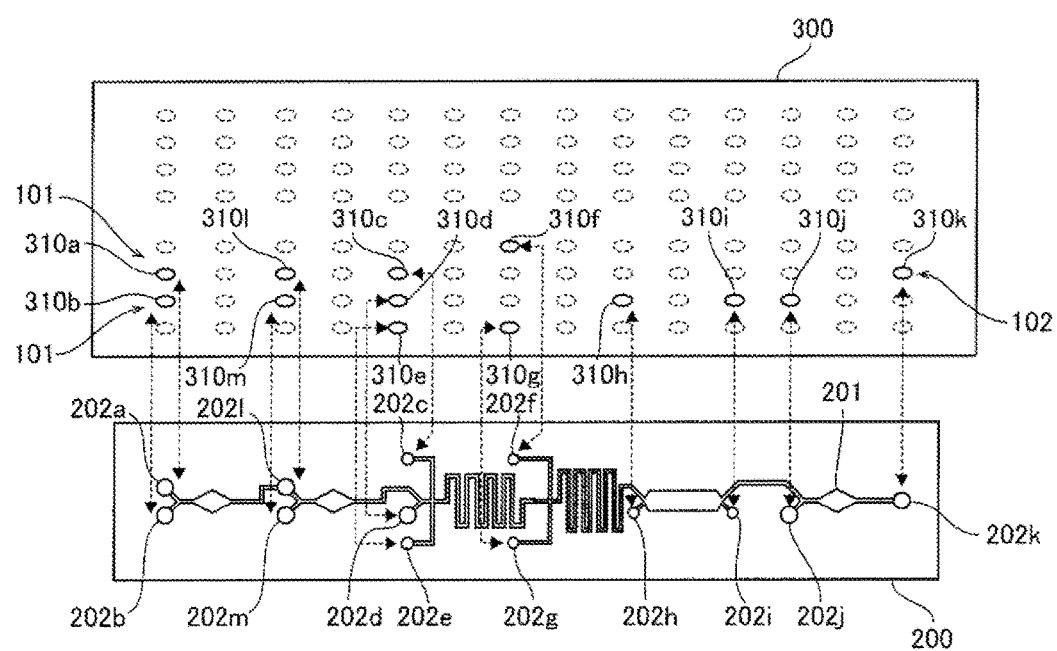
FIG. 6 is a schematic plan view showing an arrangement example of the fluid module on the base plate.
Figure 7:
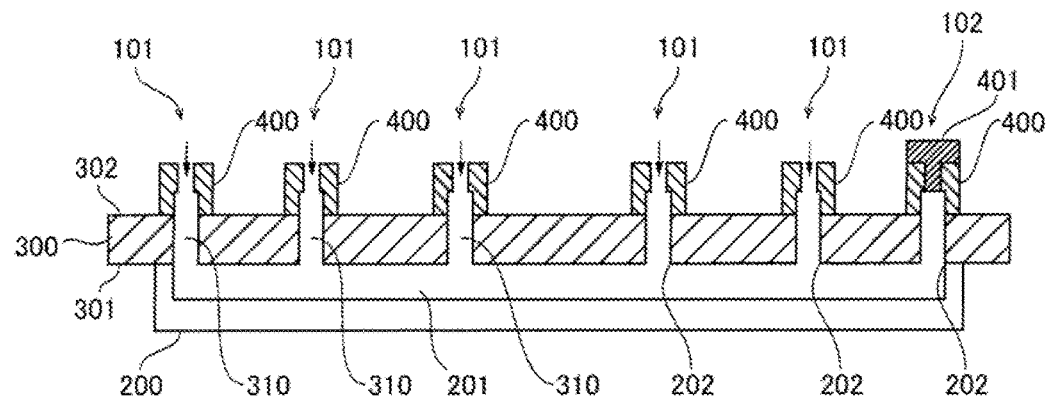
FIG. 7 is a schematic vertical cross-sectional view showing an arrangement example of the fluid module on the base plate.

FIG. 6 and FIG. 7 show an arrangement example of the fluid module 200 on the base plate 300. In the example shown in FIG. 6, the connection portions 202 of the fluid module 200 are arranged so as to be aligned with their corresponding through-holes 310 in the base plate 300, respectively. Due to the correspondence between the connection portions 202 of the fluid module 200 and the through-holes 310 in the base plate 300, even when the fluid module 200 and the base plate 300 separately formed are to be joined together, the connection portions 202 and their corresponding through-holes 310 can be connected to each other easily and at one time.

The through-holes 310 may be formed only at positions necessary for providing connection to various kinds of fluid modules 200 that are arranged on the base plate 300. In the example shown in FIG. 6, for example, corresponding to connection portions 202a to 202m of the fluid module 200, through-holes are respectively formed at the positions of through-holes 310a to 310m indicated by solid lines. Accordingly, the structure of the base plate 300 can be further simplified. As shown in FIG. 4, the through-holes 310 may be formed at predetermined pitches across the base plate 300.

The fluid module 200 is connected to the base plate 300 by solid-phase welding, for example. As solid-phase welding, a method of subjecting surfaces to be joined to plasma processing to form OH radicals, thereby to join the surfaces by hydrogen bonds, a method of vacuum pressure welding, or the like can be adopted, for example. Through solid-phase welding, the fluid module 200 and the base plate 300 can be firmly joined together. Accordingly, even when the pressure of liquid to be supplied to the fluid module 200 is high, sufficient pressure-resisting ability of the base plate 300 can be assured. It should be noted that the fluid module 200 may be connected to the base plate 300 with an adhesive or the like.

The base plate 300 can include a through-hole 310 for infusing into the sample processing chip 100 a test liquid that is to be used in at least one of a plurality of steps. A through-hole 310 for infusing liquid is connected to at least one connection portion 202 of the fluid module 200 disposed on the base plate 300.

In the example shown in FIG. 6 and FIG. 7, each of through-holes 310a to 310j, 310l, and 310m in the base plate 300 function as a port 101 for infusing liquid. The through-holes 310a to 310j, 310l, and 310m are respectively connected to the connection portion 202a to 202j, 202l, and 202m of the fluid module 200. A through-hole 310k is connected to a connection portion 202k of the fluid module 200 and functions as a port 102 for collecting liquid.

A sample or a reagent is infused into a through-hole 310 that functions as a port 101 via a jig such as a connector 400 (see FIG. 7). The jig such as the connector 400 is connected to the end of the through-hole 310 on the opposite side to the end thereof at the fluid module 200 side. That is, the jig such as the connector 400 is set at the second face 302 opposite to the first face 301 of the base plate 300 on which the fluid module 200 is disposed.

The dilution flow path 170, the droplet forming flow path 110, and the first flow path 160 to the fifth flow path 150 may be formed, divided into a plurality of the fluid module 200. In the example shown in FIG. 8, the sample processing chip 100 includes: a plurality of the fluid modules 200 in which the dilution flow path 170 and the droplet forming flow path 110 are respectively formed; the base plate 300 on which the plurality of the fluid modules 200 are arranged; and a connection flow path 350 which connects the fluid modules 200 arranged on the base plate 300 and which is for causing the diluted target component to be moved from the dilution flow path 170 to the droplet forming flow path 110. Accordingly, the dilution flow path 170 and the droplet forming flow path 110 can be formed in separate fluid modules 200, respectively, and thus, layout restriction can be reduced and the shapes of the respective flow paths can be easily optimized.

Figure 8:
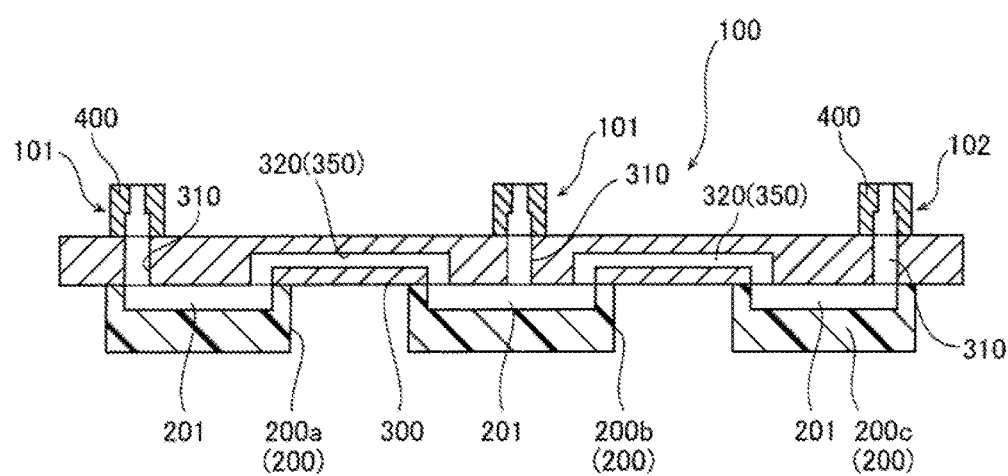
FIG. 8 is a vertical cross-sectional view showing a first modification of the sample processing chip.

In the example shown in FIG. 8, the sample processing chip 100 includes three fluid modules 200a, 200b, and 200c. The connection flow path 350 is configured to connect the plurality of the fluid modules 200a to 200c and to send liquid.

The plurality of the fluid modules 200 are each provided separately to the base plate 300. That is, the plurality of the fluid modules 200 are not a plurality of element portions formed in a common member, but are separate components independent of one another. Each fluid module 200 is structured such that a flow path is formed in a block body formed from resin, glass, or the like, for example. In addition, the plurality of the fluid modules 200 is set to the base plate 300 in a state where the fluid modules 200 are distanced from one another. Since the plurality of the fluid modules 200 are each set to the base plate 300 and are connected to one another via the connection flow path 350, liquid can be transferred between the fluid modules.

In the example shown in FIG. 8, each of the fluid modules 200a, 200b, and 200c includes, i.e., is in charge of, one or a plurality of members among the droplet forming flow path 110, the dilution flow path 170, and the first flow path 160 to the fifth flow path 150. As one example, in the respective fluid modules 200a, 200b, and 200c, the first flow path 160 and the dilution flow path 170, the droplet forming flow path 110 and the second flow path 120, and the third flow path 130 to the fifth flow path 150 are individually formed. The combination of flow paths that each fluid module 200 is in charge of is not limited thereto.

In this example, the base plate 300 includes a base plate flow path 320 which connects adjacent fluid modules 200a, 200b, and 200c together. In the example shown in FIG. 8, the connection flow path 350 is formed by the base plate flow path 320 which is integrally formed in the base plate 300. Accordingly, via the base plate flow path 320, liquid can be transferred in a predetermined order according to the order of process steps, to each of the droplet forming flow path 110, the dilution flow path 170, and the first flow path 160 to the fifth flow path 150. The connection flow path 350 may connect the fluid modules 200 together, in the form of a combination such as a tube member and the base plate flow path 320 which may be formed by a tube member or the like provided separately from the base plate 300 and the fluid module 200, for example.

Figure 9:
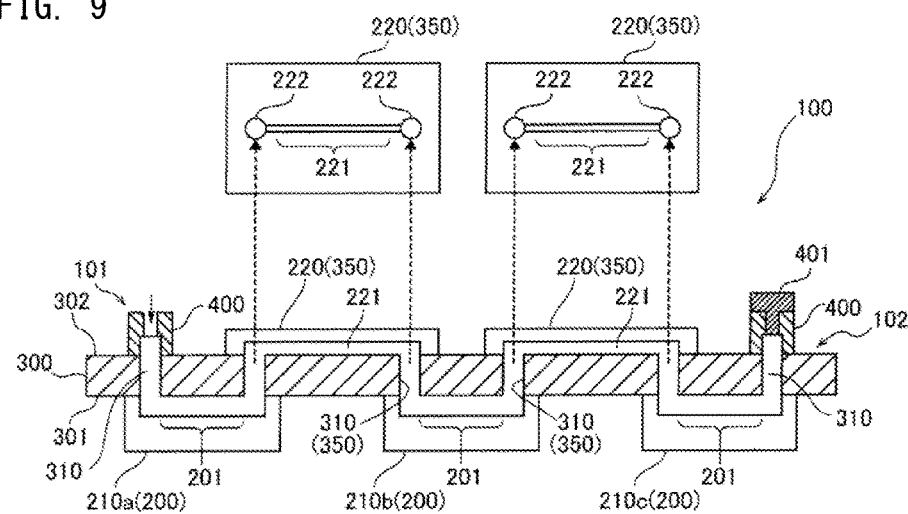
FIG. 9 is a vertical cross-sectional view showing a second modification of the sample processing chip.

In the configuration example shown in FIG. 9, the sample processing chip 100 includes second fluid modules 220 each for connecting adjacent first fluid modules 210a, 210b, and 210c together, on the second face 302 which is opposite to the first face 301 on which the first fluid modules 210 are disposed. In the base plate 300, the through-holes 310 are formed, but the base plate flow path 320 is not formed. In the example shown in FIG. 9, the connection flow path 350 is formed by the second fluid modules 220 and the through-holes 310 integrally formed in the base plate 300.

In each second fluid module 220, connection portions 222 to be respectively connected to through-holes 310, and a channel 221 connecting the connection portions 222 are formed. The liquid discharged from the first fluid module 210a is transferred to the adjacent first fluid module 210b via a through-hole 310 and a second fluid module 220. The liquid having flowed into one of the connection portions 222 of the second fluid module 220 passes through the channel 221, is discharged from the other of the connection portions 222, passes through a through-hole, and then flows into the first fluid module 210b. Similarly, the liquid discharged from the first fluid module 210b is transferred to the adjacent first fluid module 210c, via a through-hole 310 and a second fluid module 220.

Accordingly, even in a configuration in which the droplet forming flow path 110, the dilution flow path 170, and the first flow path 160 to the fifth flow path 150 are formed, divided in a plurality of the fluid modules 200, and the base plate 300 is provided with only the through-holes 310, liquid can be transferred via the second fluid modules 220 in a predetermined order according to the order of process steps, to each of the droplet forming flow path 110, the dilution flow path 170, and the first flow path 160 to the fifth flow path 150.

In the second fluid module 220, one or a plurality of members among the droplet forming flow path 110, the dilution flow path 170, and the first flow path 160 to the fifth flow path 150 may be formed. In that case, the first fluid modules 210a, 210b, and 210c and the second fluid modules 220 each have formed therein, i.e., are each in charge of, one or a plurality of members among the droplet forming flow path 110, the dilution flow path 170, and the first flow path 160 to the fifth flow path 150.

As in the configuration examples shown in FIG. 8 and FIG. 9, in a case where the droplet forming flow path 110, the dilution flow path 170, and the first flow path 160 to the fifth flow path 150 are individually formed, i.e., divided, in a plurality of the fluid modules 200 and 210, the structures of the fluid modules such as the materials of the individual fluid modules 200 (210), the flow path dimensions (width and depth), the dimensions of the fluid module 200 (210) itself can be made different from one another. That is, the structure of each fluid module can be optimized in accordance with the process step in each of the droplet forming flow path 110, the dilution flow path 170, and the first flow path 160 to the fifth flow path 150.

For example, the first fluid modules 210a, 210b, 210c are formed from different materials, respectively. Each fluid module 200 can be formed by selecting a material of an appropriate quality in accordance with the kind of the flow path formed in the fluid module.

Specifically, it is preferable that the dilution flow path 170 is formed from a material of a quality that is less likely to allow the target component 10 to attach the inner wall surface of the storage portion 173. An example of such a material is a cycloolefin polymer (COC) or a cycloolefin copolymer (COP). Accordingly, when transferring the diluted mixture from the storage portion 173, it is possible to suppress the target component 10 from attaching to the inner wall surface of the storage portion 173.

In the droplet forming flow path 110, in a case where an oil is used as the dispersion medium 15, and a water-based mixture and the oil-based dispersion medium are present, it is preferable that the droplet forming flow path 110 is formed from a hydrophobic material or a fluorinated material. Examples of such a material include polydimethylsiloxane (PDMS) and polymethyl methacrylate resin (PMMA). Accordingly, droplets 14 of the mixture are prevented from attaching to the inner wall surface of the droplet forming flow path 110, and droplets 14 having a uniform shape can be efficiently formed in the dispersion medium 15.

For example, in one configuration example shown in FIG. 9, in the first fluid modules 210a and 210b, the dilution flow path 170 and the droplet forming flow path 110 are formed, respectively. The first fluid module 210a having the dilution flow path 170 is formed from a cycloolefin polymer (COC) or a cycloolefin copolymer (COP). The fluid module 210b having the droplet forming flow path 110 is formed from a polydimethylsiloxane (PDMS) or a polymethyl methacrylate resin (PMMA). Therefore, the dilution flow path 170 and the droplet forming flow path 110 are respectively provided to the fluid modules 200 (210) formed from different materials from each other. Accordingly, in the sample processing chip 100, the dilution flow path 170 and the droplet forming flow path 110 can be formed from materials that are appropriate for respective functions, and thus, the process efficiencies in the individual flow paths are improved, and the processing performance of the sample processing chip 100 is improved.

[Configuration Example of Sample Processing Apparatus]

Figure 10:
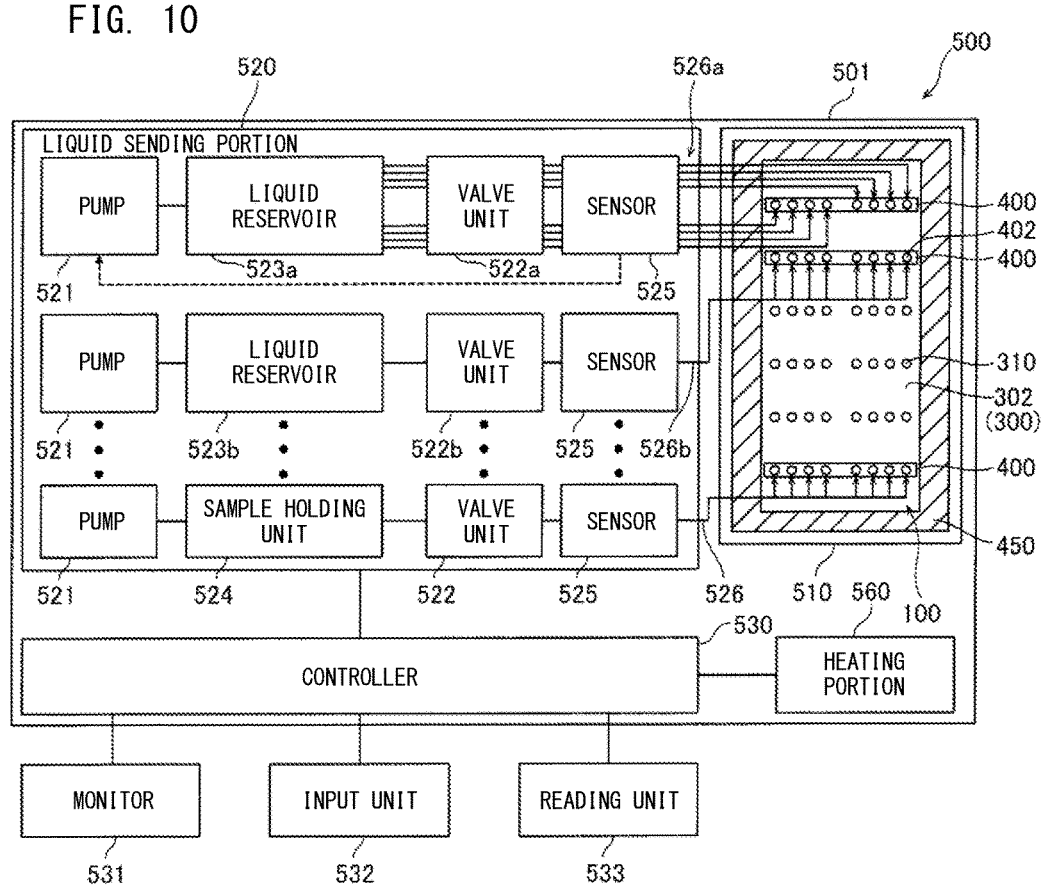
FIG. 10 is a block diagram showing a configuration example of a sample processing apparatus.

FIG. 10 shows a configuration example of the sample processing apparatus 500. The sample processing apparatus 500 has functions of liquid infusion into the sample processing chip 100, liquid collection from the sample processing chip 100, detection of reaction that has occurred in the sample processing chip 100, and the like.

In the configuration example shown in FIG. 10, the liquid sending portion 520 includes: a pump 521 which controls the pressure for driving liquid; and a valve unit 522 which controls turning on/off of pressure supply to liquid. The liquid sending portion 520 also includes: a liquid reservoir 523 which holds liquid to be infused into the sample processing chip 100; and a sample holding unit 524. Furthermore, the liquid sending portion 520 includes a flow rate sensor 525 which measures the flow rate of liquid flowing in the sample processing chip.

The pump 521, the liquid reservoir 523, the valve unit 522 and the flow rate sensor 525 are sequentially connected by a liquid sending tube 526. The sample processing apparatus 500 performs liquid infusion to the sample processing chip 100 and liquid collection from the sample processing chip 100 via a connector 400 by means of the pump 521, the liquid reservoir 523, and the valve unit 522. In the example shown in FIG. 10, one set of the pump 521, the liquid reservoir 523, and the valve unit 522 correspond to a predetermined connector 400. For example, the sample processing apparatus 500 has the sets of the pump 521, the liquid reservoir 523, and the valve unit 522, by the same number as the number (i.e., the number of rows of ports) of connectors 400 that are connectable to the sample processing chip 100. However, at least one liquid reservoir 523 is configured as a sample holding unit 524 that holds a sample.

For example, to one pump 521, a plurality of liquid reservoirs 523 and a plurality of valve units 522 may be connected. By the valve units 522 switching the route, a plurality of liquids and reagents can be supplied to the sample processing chip 100 by use of one pump 521 that is used in common.

The pump 521 applies a pressure to the liquid reservoir 523 or the sample holding unit 524. By the pump 521 applying a positive pressure to the liquid reservoir 523, liquid is sent out from the liquid reservoir 523. By the pump 521 applying a negative pressure to the liquid reservoir 523, liquid is flowed from the sample processing chip 100 into the liquid reservoir 523. The pump 521 is a pressure pump that supplies a pneumatic pressure, for example. Alternatively, a syringe pump, a diaphragm pump, or the like can be adopted as the pump 521.

The sample processing apparatus 500 includes a controller 530. The controller 530 can individually control the operation of each pump 521. By individually controlling each pump 521, the controller 530 can perform individual liquid sending control for each of the flow paths provided in the sample processing chip 100.

For example, the controller 530 controls the liquid sending portion 520 such that, after the dilution process in the dilution flow path 170, the liquid containing the nucleic acid 10 continuously flows through the droplet forming flow path 110, the second flow path 120, and the third flow path 130. Accordingly, the time required in the sample processing can be easily shortened.

In the configuration shown in FIG. 10, each flow rate sensor 525 detects the flow rate (an example of unit: μL/min) of its corresponding liquid flowing in liquid sending tube 526. The flow rate sensor 525 feeds back the detection result of the flow rate to the pump 521. The pump 521 controls the pressure in accordance with the feedback from the flow rate sensor 525.

The flow rate sensor 525 may provide the feedback to the controller 530. On the basis of the flow rate measured by the flow rate sensor 525, the controller 530 controls the pressure of the liquid sending portion 520 for liquid transfer. Accordingly, the supply pressure at the time of supplying the sample processing chip 100 with a reagent or a sample containing the nucleic acid can be accurately controlled.

Each connector 400 is provided to a cover 621 described later of the setting portion 510, for example. The connector 400 is connected to the liquid sending tube 526. Liquid of a sample or the like is sent via the connector 400 to the sample processing chip 100. Meanwhile, liquid is collected via the connector 400 from the sample processing chip 100.

The sample processing chip 100 is set to the setting portion 510. For example, the sample processing chip 100 is held such that the second face 302 of the base plate 300 faces upward. The end on the second face 302 side of each through-hole 310 is connected to the connector 400.

Meanwhile, for example, the setting portion 510 is configured to hold the sample processing chip 100 in a state where either the longitudinal direction or the short direction in the main flat face (i.e., the first face 301 of the base plate 300) of the sample processing chip 100 having a flat plate shape is aligned with the gravity direction. In a case where the sample processing chip 100 has a rectangle plate-like shape, the setting portion 510 holds the sample processing chip 100 in a state where the long side or the short side of the sample processing chip 100 is substantially aligned with the gravity direction.

In other words, the setting portion 510 holds the sample processing chip 100 such that the first face 301 and the second face 302 of the base plate 300 are substantially parallel to the gravity direction. Accordingly, the storage portion 173 in the dilution flow path 170 formed along the sample processing chip 100 having a flat plate shape can be disposed along the gravity direction. Thus, thermal convection can be effectively generated. The setting portion 510 may hold the sample processing chip 100 such that the first face 301 and the second face 302 of the base plate 300 is inclined by a predetermined angle of less than 90 degrees relative to the gravity direction. For thermal convection, it is preferable to dispose the storage portion 173 along the gravity direction as much as possible. Thus, it is preferable that the predetermined angle is closer to 0 degrees as much as possible.

The sample processing chip 100 may include a fixture 450 for setting the sample processing chip 100 to the setting portion 510. The fixture 450 may be separable from the setting portion 510, or may be fixed to the setting portion 510.

In addition to these, the sample processing apparatus 500 can include a monitor 531, an input unit 532, a reading unit 533, and the like. The controller 530 causes the monitor 531 to display a predetermined display screen in accordance with the operation of the sample processing apparatus 500. The sample processing apparatus 500 may be connected to an external computer (not shown), and may cause a screen to be displayed on the monitor of the computer. The input unit 532 is composed of a keyboard, for example, and has a function of receiving input of information. The reading unit 533 is composed of, for example, a code reader for bar code, two-dimensional code, or the like, or a tag reader for RFID tag or the like. The reading unit 533 has a function of reading information given to the sample processing chip 100. The reading unit 533 can also read information of a sample container (not shown) containing a sample, or the like.

(Configuration Example of Valve Unit)

Figure 11:
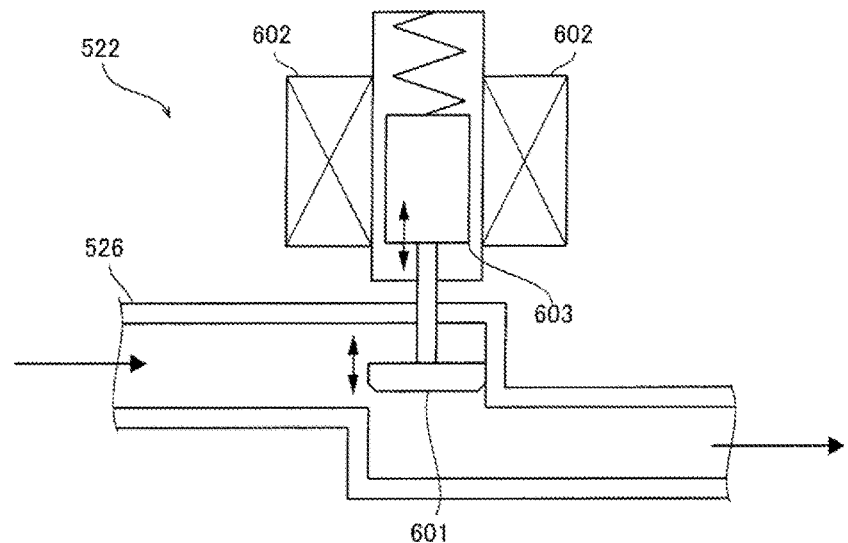
FIG. 11 is a cross-sectional view showing a configuration example of a valve unit.

FIG. 11 shows a configuration example of the valve unit 522. The valve unit 522 controls, by means of a valve 601, sending-out of liquid from the liquid reservoir 523 and flowing-in of liquid into the liquid reservoir 523.

The valve unit 522 is a solenoid valve, for example. The valve unit 522 includes a coil 602. The coil 602 moves a plunger 603 between an open position and a closed position through magnetic field generated by electric current flowing in the coil 602. The controller 530 controls the electric current flowing in the coil 602. In response to the movement of the plunger 603, the valve 601 opens/closes the liquid sending tube 526.

As shown in the example in FIG. 10, a plurality of the valve units 522 is disposed in the sample processing apparatus 500. The controller 530 can individually control opening/closing of each valve unit 522.

By controlling opening/closing of each valve unit 522 of the liquid sending portion 520, the controller 530 causes the liquid in the sample processing chip 100 to be transferred to the dilution flow path 170 and the droplet forming flow path 110, by pressure.

For example, on the basis of the elapsed time from infusion of liquid into the sample processing chip 100, or on the basis of the infused amount of liquid into the sample processing chip 100, the controller 530 controls the timing to open the relevant valve unit 522. Accordingly, on the basis of the elapsed time at a constant flow rate, and on the basis of the infused amount of liquid, the supplied amount of the liquid into the sample processing chip 100 can be accurately controlled. This realizes quantitative supply of each of various kinds of liquids appropriate for the respective flow paths in the sample processing chip 100. It should be noted that the controller 530 may determine the timing to open each valve unit 522, on the basis of a result of image analysis regarding the flow of the liquid in the sample processing chip 100, for example.

(Configuration Example of Liquid Sending Tube)

As indicated between a liquid reservoir 523*a* and a valve unit 522*a*, and between the valve unit 522*a* and a connector 400, for example, the sample processing apparatus 500 has liquid sending tubes 526*a* by the number that corresponds to the number of holes 402 in the connector 400. In the example shown in FIG. 10, eight liquid sending tubes 526*a* are provided between the liquid reservoir 523*a* and the valve unit 522*a*, and between the valve unit 522*a* and the connector 400. In this case, the valve unit 522*a* is provided for each of the eight liquid sending tubes 526*a*.

As indicated between a liquid reservoir 523*b* and a valve unit 522*b*, and between the valve unit 522*b* and a connector 400, for example, the sample processing apparatus 500 may have a liquid sending tube 526*b* that branches so as to correspond to the holes 402 in the connector 400. In the example shown in FIG. 10, one liquid sending tube 526*b* is provided between the liquid reservoir 523*b* and the valve unit 522*b*, and this liquid sending tube 526*b* branches so as to correspond to the respective holes 402 in the connector 400.

(Configuration Example of Liquid Reservoir and Sample Holding Unit)

Figure 12:
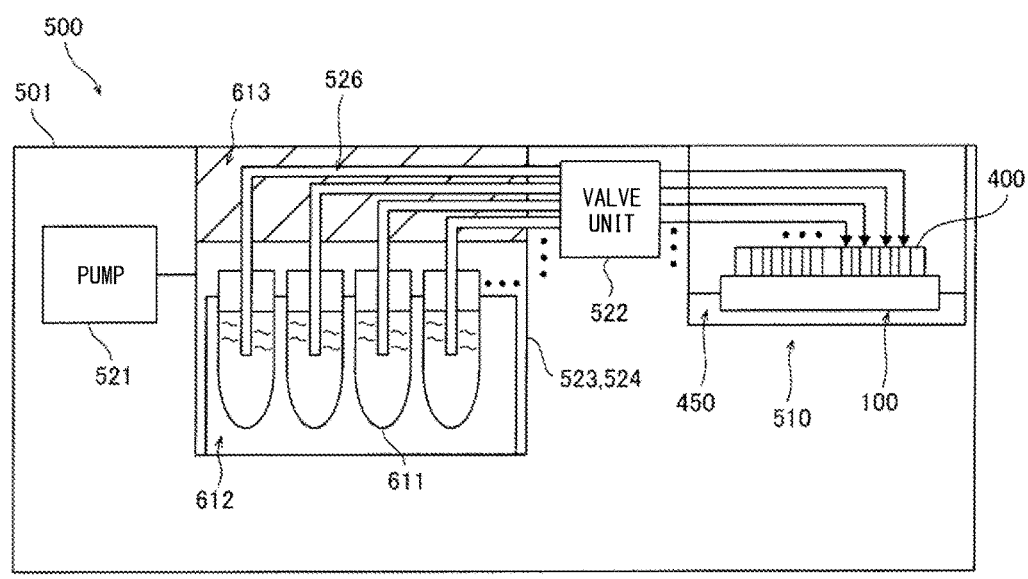
FIG. 12 is a vertical cross-sectional view showing a configuration example of a liquid reservoir.

FIG. 12 shows a configuration example of the liquid reservoir 523 and the sample holding unit 524.

Liquid containers 611 for sample, reagent, diluent, and the like are disposed in a container setting portion 612 in the liquid reservoir 523 and the sample holding unit 524. As shown in FIG. 12, a plurality of the container setting portions 612 may be provided, or a single container setting portion 612 may be provided.

The liquid reservoir 523 and the sample holding unit 524 are each sealed in an airtight manner by a cover 613. The cover 613 is provided with the liquid sending tube 526. By the liquid reservoir 523 being sealed by the cover 613, the liquid sending tube 526 is inserted into the container 611 containing a sample or a reagent. The liquid sending tube 526 provided to the cover 613 is connected to the sample processing chip 100 via the valve unit 522. The pressure in the liquid reservoir 523 sealed by the cover 613 is adjusted by the pump 521. If the pressure in the liquid reservoir 523 is increased to open the valve unit 522, the liquid in the container 611 is supplied to the sample processing chip 100 side.

The controller 530 determines the liquid reservoir 523 in which to hold liquids, and the types of the liquids to be held in the liquid reservoir 523, for example, and makes notification of the determined liquid reservoir 523 and the types of liquids to be held. The notification can be made by displaying the liquid reservoir 523 in which to hold the liquids and the kinds of the liquids to be held in the liquid reservoir 523, on the monitor 531 of the sample processing apparatus 500 or on a monitor (not shown) of a computer connected to the sample processing apparatus 500, for example. Accordingly, erroneous operation by a user can be inhibited.

Figure 13:
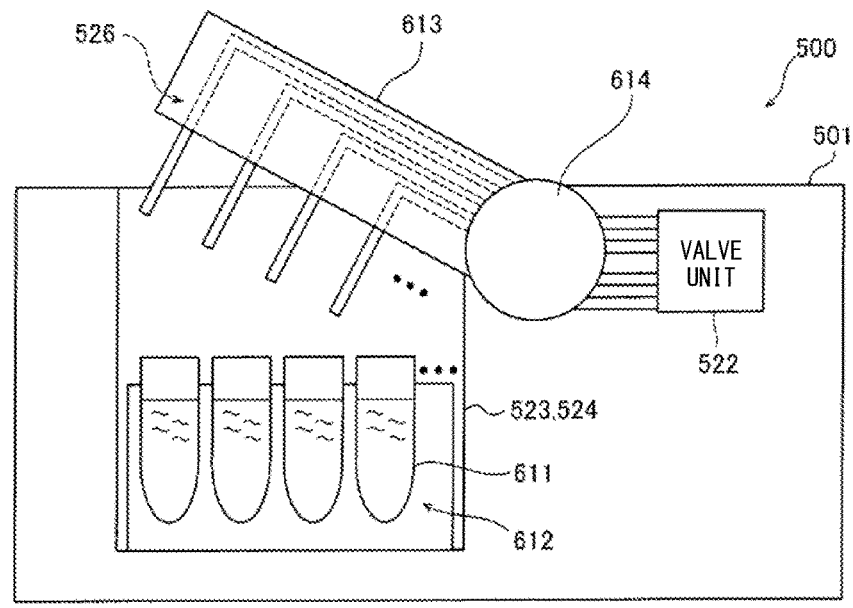
FIG. 13 is a vertical cross-sectional view showing a first configuration example of a cover for the liquid reservoir.
Figure 14:
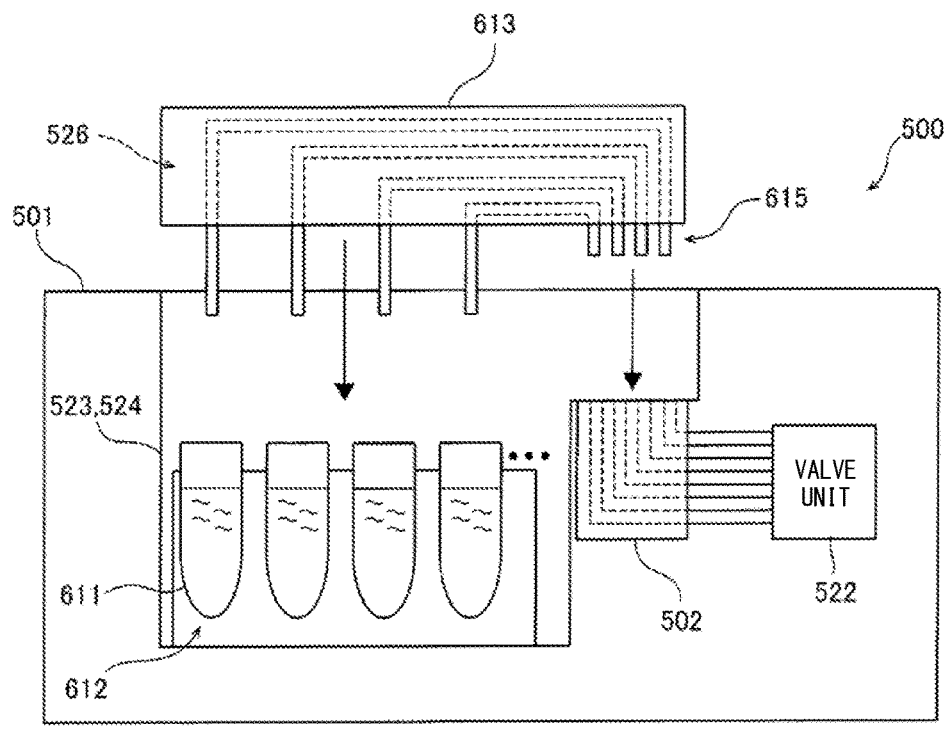
FIG. 14 is a vertical cross-sectional view showing a second configuration example of the cover for the liquid reservoir.

FIG. 13 and FIG. 14 each show a configuration example of the cover 613 for the liquid reservoir.

The cover 613 shown as an example in FIG. 13 is connected to a sample processing apparatus body 501 by a hinge 614. The cover 613 can be moved through rotation of the hinge 614, thereby to open/close the liquid reservoir 523 or the sample holding unit 524. The liquid sending tube 526 provided to the cover 613 is at least partially formed of a rubber tube or the like, and is deformable in accordance with opening/closing of the cover 613.

The cover 613 shown as an example in FIG. 14 is detachable from the sample processing apparatus body 501. When the cover 613 is attached to the sample processing apparatus body 501, a connector 615 of the cover 613 and a connector 502 on the sample processing apparatus 500 side are connected to each other, whereby the liquid sending tube 526 is connected between the cover 613 and valve unit 522.

Since the cover 613 is detachable from the sample processing apparatus 500, when liquid sending tube 526 is deteriorated due to dirt or the like, maintenance of the liquid sending tube 526 can be performed simply by replacing the cover 613.

(Configuration Example of Cover for Setting Portion)

Figure 15:
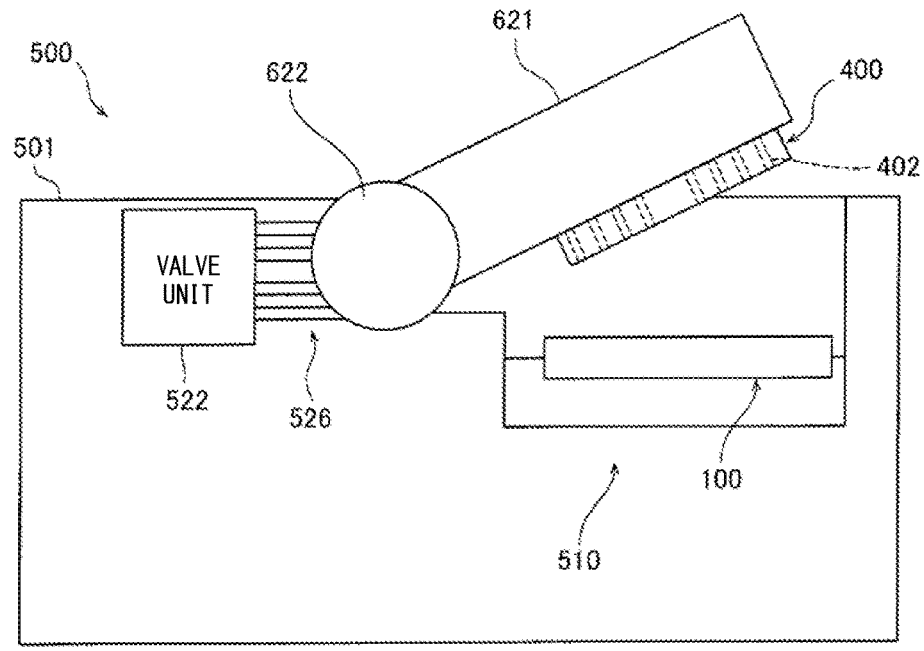
FIG. 15 is a vertical cross-sectional view showing a first configuration example of a cover for a setting portion.
Figure 16:
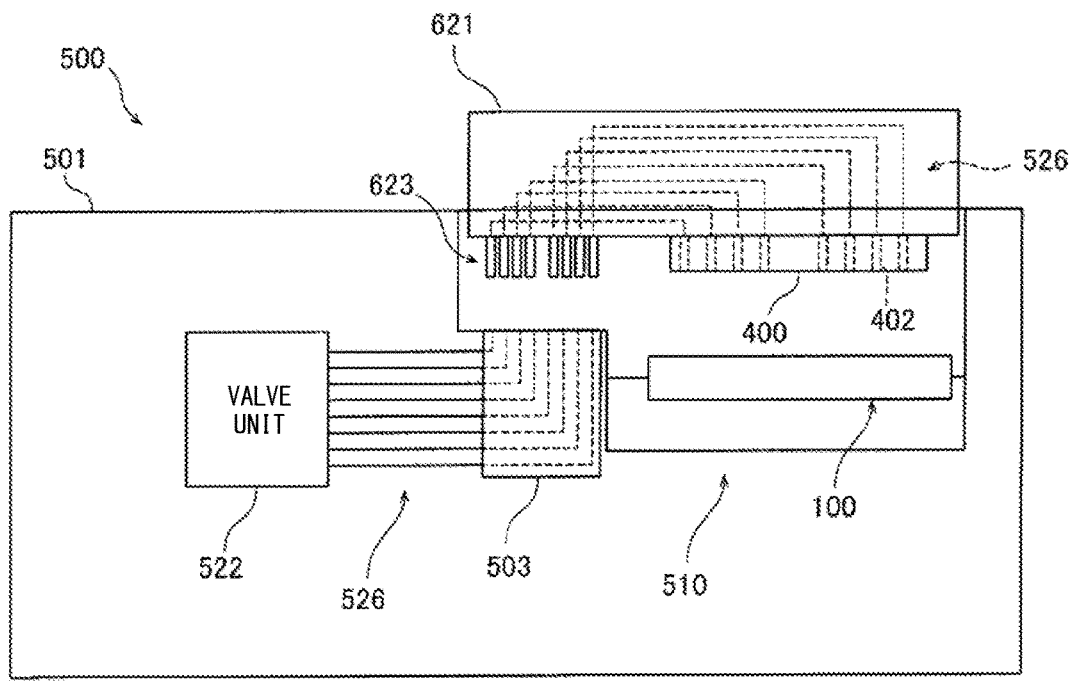
FIG. 16 is a vertical cross-sectional view showing a second configuration example of the cover for the setting portion.

The setting portion 510 may be provided with a cover 621 that corresponds to the setting portion 510. FIG. 15 and FIG. 16 each show a configuration example of the cover 621 for the setting portion 510. The cover 621 is provided so as to cover the sample processing chip 100 set to the setting portion 510.

The cover 621 shown as an example in FIG. 15 is connected to the sample processing apparatus body 501 by a hinge 622. The cover 621 is opened/closed through rotation of the hinge 622. The liquid sending tube 526 provided to the cover 621 is at least partially formed of a rubber tube or the like, and is deformable in accordance with opening/closing of the cover 621.

The cover 621 may include a connector 400 for supplying or collecting liquid, via ports provided at predetermined positions on the sample processing chip 100. Such a port is a through-hole 310 that functions as a port 101 for infusing a liquid or a reagent, for example, or a through-hole 310 that functions as a port 102 for liquid collection. The leading end of the liquid sending tube 526 extending from the valve unit 522 is connected to each hole 402 in the connector 400. Via the connector 400, liquid is transferred between the sample processing chip 100 and the liquid sending tube 526. Thus, simply by closing the cover 621 of the setting portion 510, the connector 400 and the sample processing chip 100 set to the setting portion 510 can be connected to each other.

The cover 621 shown as an example in FIG. 16 is detachable from the sample processing apparatus body 501.

When the cover 621 is attached to the sample processing apparatus body 501, a connector 623 of the cover 621 and a connector 503 of the sample processing apparatus 500 are connected to each other, whereby the liquid sending tube 526 is connected between the cover 621 and the valve unit 522. In addition, the connector 400 of the cover 621 is connected to ports of the sample processing chip 100. Via the connectors 503, 623, and 400, liquid is transferred between the sample processing chip 100 and the liquid sending tube 526.

As described above, if the cover 621 is configured to be detachable from the sample processing apparatus body 501, when the liquid sending tube 526 is deteriorated due to dirt or the like, maintenance of the liquid sending tube 526 can be performed simply by replacing the cover 621.

(Configuration Example of Connector)

Figure 17:
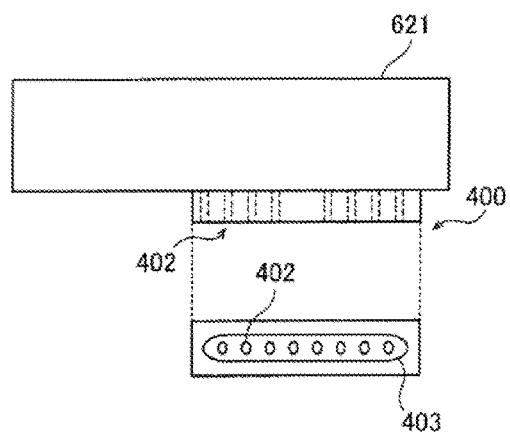
FIG. 17 is a vertical cross-sectional view showing a first configuration example of a connector.
Figure 18:
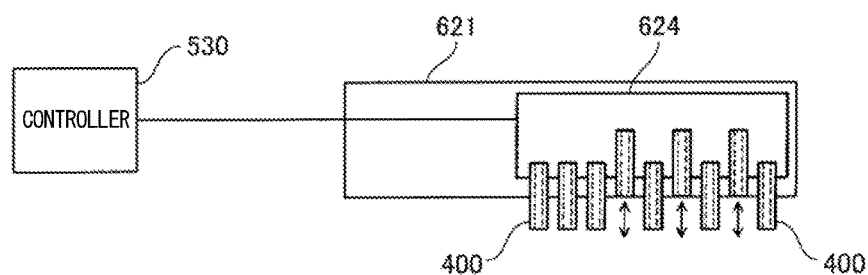
FIG. 18 is a vertical cross-sectional view showing a second configuration example of the connector.
Figure 19:
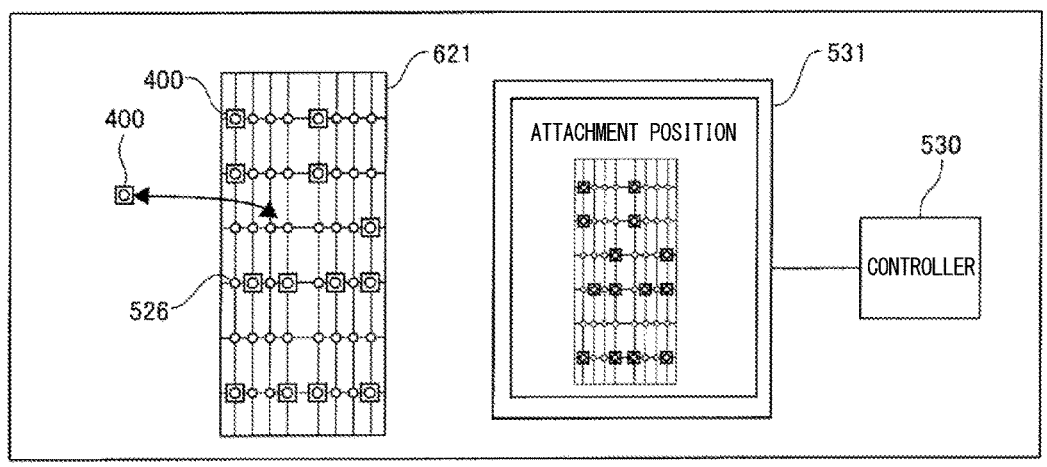
FIG. 19 is a schematic diagram showing a third configuration example of the connector.

FIG. 17 to FIG. 19 each shows a configuration example of the connector 400.

The connector 400 is provided to the cover 621. The connector 400 includes holes 402 for accessing through-holes 310 in the base plate 300. The connector 400 is set to a position that corresponds to the through-holes 310 in the base plate 300. The connector 400 may be set only at a position that corresponds to desired through-holes 310.

A liquid such as a sample or a reagent is infused via a hole 402 from the liquid sending tube 526 to the sample processing chip 100. Liquid flowing in the sample processing chip 100 is collected from the sample processing chip 100 via a hole 402. A desired through-hole 310 can be sealed by inserting a plug 401 (see FIG. 7, etc.) into a hole 402.

The connector 400 has a sealing member such as a gasket 403, on a face to be brought into contact with the sample processing chip 100. The gasket 403 inhibits liquid leakage and foreign matter contamination at ports 101 or between ports 102 and holes 402.

The through-hole 310 through which liquid is infused or collected by the connector 400 differs depending on the shape of the flow path provided to the sample processing chip 100. Thus, it is not necessary to provide the connector 400 for all the through-holes 310.

For example, the cover 621 may be able to hold the connector 400 inside the cover 621.

In the example shown in FIG. 18, the cover 621 includes: a plurality of the connectors 400; and a drive unit 624 that causes each of the plurality of the connectors 400 to advance/retract to/from the cover 621. Then, on the basis of the positions of the ports of the sample processing chip 100, the controller 530 determines the connectors 400 that are to be held inside the cover 621, and instructs the cover 621 to hold the determined connectors 400. When the connectors 400 designated by the controller 530 are protruding out of the cover 621, the drive unit 624 causes those connectors 400 to retract into the cover 621.

The connector 400 may be configured to be detachable from the cover 621. In the example of FIG. 19 showing the lower face of the cover 621, the cover 621 is configured such that a plurality of the connectors 400 is detachable therefrom. A user of the sample processing apparatus 500 can attach necessary connectors 400 at specific positions in the cover 621 in accordance with the positions of the ports of the sample processing chip 100. In this case, for example, the controller 530 makes notification of the positions at which to attach the connectors 400 on the basis of the positions of the ports of the sample processing chip 100. The notification can be made by, for example, displaying the positions at which to attach the connectors 400, on the monitor 531 of the sample processing apparatus 500 or on a monitor (not shown) of a computer connected to the sample processing apparatus 500. Thus, with this simple configuration, it is possible to connect only necessary connectors 400 to the sample processing chip 100 when using the sample processing chip 100, and it is possible to inhibit erroneous attachment of the connectors 400 performed by the user.

<Configuration Example of Fixture>

Figure 20:
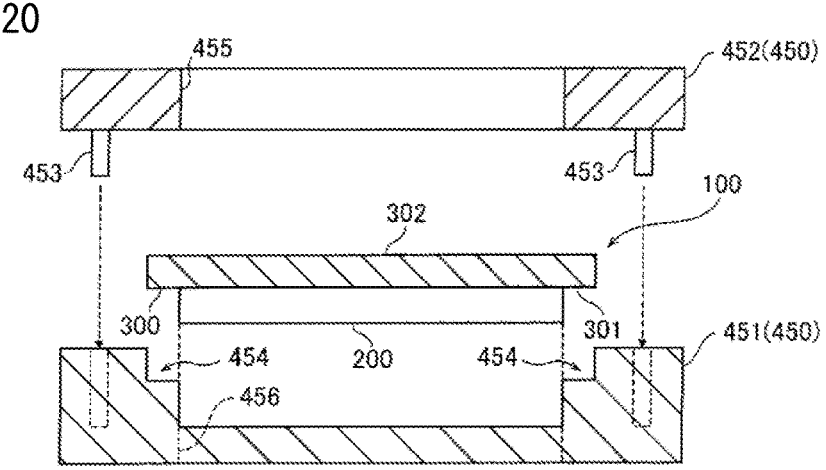
FIG. 20 is an exploded view showing a configuration example of a fixture.
Figure 21:
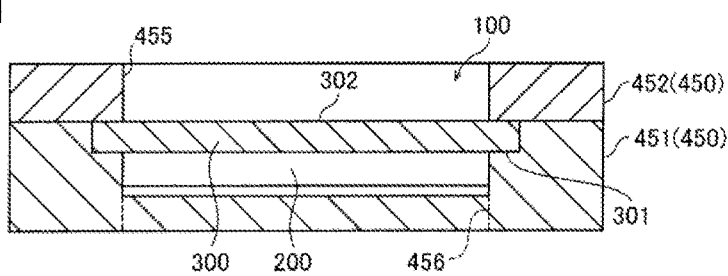
FIG. 21 shows the fixture in a state where the sample processing chip is fixed thereto.

FIG. 20 to FIG. 22 each show an example of the fixture 450 to be used for setting the sample processing chip 100 to the sample processing apparatus 500.

As shown in FIG. 20, the sample processing chip 100 is fixed by fixtures 451 and 452, for example. The fixture 451 and the fixture 452 are fixed together by fitting members 453. For example, the sample processing chip 100 is positioned in the horizontal direction by a positioning portion 454 formed in the fixture 451 on the lower side in FIG. 20. In the example shown in FIG. 20, the positioning portion 454 is formed as a step portion having a recessed shape. By the positioning portion 454, the relative position between the sample processing chip 100 and the fixtures 451 and 452 is determined.

FIG. 21 shows a side view of the sample processing chip 100 in a state of being fixed by the fixtures 451 and 452. The sample processing chip 100 in which the fluid module 200 is joined to the base plate 300 is fixed by the fixtures as shown in FIG. 21.

Figure 22A:
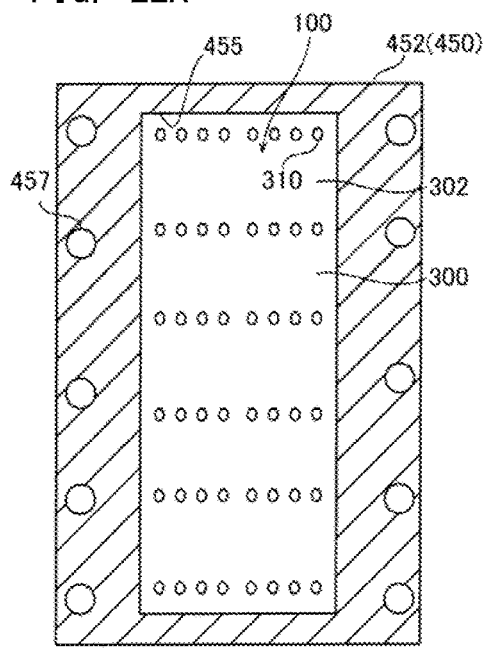
FIG. 22A shows a second face side of the sample processing chip shown in FIG. 21.
Figure 22B:
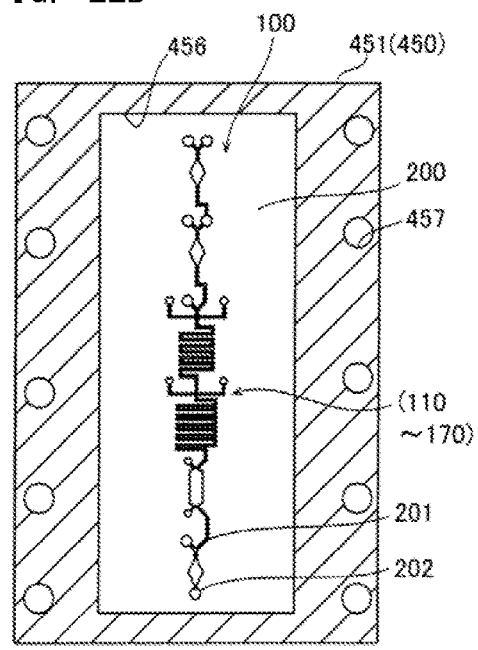
FIG. 22B shows a first face side of the sample processing chip shown in FIG. 21.

As shown in FIG. 22A, the fixture 452 has an opening 455, which is a through-hole, at a position that corresponds to the base plate 300. The connectors 400 and the like of the sample processing apparatus 500 can access the base plate 300 from the second face 302 side via the opening 455. Furthermore, as shown in FIG. 22B, the fixture 451 has an opening 456, which is a through-hole, at a position that corresponds to the base plate 300 and the fluid module 200, thereby allowing access from the first face 301 side to the base plate 300 and the fluid module 200 via the opening 456.

If the sample processing chip 100 held by the fixtures 451 and 452 is set to the setting portion 510, or if the sample processing chip 100 is set to the fixture 451 fixed to the setting portion 510 and the fixture 452 is mounted thereto, the sample processing chip 100 is set to the setting portion 510. It may be configured such that: the fixture 452 is fixed to the cover 621 of the setting portion 510; and the fixture 452 is mounted to the fixture 451 at the same time when the cover 621 is set.

As shown in FIG. 22, the fixtures 451 and 452 may have mounting holes 457 for disposing various kinds of processing units that are provided to the sample processing apparatus 500. In the example shown in FIG. 22, a plurality of the mounting holes 457 are provided outside the opening 455 and along the long side of the fixture 452 (451).

(Setting Example of Various Kinds of Units)

Figure 23:
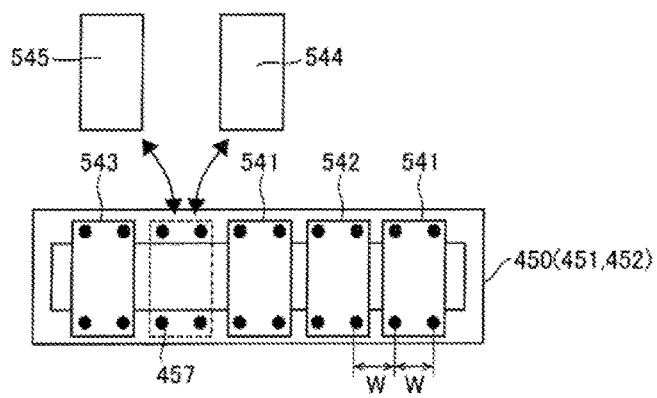
FIG. 23 is a schematic diagram showing a setting example of various kinds of units.

FIG. 23 shows a setting example of processing units to be used in various kinds of process steps performed in the sample processing apparatus 500.

As shown in FIG. 23, for example, a heater unit 541 for heating liquid in the fluid module 200, a magnet unit 542 for causing magnetic force to act on the liquid in the fluid module 200, a cooling unit 543 for cooling the liquid in the fluid module 200, a detection unit 544 for detecting the target component in the sample processing chip 100, a camera unit 545 for taking images of the flow of the liquid in the fluid module 200, and the like are mounted to the fixture 451 or 452, via the mounting holes 457. The connector 400 may be mounted to the fixture 451 or 452. Processing units may be a composite unit having a plurality of functions among these functions. For example, a processing unit may be used that has a function of heating liquid and a function of causing magnetic force to be acted on liquid.

Simply by mounting these processing units and the sample processing chip 100 to the fixtures 451 and 452, it is possible to easily perform relative positioning between the processing units and the sample processing chip 100, via the fixture 451 (452).

A plurality of the mounting holes 457 are provided at a predetermined pitch W, for example. Accordingly, even in a case where the sample processing chip 100 is used that has different arrangement and shapes of flow paths formed in the fluid module 200, the position of each processing unit can be freely changed by the units of pitch W in accordance with the flow path structure. The pitch W may be the same as the pitch H of the through-holes 310 in the base plate 300, or an integer multiple of the pitch H, for example. In that case, the position of each flow path in the fluid module 200 and the position of each processing unit can be easily aligned to each other.

<Heating Portion (Heater Unit)>

FIG. 24 shows an arrangement example of the heater unit 541 and the heating portion 560 in the sample processing apparatus 500.

The heater unit 541 adjusts the temperature of the sample processing chip 100. The heating portion 560 for heating the storage portion 173 is configured by the heater unit 541. The heater unit 541 may be provided as a heating portion other than the heating portion 560 for heating the storage portion 173. For example, the heater unit 541 heats the sample processing chip 100 in order to amplify DNA by PCR in the fluid module 200. More specifically, the heater unit 541 forms a plurality of temperature zones TZ1, TZ2, and TZ3 (see FIG. 48) in the second flow path 120 of the sample processing chip 100. If the heater unit 541 forms the plurality of temperature zones TZ1, TZ2, and TZ3, a thermal cycle process is enabled, simply by causing the liquid flowing in the second flow path 120 to pass through the temperature zones TZ1 to TZ3. At this time, it is sufficient to cause the temperature zones TZ1 to TZ3 to keep different constant temperatures, respectively. Therefore, compared with a case where a thermal cycle process is performed by cyclically varying the temperature of the entirety of the heater unit 541, temperature control is facilitated.

Figure 24A:
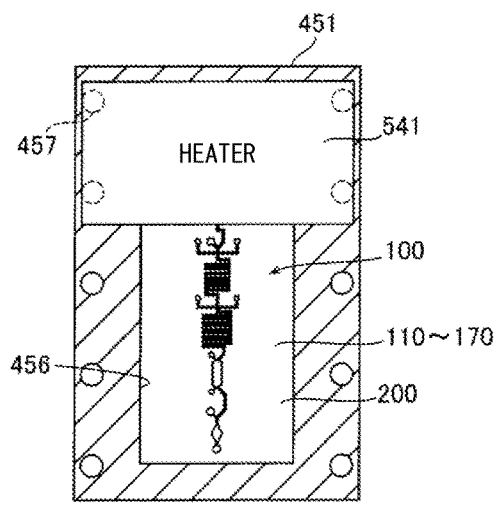
FIG. 24A shows an arrangement example of a heater unit at the fixture.
Figure 24B:
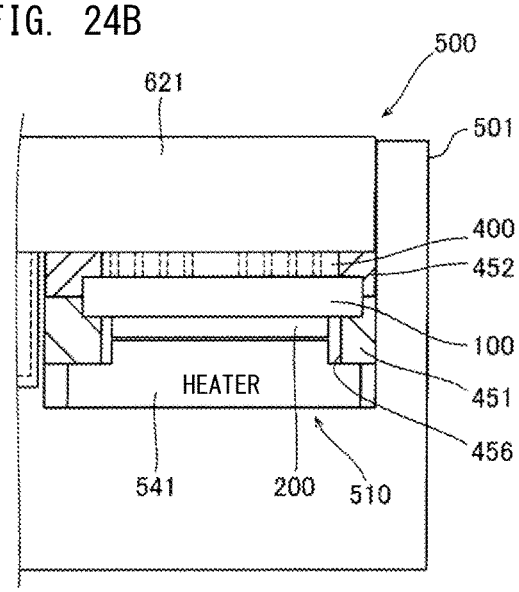
FIG. 24B is a schematic cross-sectional view showing an arrangement example of the heater unit in the setting portion.

As shown in FIGS. 24A and 24B, the heater unit 541 is provided in the setting portion 510. For example, the heater unit 541 is mounted to the fixture 451 on the first face 301 side where the fluid module 200 of the sample processing chip 100 is set. The heater unit 541 adjusts the temperature of the sample processing chip 100, from the first face 301 side of the sample processing chip 100 set in the setting portion 510. The heater unit 541 is disposed at a position that corresponds to the flow path to be subjected to temperature adjustment.

The heater unit 541 may be movable. The controller 530 of the sample processing apparatus 500 causes the heater unit 541 to be moved such that the heater unit 541 is disposed at a position that corresponds to the flow path to be subjected to temperature adjustment among the fluid modules 200 mounted to the sample processing chip 100.

Figure 24C:
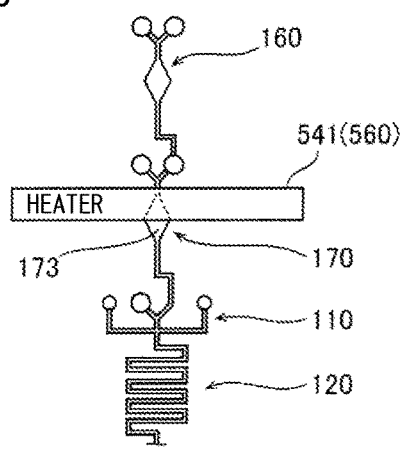
FIG. 24C is a schematic diagram showing an arrangement example of the heating portion (heater unit) relative to a dilution flow path.
Figure 35:
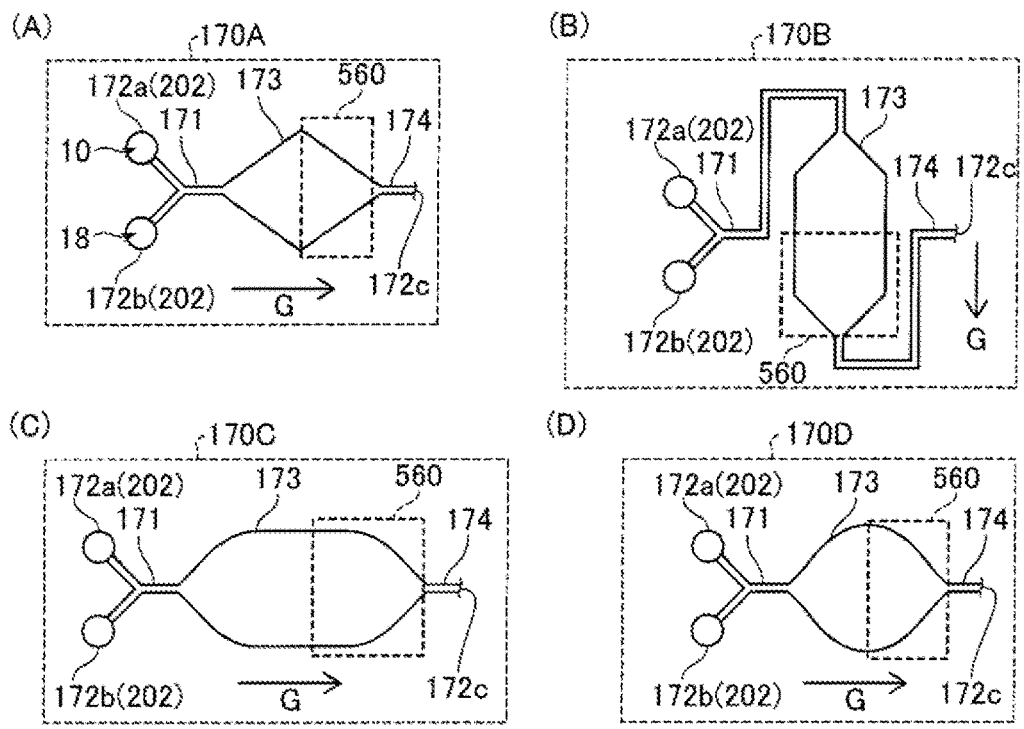
FIG. 35 shows arrangement examples (A), (B), (C), and (D) of the heating portion relative to the dilution flow path.

As shown in FIG. 24C, the heater unit 541 forming the heating portion 560 may have a size that allows the heater unit 541 to be disposed at a position that corresponds to the region of a part of the storage portion 173 of the dilution flow path 170. By partially heating the storage portion 173 of the sample processing chip 100, the heating portion 560 forms temperature distribution for causing thermal convection in the storage portion 173. Due to the temperature distribution, thermal convection occurs in the storage portion 173. The target component in the sample and the diluent 18 stored in the storage portion 173 are mixed together through the thermal convection. As shown in FIG. 35 described later, the heating portion 560 can heat the region of a part of the storage portion 173. By partially heating the storage portion 173, it is possible to efficiently cause thermal convection in the storage portion 173, without increasing the size of the heating portion 560.

<Detection Unit>

Figure 25A:
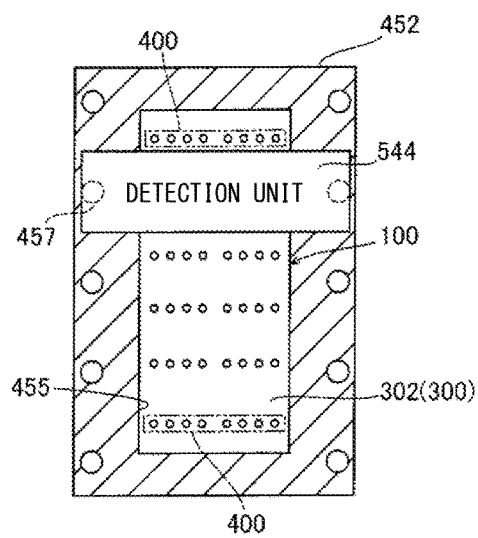
FIG. 25A shows an arrangement example of a detection unit at the fixture.
Figure 25B:
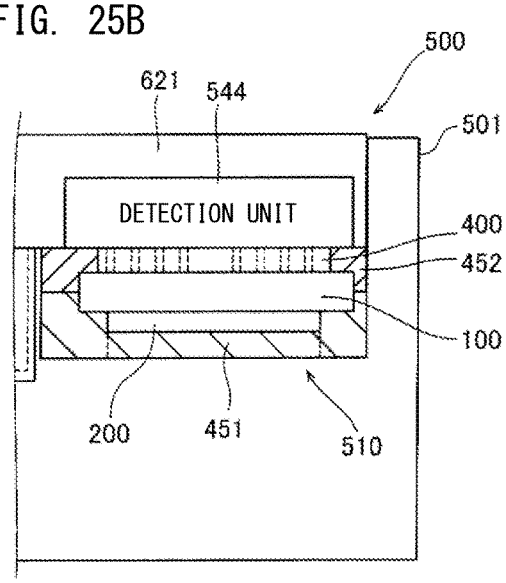
FIG. 25B is a schematic cross-sectional view showing an arrangement example of the detection unit in the setting portion.

FIG. 25 shows a configuration example of the detection unit 544 of the sample processing apparatus 500.

The detection unit 544 detects fluorescence of a labeled substance bound to the nucleic acid, for example. The detection unit 544 is a photomultiplier, for example. The detection unit 544 is mounted to the fixture 452 on the second face 302 side of the sample processing chip 100, for example. The detection unit 544 may be provided to the cover 621. The detection unit 544 detects fluorescence through the connector 400 connected to the sample processing chip 100. The detection unit 544 may be provided to the sample processing apparatus body 501, or the fixture 451 on the first face 301 side of the sample processing chip 100. In this case, the detection unit 544 detects fluorescence from the first face 301 side of the sample processing chip 100.

<Magnet Unit>

Figure 26A:
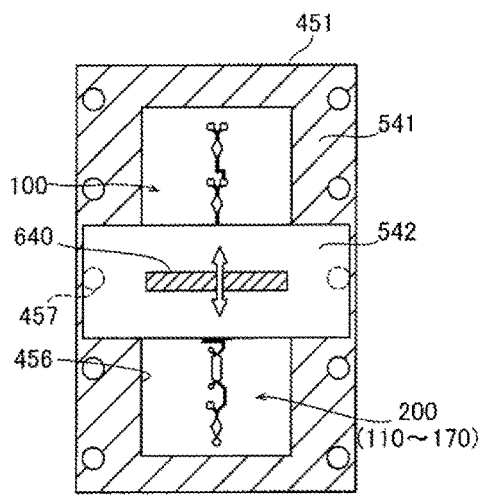
FIG. 26A shows an arrangement example of a magnet unit at the fixture.
Figure 26B:
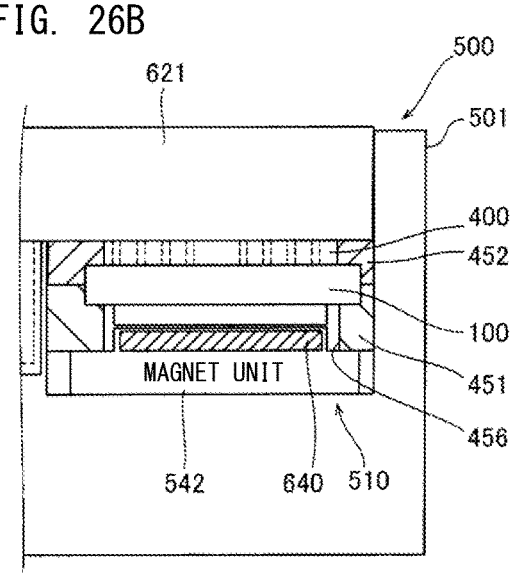
FIG. 26B is a schematic cross-sectional view showing an arrangement example of the magnet unit in the setting portion.

FIG. 26 shows a configuration example of the magnet unit 542 to be used in control of magnetic particles contained in the liquid in the sample processing chip 100. When magnetic particles are used as the carrier 13, the magnet unit 542 performs a process of collecting the carrier 13 by causing magnetic force to act on the magnetic particles. Accordingly, even in a fine flow path or a well provided to the sample processing chip 100, the carrier 13 in the liquid can be easily collected by magnetic force.

The magnet unit 542 is mounted to the fixture 451 on the first face 301 side of the sample processing chip 100, for example. The magnet unit 542 may be provided to the sample processing apparatus body 501. The magnet unit 542 includes a magnet 640. The magnet 640 applies magnetic force to the magnetic particles contained in the liquid in the sample processing chip 100. For example, the magnet 640 fixes, by magnetic force, magnetic particles at a predetermined position in a flow path of the fluid module 200. By causing a washing liquid to flow to the magnetic particles fixed at the predetermined position, the magnetic particles are washed. The magnet unit 542 can move the magnet 640 in the longitudinal direction of the sample processing chip 100, for example.

Although not shown, the same applies to the camera unit 545 and the cooling unit 543.

(Operation of Sample Processing Apparatus)

With reference to the flow charts shown in FIG. 27 to FIG. 29, examples of operation performed by the sample processing apparatus 500 will be described.

<Opening/Closing Control of Valve Unit>

Figure 27:
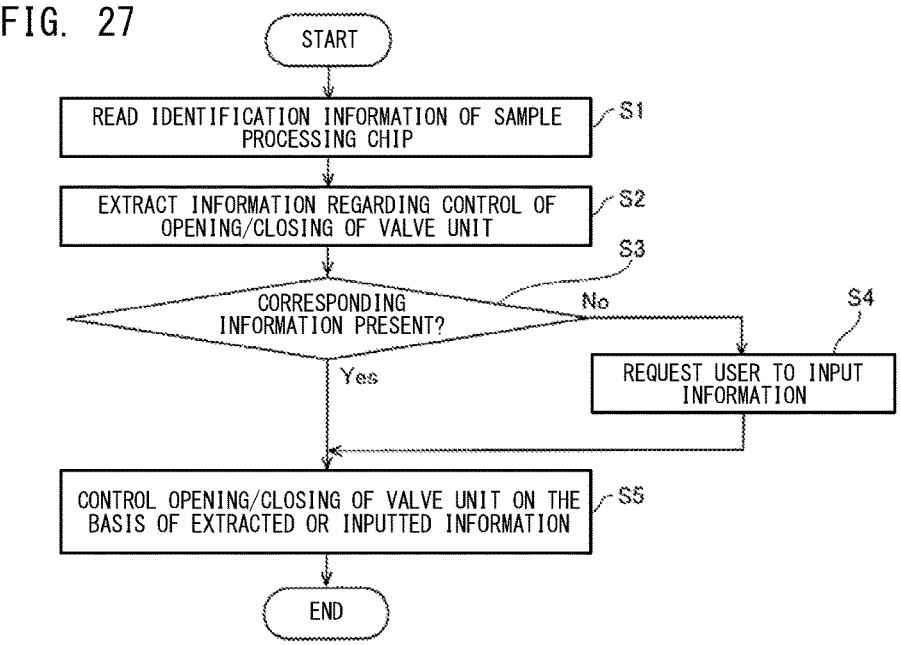
FIG. 27 is a flow chart showing one example of opening/closing control of valve units performed by a controller.

In step S1 in FIG. 27, the sample processing apparatus 500 reads identification information given to the sample processing chip 100. The identification information is given in the form of a bar code or a QR code (registered trademark), for example, and the sample processing apparatus 500 reads the identification information by means of the reading unit 533. The read information is sent to the controller 530.

For example, the identification information includes information determined in accordance with the combination of flow paths in the sample processing chip 100 and the flow path structure such as arrangement of the connection portions 202. The identification information may include information of other elements (for example, the type of assay, etc.) in addition to the flow path structure of the sample processing chip 100. The identification information may include information indicated below, for example.

ID and position information of each through-hole 310 into which liquid is to be infused.

ID and position information of each through-hole 310 from which liquid is to be collected.

Information indicating the order of infusion or collection of liquid (The order is expressed by the arrangement order of IDs of the above through-holes 310, for example).

Information indicating the timing of infusion or collection of liquid (The timing is expressed by the elapsed time from the start of infusion of liquid or by the infused amount of liquid, for example. The timing is set for ID of each through-hole 310 into which liquid is to be infused).

ID of liquid (reagent or the like) to be used in the test.

Information indicating the position at which to store liquid to be used in the test.

(The storage position is expressed by the number or the like representing the liquid reservoir 523 in which to store the liquid, for example).

In step S2, the controller 530 extracts information regarding opening/closing of valve units from the read identification information. For example, the controller 530 extracts the ID and the position information of each through-hole 310 that is relevant to infusion or collection of liquid.

In step S3, the controller 530 determines the presence/absence of corresponding information. If the information regarding opening/closing of valve units is not included in the identification information, the controller 530 advances the process to step S4. In this case, in step S4, the controller 530 displays a content that urges input of information regarding opening/closing of valve units, on the monitor 531 of the sample processing apparatus 500 or on a monitor (not shown) of a computer connected to the sample processing apparatus 500.

If the information regarding opening/closing of valve units is included in the identification information in step S3, the controller 530 advances the process to step S5. In step S5, on the basis of the identification information read from the sample processing chip 100 by the reading unit 533, the controller 530 controls opening/closing of each valve unit 522 in the liquid sending portion 520. If the information regarding opening/closing of valve units has been received via the input unit 532, the controller 530 controls opening/closing of each valve unit 522 in the liquid sending portion 520 on the basis of the inputted identification information.

The controller 530 controls opening/closing of the valve unit 522 that corresponds to the position of each through-hole 310 that is relevant to infusion or collection of liquid. The controller 530 controls the valve unit 522 that corresponds to the position of each through-hole 310 that is not relevant to infusion or collection of liquid, such that the valve unit 522 is always closed during the test.

As described above, by configuring the controller 530 such that the controller 530 controls opening/closing of valve units 522 on the basis of identification information indicating the flow path structure of the fluid module 200, even when the through-holes 310 through which liquid is infused or collected differ depending on the flow path structure of the fluid module 200, it is not necessary to individually designate valve units 522 for which to perform opening/closing control, every time the user uses the sample processing chip 100.

Further, by configuring the controller 530 such that the controller 530 controls opening/closing of valve units 522 on the basis of the identification information inputted through the input unit 532, it becomes possible to determine valve units 522 for which to perform opening/closing control, simply by the user inputting identification information when using the sample processing chip 100.

Further, by configuring the controller 530 such that the controller 530 controls opening/closing of valve units 522 on the basis of the identification information read from the sample processing chip 100 by the reading unit 533, it is not necessary to input the identification information when the sample processing chip 100 is to be used. This eliminates the need of preparation work for opening/closing of valve units 522, whereby convenience of the sample processing apparatus 500 is improved.

<Control of Opening/Closing Timing of Valve Unit>

Figure 28:
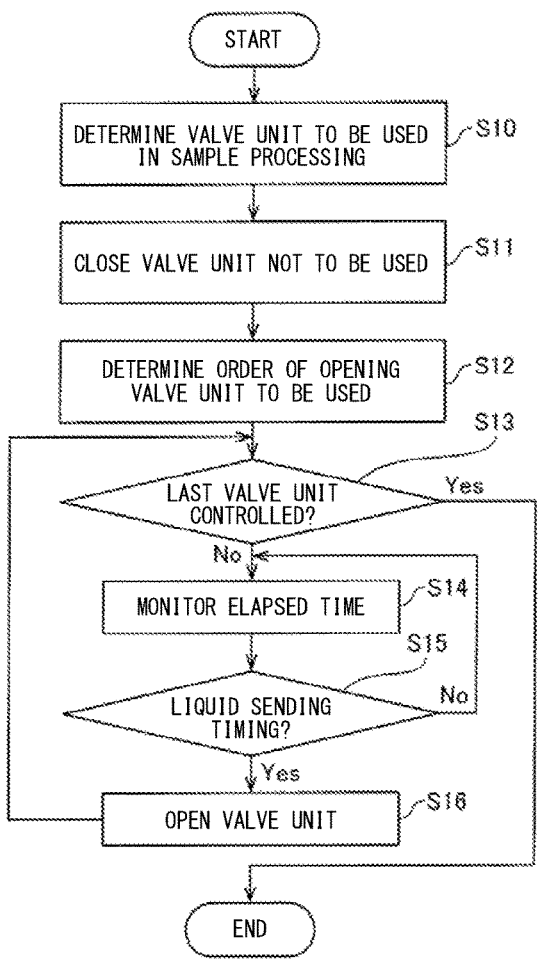
FIG. 28 is a flow chart showing one example of control of opening/closing timing of valve units performed by the controller.

FIG. 28 shows an example of operation performed when the controller 530 controls the timing of opening a valve unit 522.

In step S10, the controller 530 determines valve units 522 to be used in sample processing, on the basis of the flow path structure of the fluid module 200. For example, in accordance with the operation described in FIG. 27, the controller 530 determines, on the basis of the flow path structure of the fluid module 200, the positions of the ports 101 provided on the sample processing chip 100 for infusing liquid into the fluid module 200. That is, the controller 530 determines through-holes 310 that function as ports 101 for infusing liquid. On the basis of the determined positions of the ports 101, the controller 530 controls opening/closing of each valve unit 522 in the liquid sending portion 520.

In step S11, the controller 530 closes valve units 522 that are not to be used. In step S12, the controller 530 determines the order of opening valve units 522 that are to be used in the sample processing. On the basis of the information contained in the above-described identification information (information indicating the order of infusion or collection of liquid), for example, the controller 530 determines the order of opening the valve units 522.

In step S13, the controller 530 determines whether control of the last valve unit 522 in the determined order has been completed. If the control of the last valve unit 522 has not been completed, then, in step S14, the controller 530 monitors the elapsed time from the start of liquid infusion into the sample processing chip 100. For example, the controller 530 monitors the elapsed time from the time point at which the first valve unit 522 in the order was opened.

In step S15, the controller 530 determines whether the timing has come at which to send liquid to the sample processing chip 100. If the timing has come at which to send liquid to the sample processing chip 100, then, in step S16, the controller 530 opens the corresponding valve unit 522. For example, on the basis of whether the above-described elapsed time has reached the timing extracted from the identification information, the controller 530 determines whether the timing at which to send liquid has come. If the elapsed time has not reached the timing at which to send liquid, the controller 530 returns the process to step S14, and monitors the elapsed time.

The controller 530 repeats the operations of step S14 to S16 until performing those operations on all the valve units 522 determined as to be used in the sample processing. If the control of the last valve unit 522 has been completed, the controller 530 ends the process.

<Process of Storing Liquid into Liquid Reservoir>

Figure 29:
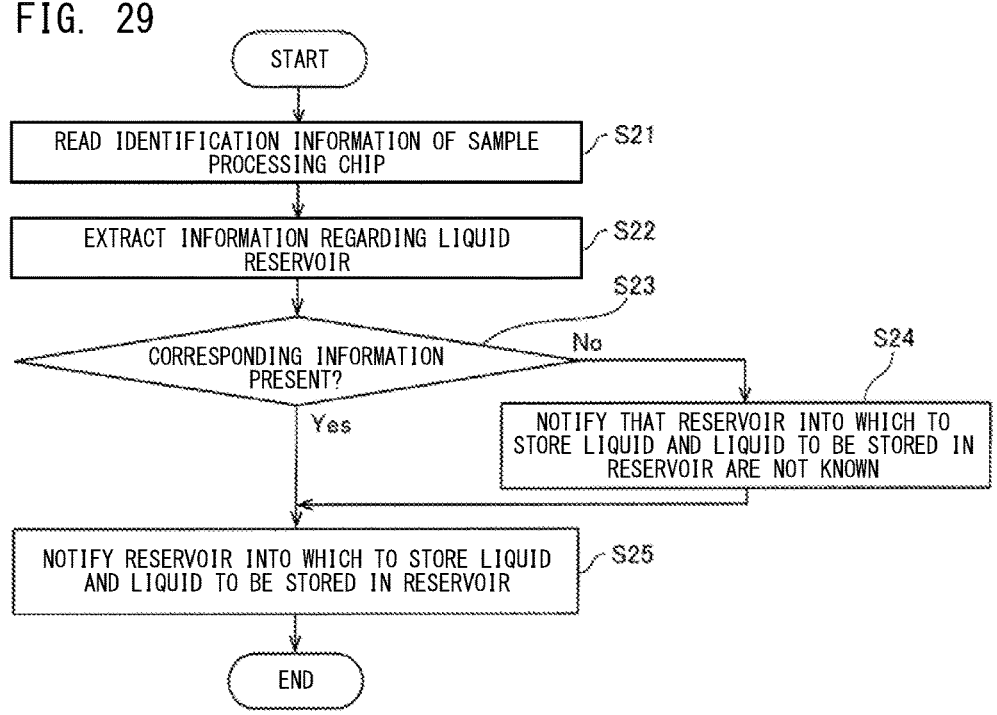
FIG. 29 is a flow chart showing one example of a process of storing liquid into the liquid reservoir performed by the controller.

FIG. 29 shows an example of operation performed when liquid to be used in the test is to be stored in the liquid reservoir.

Step S21 is the same operation as that of step S1 shown in FIG. 27.

In step S22, the controller 530 extracts the information regarding liquid reservoirs 523 from the read identification information. For example, the controller 530 extracts information indicating liquids (reagent and the like) to be used in the test and information indicating the positions at which to store the liquids to be used in the test.

In step S23, the controller 530 determines the presence/absence of corresponding information. If the information regarding liquid reservoirs 523 is not included in the identification information, then, in step S24, the controller 530 displays on the monitor 531 an indication that liquid reservoirs 523 into which to store liquids, and liquids to be stored in the liquid reservoirs 523 are not known. The display may be provided on a monitor (not shown) of a computer connected to the sample processing apparatus 500.

If the relevant information is included in the identification information, then, in step S25, on the basis of the extracted information, the controller 530 displays on the monitor 531 the liquid reservoirs 523 into which to store the liquids and the types of the liquids to be stored in the liquid reservoirs 523. By the liquid reservoirs 523 and the types of the liquids being displayed, erroneous operation by the user is inhibited. The display may be provided on a monitor (not shown) of a computer connected to the sample processing apparatus 500.

[Configuration Example of Sample Processing Chip]

Next, a specific configuration example of the sample processing chip 100 will be described. An example will be described in which an emulsion PCR assay is performed by use of the sample processing chip 100 described above.

<Description of Emulsion PCR Assay>

Figure 30:
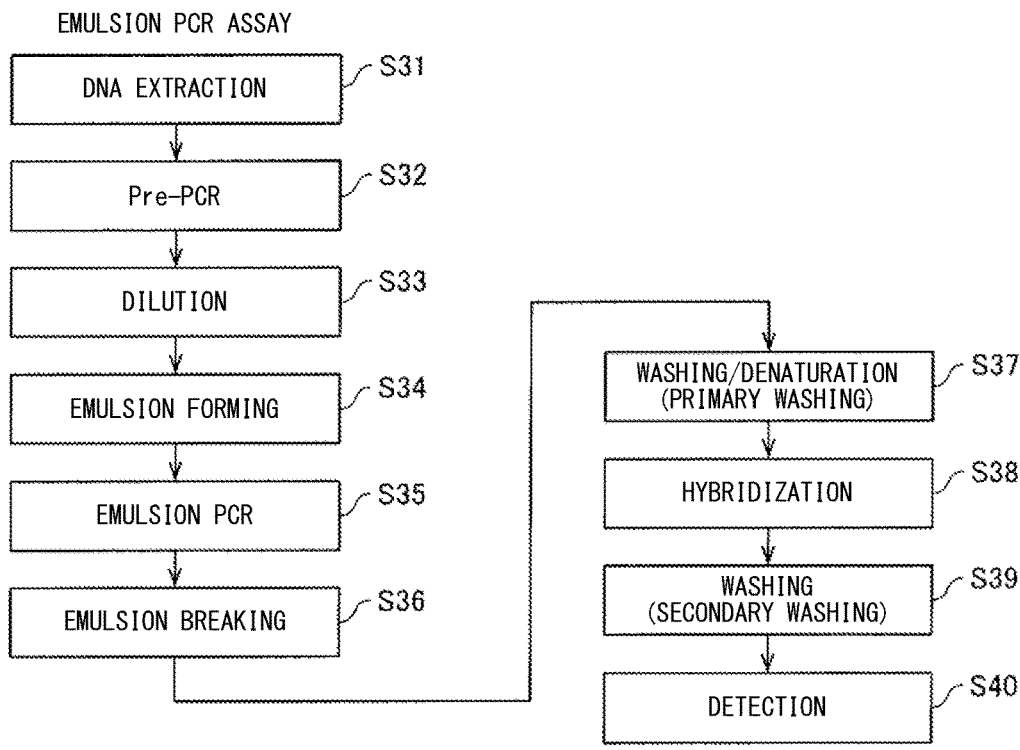
FIG. 30 is a flow chart showing one example of an emulsion PCR assay.
Figure 31:
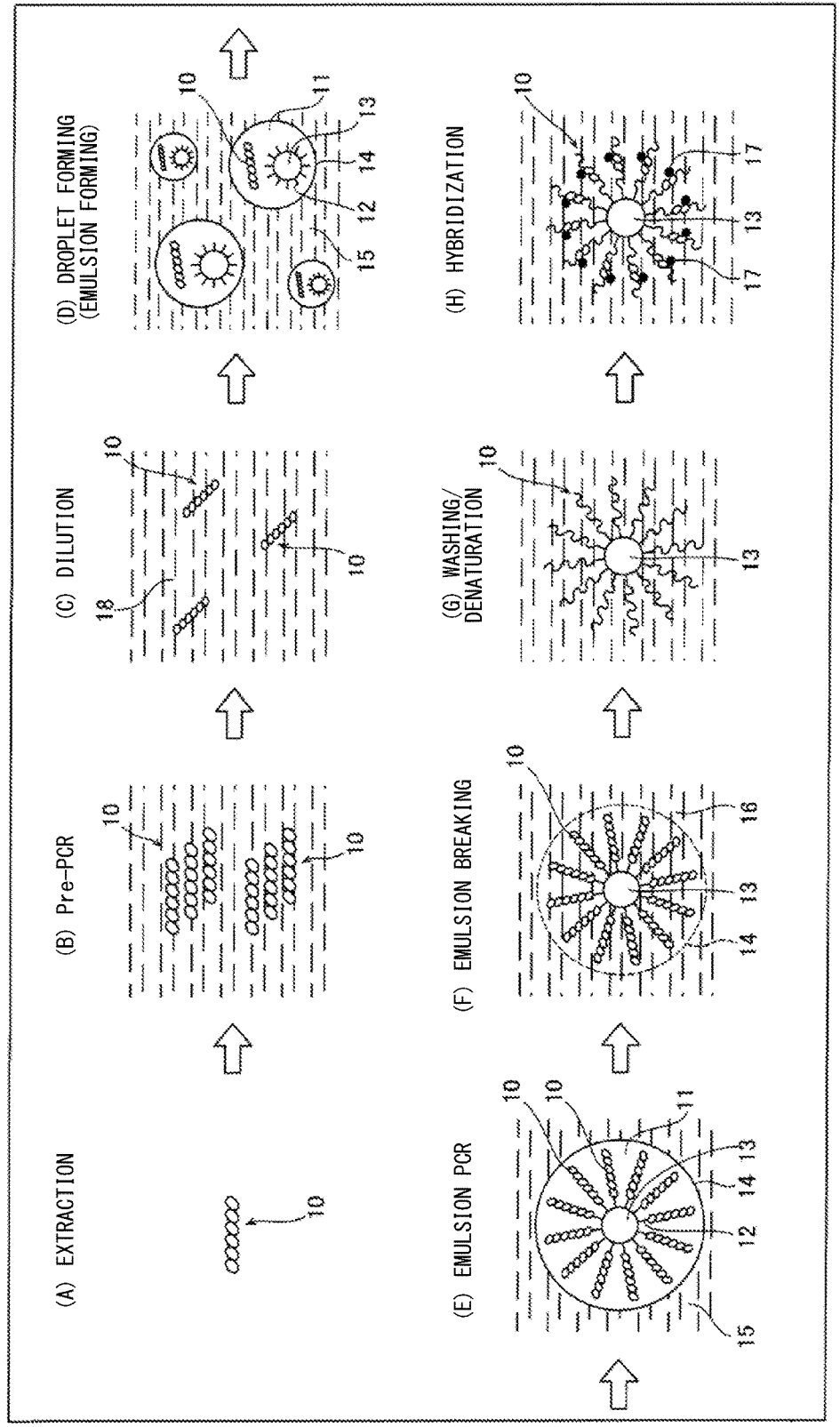
FIG. 31 illustrates how the process proceeds in an emulsion PCR assay.

FIG. 30 shows an example of a flow of an emulsion PCR assay. FIG. 31 illustrates how the process proceeds in an emulsion PCR assay. Here, it is assumed that the target component 10 is nucleic acid DNA and the carrier 13 is magnetic particles.

In step S31, DNA is extracted from a specimen such as blood, through pretreatment (see (A) of FIG. 31). For the pretreatment, a dedicated nucleic acid extracting device may be used, or a pretreatment mechanism may be provided to the sample processing apparatus 500.

In step S32, the extracted DNA is amplified by Pre-PCR processing (see (B) of FIG. 31). The Pre-PCR processing is a process of preliminarily amplifying DNA contained in the extract obtained through pretreatment, to an extent that allows a successive emulsion forming process to be performed. In the Pre-PCR processing, the extracted DNA, and a PCR amplification reagent which contains a primer and a polymerase are mixed together, and DNA in the mixture is amplified through temperature control by a thermal cycler. The thermal cycler performs a process of repeating, a plurality of times, one cycle in which the temperature of the mixture is changed to a plurality of different temperatures. In order to stabilize the number of DNA molecules after amplification, it is preferable to amplify DNA to a number sufficiently greater than the number required in the emulsion forming process. Thus, DNA amplified through the Pre-PCR processing is diluted to a predetermined rate through a dilution process.

In step S33, DNA is diluted with a diluent (see (C) of FIG. 31). The dilution process in step S33 is performed between the process of (B) of FIG. 31 and the emulsion forming process in (D) of FIG. 31. DNA is diluted at a dilution rate of about 1000 fold to several hundred thousand fold, for example. Through the dilution process, DNA amplified through the Pre-PCR processing is diluted so as to have a predetermined concentration (the number of DNA molecules per unit volume of the mixture) that is required in the emulsion forming process.

In step S34, an emulsion is formed which includes DNA and the reagent 11 for amplification reaction and containing magnetic particles (see (D) of FIG. 31). That is, droplets 14 are formed which contain the mixture of DNA and the reagent 11 containing the magnetic particle, the polymerase, and the like, and a large number of the droplets 14 are dispersed in the dispersion medium 15. The magnetic particle encapsulated in the droplet 14 is provided, at the surface thereof, with the primer 12 for nucleic acid amplification. Each droplet 14 is formed so as to include about one magnetic particle and about one target DNA molecule. The dispersion medium 15 is non-miscible with the mixture. In this example, the mixture is water-based, and the dispersion medium is oil-based. The dispersion medium 15 is an oil, for example.

In step S35, through the temperature control by the thermal cycler, in each droplet 14 in the emulsion, DNA binds to the primer 12 on the magnetic particle to be amplified (emulsion PCR) (see (E) of FIG. 31). Accordingly, in each individual droplet 14, the target DNA molecule is amplified.

After DNA has been amplified on the magnetic particle, then, in step S36, the emulsion is broken and magnetic particles including the amplified DNA are taken out of the droplets 14 (emulsion breaking) (see (F) of FIG. 31). As a reagent 16 for breaking the droplets 14, one or a plurality of kinds of reagents 16 including alcohol, surfactant, and the like are used.

In step S37, the magnetic particles taken out of the droplets 14 are washed in a BF separation step (primary washing). The BF separation step is a process step in which the magnetic particles including the amplified DNA are caused to pass through a washing liquid in a state where the magnetic particles are collected by magnetic force, such that unnecessary substances attached to the magnetic particles are removed. In the primary washing step, a washing liquid containing alcohol is used, for example. The alcohol removes the oil film on the magnetic particle, and denatures the amplified double-stranded DNA into single strands (see (G) of FIG. 31).

After the washing, in step S38, the DNA denatured into single strands on the magnetic particle is caused to bind to a labeled substance 17 for detection (hybridization) (see (H) of FIG. 31). The labeled substance 17 is a substance that emits fluorescence, for example. The labeled substance 17 is designed so as to specifically bind to the detection target DNA.

In step S39, the magnetic particle bound to the labeled substance 17 is washed in another BF separation step (secondary washing). The secondary BF separation step is performed through a process similar to that of the primary BF separation step. In the secondary washing step, PBS (phosphate buffered saline) is used as the washing liquid, for example. PBS removes unreacted labeled substance that did not bind to DNA (including labeled substance non-specifically attached to the magnetic particles).

In step S40, DNA is detected via the hybridized labeled substance 17. For example, DNA is detected by a flow cytometer. In the flow cytometer, the magnetic particle including DNA bound to the labeled substance 17 is caused to flow in a flow cell, and is irradiated with laser light. Fluorescence emitted from the labeled substance 17 irradiated with the laser light is detected.

DNA may be detected through image processing. For example, the magnetic particles including DNA bound to the labeled substance 17 are dispersed on a flat slide or in a flow path, and an image of the dispersed magnetic particles is taken by a camera unit. On the basis of the taken image, the number of the magnetic particles emitting fluorescence is counted.

(Example of Flow Path Configuration of Sample Processing Chip)

Figure 32:
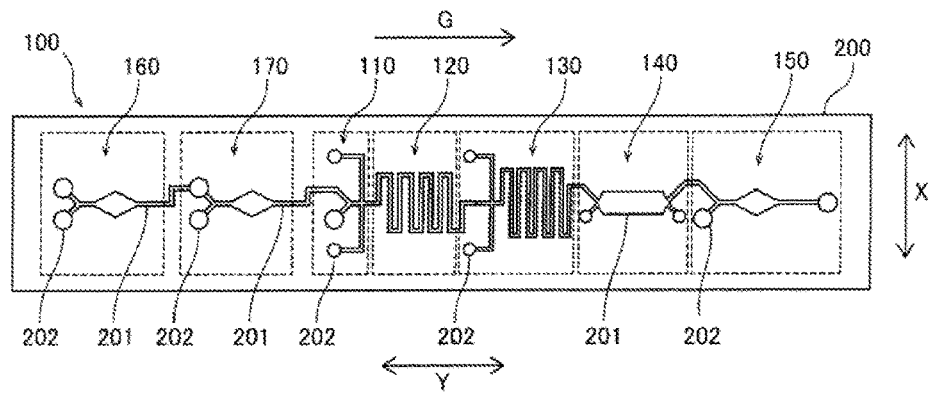
FIG. 32 shows a configuration example of the sample processing chip to be used in the emulsion PCR assay.

FIG. 32 shows an example of a flow path configuration of the sample processing chip 100 to be used in the emulsion PCR assay.

The sample processing chip 100 shown in FIG. 32 is configured by the fluid module 200 having a plurality of kinds of functions. The plurality of kinds of functions of the fluid module corresponds to the configuration of the flow paths formed in the fluid module 200. In the example shown in FIG. 32, the fluid module 200 includes the dilution flow path 170 and the droplet forming flow path 110. In the example shown in FIG. 32, the fluid module 200 further includes the first flow path 160, the second flow path 120, the third flow path 130, the fourth flow path 140, and the fifth flow path 150. In the example shown in FIG. 32, the flow paths are connected to one another in series, from the flow-in side of the liquid containing DNA, in the order of the first flow path 160, the dilution flow path 170, the droplet forming flow path 110, the second flow path 120, the third flow path 130, the fourth flow path 140, and the fifth flow path 150.

The droplet forming flow path 110, the second flow path 120, and the third flow path 130 are connected to one another such that the liquid containing DNA is continuously flows, for example. Accordingly, since liquid is caused to continuously flow from the droplet forming flow path 110 to the third flow path 130, the time required in sample processing can be easily shortened. In the case of the example shown in FIG. 32, liquid may be caused to continuously flow in all the flow paths, i.e., from the first flow path 160 to the fifth flow path 150. Alternatively, in the case of the example shown in FIG. 32, a configuration may be adopted in which: for example, liquid is caused to continuously flow from the droplet forming flow path 110 to the third flow path 130; and the liquid flow is temporarily stopped for sample processing, in any one or a plurality among the fourth flow path 140, the fifth flow path 150, the first flow path 160, and the dilution flow path 170. For example, in the dilution flow path 170, the liquid flow is temporarily stopped for a predetermined time in order to mix the liquid through thermal convection.

Liquids such as reagents and the liquid containing DNA as the target component sequentially flow in the flow paths in the fluid modules on the sample processing chip 100, whereby the emulsion PCR assay is performed. In the example shown in FIG. 32, Pre-PCR is performed in the first flow path 160, dilution is performed in the dilution flow path 170, and droplets 14 are formed (emulsion forming) in the droplet forming flow path 110. Nucleic acid amplification (PCR) is performed in the second flow path 120, droplet 14 breaking (emulsion breaking) is performed in the third flow path 130, the carrier 13 collecting process (washing) is performed in the fourth flow path 140, and binding (hybridization) between the amplification product and the labeled substance 17 is performed in the fifth flow path 150.

Thus, according to the configuration example shown in FIG. 32, the sample processing chip 100 includes the first flow path 160 for amplifying the nucleic acid 10 in the sample supplied by the sample processing apparatus 500, to a number necessary for forming droplets 14 by a predetermined amount or more. In the dilution flow path 170, the nucleic acid 10 amplified in the first flow path 160 and a predetermined amount of the diluent 18 are mixed together. This eliminates the need of amplifying the nucleic acid in advance by an external apparatus, and thus, convenience of the sample processing chip 100 can be improved. Therefore, even in a case where the Pre-PCR processing is performed in the sample processing chip 100, the nucleic acid can be diluted to a desired dilution rate in the dilution flow path 170, and thus, droplets 14 each containing only one molecule of the nucleic acid can be stably formed.

In the above configuration example shown in FIG. 32, the sample processing chip 100 further includes: the second flow path 120 for amplifying the nucleic acid 10 in each droplet 14 formed in the droplet forming flow path 110; and the third flow path 130 for mixing the droplets 14 and the reagent for breaking the droplets 14 together, the droplets 14 each containing the carrier 13 in which the amplification product of the nucleic acid 10 obtained in the second flow path 120 is bound to the primer 12. Accordingly, the PCR process for amplifying the nucleic acid in the droplets 14 and the emulsion breaking process for breaking the droplets 14 having been subjected to the PCR process can be performed in a single sample processing chip 100. Thus, compared with a case where the droplets formed in the droplet forming flow path 110 are taken out of the sample processing chip 100 and then the PCR process and the emulsion breaking process are performed in an external apparatus, convenience of the sample processing chip 100 can be improved, and a series of processes of the emulsion PCR assay can be speedily performed.

In the above configuration example shown in FIG. 32, the sample processing chip 100 further includes: the fourth flow path 140 for collecting the carrier 13 taken out of each broken droplet 14; and the fifth flow path 150 for causing the amplification product on the collected carrier 13 to react with the labeled substance 17. Accordingly, the process of collecting the carrier 13 and the process of causing the amplification product to react with the labeled substance 17 can be performed on the flow paths in the sample processing chip 100. For example, compared with a configuration in which droplets 14 are dispensed into a large number of wells formed in the sample processing chip 100, the above processes can be performed simply by causing liquid to flow in these flow paths, and thus, a series of processes of the emulsion PCR assay can be easily and speedily performed.

Hereinafter, configurations of the respective flow paths will be described in accordance with the flowing order of the liquid containing the nucleic acid.

<First Flow Path>

Figure 33:
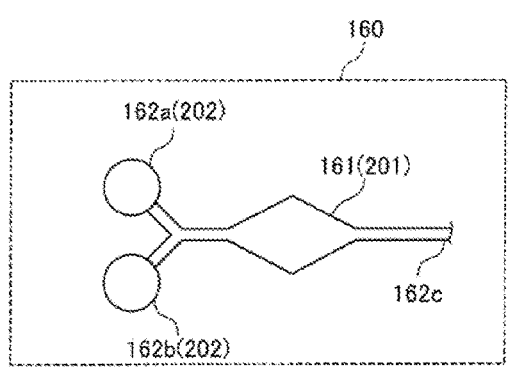
FIG. 33 shows a configuration example of a first flow path.

FIG. 33 shows a configuration example of the first flow path 160 to be used in the Pre-PCR. The first flow path 160 includes: a channel 161; connection portions 162a and 162b each for infusing a reagent or a sample; and a connection portion 162c for discharging liquid. For liquid flow rate control, the channel 161 has a rhombic shape, for example.

For example, DNA extracted in the pretreatment is infused from the connection portion 162a, and a PCR amplification reagent is infused from connection portion 162b. The temperature of the mixture of DNA and the reagent is controlled by the heater unit 541 while the mixture flows in the channel 161. Under the temperature control, DNA and the reagent react with each other, and DNA is amplified. The liquid containing the amplified DNA is transferred to the adjacent fluid module 200 via the connection portion 162c.

For example, in a case where the Pre-PCR is performed as pretreatment by an external apparatus, the first flow path 160 may not be provided to the sample processing chip 100.

<Dilution Flow Path>

Figure 34:
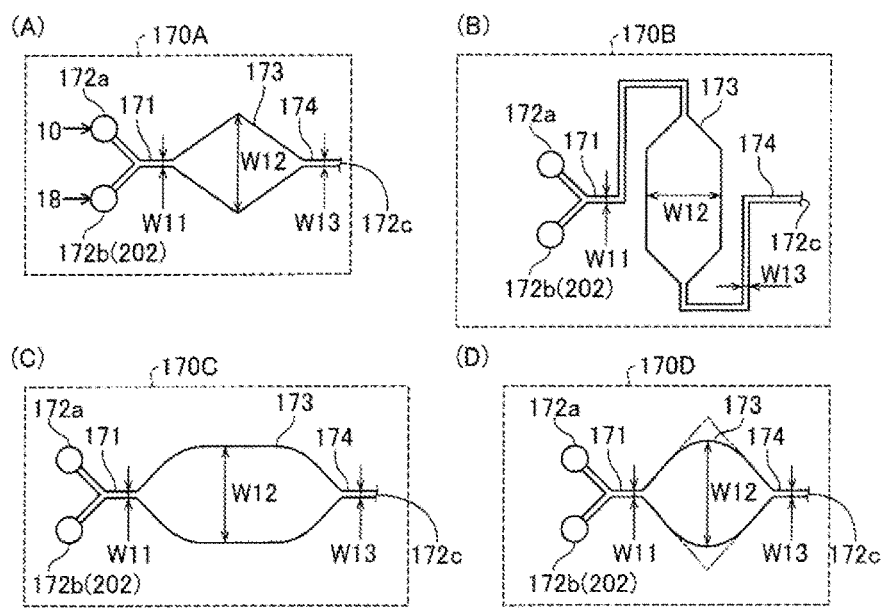
FIG. 34 shows configuration examples (A), (B), (C), and (D) of the dilution flow path.

(A) to (D) of FIG. 34 respectively show 170A, 170B, 170C, and 170D, as configuration examples of the dilution flow path 170 to be used in the dilution. Each of 170A, 170B, 170C, and 170D has the storage portion 173.

In the configuration examples shown in FIG. 34, the dilution flow path 170 is formed so as to extend along the main surface 301 (see FIG. 3) of the base plate 300, and includes a first flow path (channel) 171 for supplying liquid to the storage portion 173. The storage portion 173 has a shape in which, in the direction along the main surface 301, the flow path width of the storage portion 173 increases relative to a flow path width W11 of the first flow path 171. The flow path width of the storage portion 173 increases from the flow path width W11 up to a maximum flow path width W12. Accordingly, even in a case where the dilution flow path 170, which is a micro flow path, is formed in the sample processing chip 100 having a flat plate shape, the storage portion 173 having a sufficient capacity for realizing a desired dilution rate can be formed in a flat shape. It should be noted that the flow path width is the width in the direction perpendicular to the direction in which the liquid in the flow path flows.

The dilution flow path 170 further includes a second flow path 174 for sending out the liquid in the storage portion 173 to the droplet forming flow path 110. The second flow path 174 has a flow path width W13 smaller than the maximum flow path width W12 of the storage portion 173. Accordingly, the flow rate of the liquid sent out from the storage portion 173 to the droplet forming flow path 110 can be easily increased. As a result, droplets 14 can be efficiently formed in the droplet forming flow path 110.

According to the configuration examples shown in FIG. 34, the dilution flow path 170 includes: a connection portions 172a and 172b for respectively infusing the liquid containing the target component and a diluent; and a connection portion 172c for discharging the mixture having been diluted. The connection portions 172a and 172b are connected to the storage portion 173 via the first flow path 171, and the storage portion 173 is connected to the connection portion 172c via the second flow path 174. The liquid containing DNA diluted in the storage portion 173 flows in the second flow path 174, and is transferred via the connection portion 172c to the adjacent droplet forming flow path 110.

The dilution flow path 170A includes the storage portion 173 that has a substantially rhombic shape. The dilution flow paths 170B and 170C each include the storage portion 173 that has a substantially hexagonal shape. The substantially hexagonal storage portion 173 has a shape in which predetermined two sides are longer than the other sides. As to the dilution flow paths 170C and 170D, the overall shapes of the storage portions 173 are substantially a hexagon and a rhombus similar to those of the dilution flow paths 170B and 170A, respectively, but are rounded in the outer edges thereof, respectively. That is, the storage portion 173 of each of the dilution flow paths 170C and 170D does not have corners. Due to the rounded shape of the outer edge, when the liquid having been mixed through thermal convection is to be discharged from the storage portion 173, DNA is less likely to remain in the storage portion 173. Between the dilution flow paths 170B and 170C, the direction of the long side of the storage portion 173 is different.

As described above, the storage portion 173 of the dilution flow path 170 can be formed in a simple shape such as a substantially rhombic shape or a substantially hexagonal shape shown in FIG. 34, and does not require a complicated structure such as a meandering flow path. In the dilution flow path 170, in a state where the diluent 18 and DNA as the target component 10 are stored in the storage portion 173, DNA and the diluent are mixed together through thermal convection. Thus, the dilution flow path 170 does not require complicated control for conveying DNA and the diluent. As a result, for executing digital detection by use of the sample processing chip 100, it is possible to mix a plurality of components together, without making complicated the channel structure and the conveyance control for the components to be mixed.

In the dilution flow path 170, the target component is diluted at a dilution rate not less than 25 fold and not greater than 1500 fold, for example. The dilution rate is the ratio of the target component concentration before dilution to the target component concentration after dilution (dilution rate=target component concentration before dilution/target component concentration after dilution). Accordingly, DNA amplified in advance can be easily diluted to a desired concentration.

For example, a solution containing DNA (=the target component 10) amplified in the first flow path 160 is infused from the connection portion 172a into the storage portion 173. From the connection portion 172b, the diluent 18 is infused by an amount that can achieve a dilution rate for executing digital detection. The amount of the diluent 18 to be infused from the connection portion 172b is determined on the basis of the required dilution rate and the amount of the solution to be infused from the connection portion 172a. For example, in a case where the amount of the solution to be infused from the connection portion 172a is 1 µL and the required dilution rate is 50 fold, 49 μL of the diluent 18 is infused from the connection portion 172*b*.

As shown in (A) to (D) of FIG. 35, preferably, the dilution flow path 170 is disposed so as to be substantially parallel to the gravity direction G. That is, in a state where either the longitudinal direction Y or the short direction X (see FIG. 32) in the main flat face 301 of the sample processing chip 100 having a flat plate shape is aligned with the gravity direction G, the setting portion 510 holds the sample processing chip 100. Then, the heating portion 560 heats the mixture in the storage portion 173, thereby causing thermal convection in the storage portion 173.

The heating portion 560 can heat the region of a part of the storage portion 173. For example, the heating portion 560 heats substantially a half on the lower side in the gravity direction G of the storage portion 173. Accordingly, the storage portion 173 can be divided into two parts, i.e., a lower region having a relatively high temperature, and an upper region having a relatively low temperature. As a result, it becomes easy to suppress formation of a plurality of local thermal convections in the storage portion 173, thereby to form a large thermal convection that covers the entirety of the inside of the storage portion 173. Accordingly, mixing of the liquid in the storage portion 173 can be more speedily performed, and uniform concentration of the target component can be realized.

In order to cause thermal convection, the higher the heating temperature, the better. However, when the temperature is too high, there is a possibility that amplification of DNA starts. Therefore, the upper limit temperature of the heating portion 560 is preferably a value lower than the lower limit value of the amplification temperature. The lower limit value of the amplification temperature is 90° C., for example. Thus, for example, the heating portion 560 generates heat at a temperature of not less than 50° C. and not higher than 85° C., thereby to heat the mixture. Accordingly, efficient mixing can be performed while DNA amplification is prevented. The heating temperature is preferably as high as possible within the range of not less than 50° C. and not higher than 85° C., and preferably, about 80° C., for example.

For example, the heating portion 560 heats the mixture for a predetermined time of less than 10 minutes, thereby to complete mixing of the target component and the diluent through thermal convection. Although depending on the liquid amount and the dilution rate, a predetermined time of less than 10 minutes does not increase, more than necessary, the processing time in the entirety of the sample processing chip 100, and can realize speedy mixing.

Hereinafter, experiment methods will be described in which DNA was diluted by use of thermal convection caused in the storage portion 173 by the heat from the heating portion 560.

(Experiment Method 1)

Figure 36:
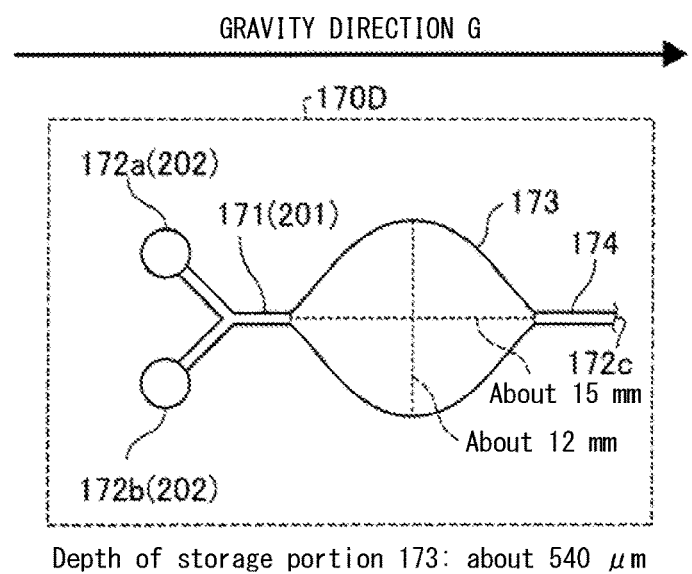
FIG. 36 is a diagram for explaining an experiment example of mixing through thermal convection in the dilution flow path.

An experiment was performed by use of the dilution flow path 170D having the storage portion 173 in a rounded rhombic shape shown in FIG. 36. Two diagonal lines of the rhombic storage portion 173 were about 12 mm and about 15 mm, respectively. The depth (=thickness) of the storage portion 173 was about 540 μm. Dilutions were performed in the dilution flow path 170D shown in FIG. 36, with the target value (theoretical value) of the dilution rate of DNA set to 30 fold and 50 fold, respectively. It should be noted that the dilution rate is the ratio of the DNA concentration before dilution to the DNA concentration after dilution (dilution rate=DNA concentration before dilution/DNA concentration after dilution).

The dilution flow path 170 was disposed such that either one of the two diagonal lines of the rhombic storage portion 173 was in parallel to the gravity direction G. In the present experiment, as shown in FIG. 36, the dilution flow path 170 was disposed such that the longer one of the two diagonal lines of the rhombic storage portion was in parallel to the gravity direction G.

1 μL of a solution containing DNA was infused from the connection portion 172*a*. When DNA was diluted at a dilution rate of 30 fold, 29 μL of a diluent (Nuclease free Water, the same applies below) was infused from the connection portion 172*b*. When DNA was diluted at a dilution rate of 50 fold, 49 μL of the diluent was infused from the connection portion 172*b*.

After DNA and the diluent were stored in the storage portion 173, the area of about a half of the storage portion 173 was heated by the heating portion 560. The heating temperature was set to about 80° C. Thermal convection was caused in the storage portion 173 by heat, and the dilution flow path 170D was left still for about 10 minutes.

After the dilution flow path 170D was left still for about 10 minutes, the mixture in the storage portion 173 was collected, and the collected mixture was subjected to quantitative PCR. DNA in the mixture was quantified by the quantitative PCR, and the dilution rate (DNA concentration before dilution/DNA concentration after dilution) was calculated.

The experiment value obtained when DNA had been diluted at a dilution rate of 30 fold was 28.7 fold on average, and the experiment value obtained when DNA had been diluted at a dilution rate of 50 fold was 60.6 fold on average. Thus, it was confirmed that a desired dilution rate can be obtained by mixing DNA and the diluent together by causing thermal convection in the storage portion 173 of the dilution flow path 170.

(Experiment Method 2)

With respect to the thermal convection in the storage portion 173 of the dilution flow path 170, an experiment by computer simulation was also performed. For the simulation, software for thermal convection analysis "STAR-CCM+(registered trademark)" was used.

Figure 37A:
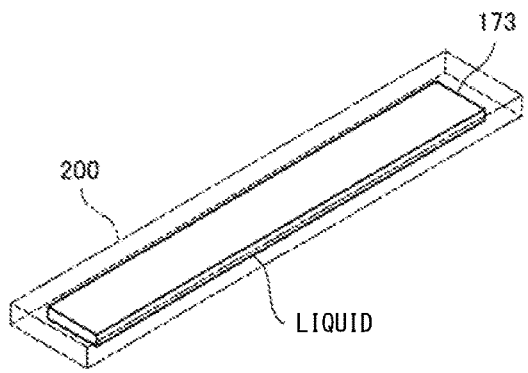
FIG. 37A is a diagram for explaining a first simulation regarding mixing through thermal convection in dilution flow path.
Figure 37B:
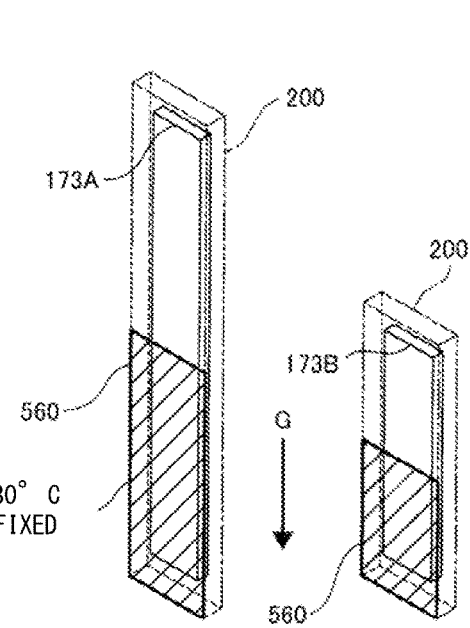
FIG. 37B is a diagram for explaining the first simulation regarding mixing through thermal convection in dilution flow path.

As shown in FIGS. 37A and 37B, a rectangular storage portion 173 was used as an analysis model. In the analysis model, 80° C. heat was applied for 10 minutes to the area of about a half of the storage portion 173 filled with liquid. The initial temperature of the liquid in the storage portion was set at 25° C., and the ambient temperature was set at 25° C. The analysis model was created such that the long side of the rectangular storage portion was parallel to the gravity direction.

Figure 38A:
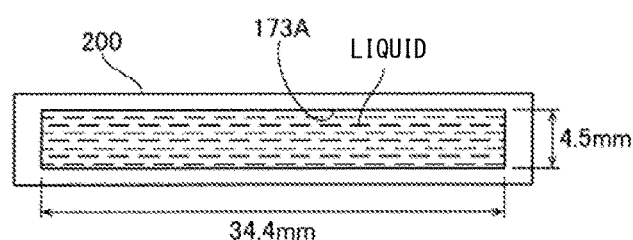
FIG. 38A is a diagram for explaining dimensions of a storage portion used in the first simulation.
Figure 38B:
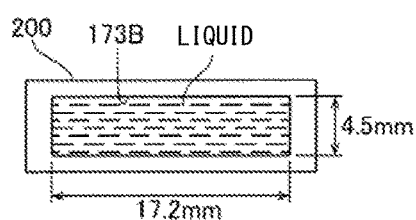
FIG. 38B is a diagram for explaining dimensions of the storage portion used in the first simulation.
Figure 38C:
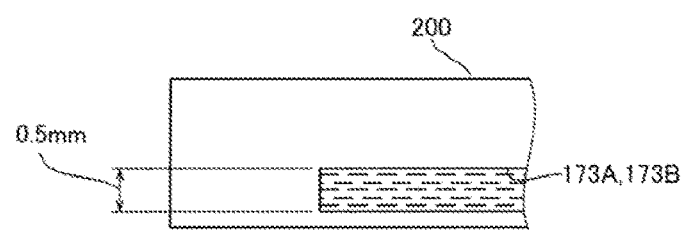
FIG. 38C is a diagram for explaining dimensions of the storage portion used in the first simulation.

FIGS. 38A to 38C each show dimension data of the storage portion 173 as the analysis model. In the present experiment, two kinds of analysis models, i.e., rectangular storage portions 173A and 173B (see FIGS. 38A and 38B), were created. As shown in FIG. 38C, the thickness of the liquid filled in the storage portion 173 (i.e., depth of the storage portion 173) was the same between the two kinds of the rectangular storage portion 173A and 173B, and was 0.5 mm.

In the simulation, the storage portion 173 was completely filled with the liquid, and thus, the dimensions of the storage portion 173 were equal to the dimensions of the liquid filled in the storage portion 173. In the analysis model shown in FIG. 38A, the dimensions of the storage portion 173A were 34.4 mm×4.5 mm, and the aspect ratio thereof was about 7.6. In the analysis model shown in FIG. 38B, the dimensions of the storage portion 173B were 17.2 mm×4.5 mm, and the aspect ratio was about 3.8.

The liquid filled in the storage portion 173 was the mixture of the sample (DNA) and the diluent. In the analysis model shown in FIG. 38A, the amount of the sample was set to 0.0516 μL, and the amount of the diluent was set to 77.3484 μL. In the analysis model shown in FIG. 38B, the amount of the sample was set to 0.0258 μL, and the amount of the diluent was set to 38.6742 μL. In each case, the theoretical dilution rate was 1500 fold.

Figure 39A:
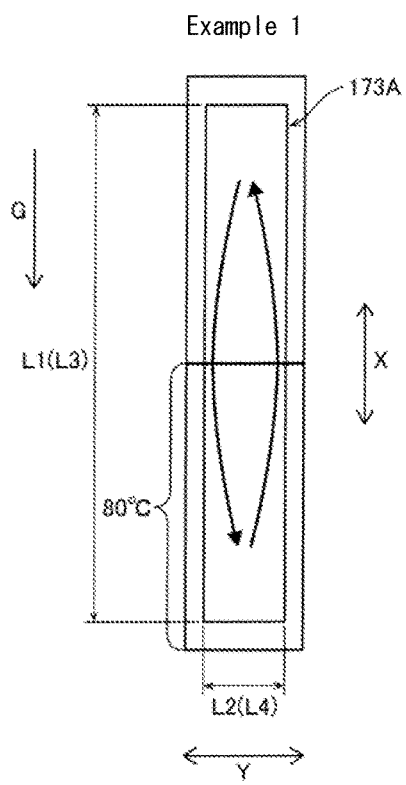
FIG. 39A is a diagram showing the heated region in the storage portion used in the first simulation.
Figure 39B:
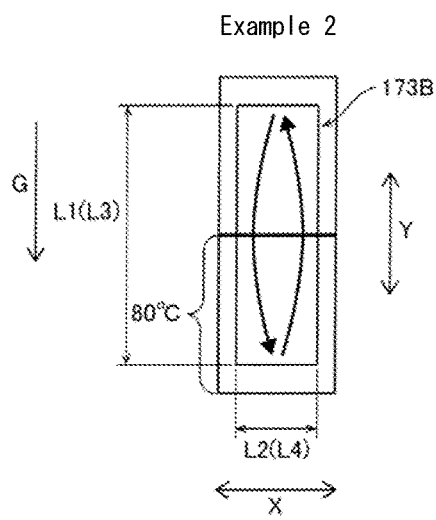
FIG. 39B is a diagram showing the heated region in the storage portion used in the first simulation.

As shown in FIGS. 39A and 39B, the longitudinal direction of each of the rectangular storage portions 173A (Example 1) and 173B (Example 2) of the respective analysis models was aligned with the gravity direction G, and the area of about a half of the lower side thereof was heated to 80° C., whereby agitation simulation of the mixture in the storage portion through thermal convection was performed. As Comparative Examples, in each of the analysis models shown in FIGS. 39A and 39B (Comparative Examples 1 and 2), simulation was performed also with respect to a case where natural diffusion was allowed to occur without application of heat.

Figure 40:
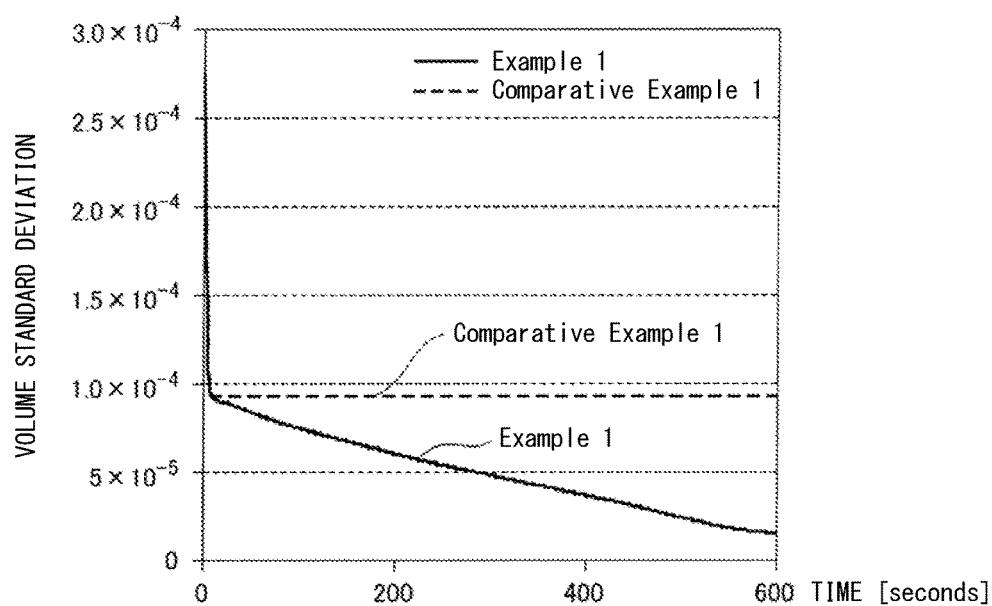
FIG. 40 shows simulation results of Example 1 and Comparative Example 1 regarding the storage portion.
Figures 41, 42:
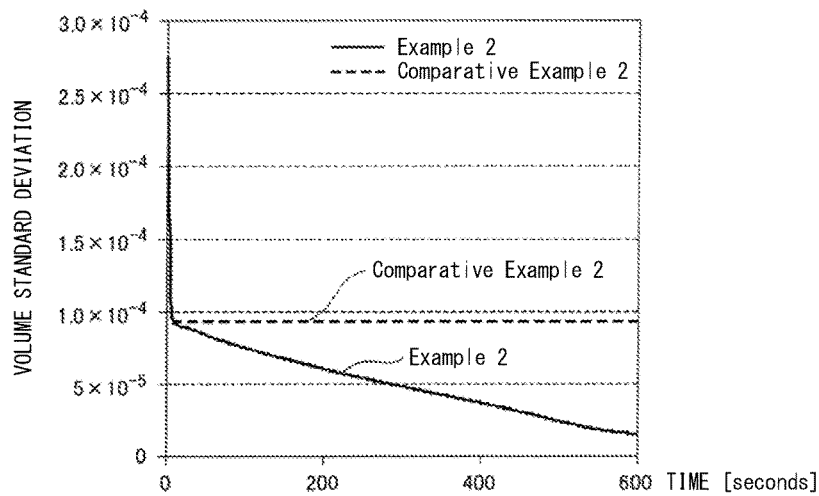
FIG. 41 shows simulation results of Example 2 and Comparative Example 2 regarding the storage portion.
FIG. 42 shows condition settings of the storage portion (No. 1 to No. 6) used in a second simulation.

Each of FIG. 40 and FIG. 41 is a graph showing the result of the simulation.

The vertical axis of each graph represents volume standard deviation. The volume standard deviation indicates the variation of the sample (DNA) in the mixture in the storage portion 173. The smaller the volume standard deviation is, the less locally the sample exists in the mixture. That is, the smaller the volume standard deviation is, the more uniformly the sample is mixed in the mixture.

The horizontal axis of each graph represents the time for which the mixture was agitated.

From FIG. 40 and FIG. 41, it was confirmed that the mixing more speedily advanced in Examples 1 and 2 (solid line) in which thermal convection was caused by heating, than in Comparative Examples 1 and 2 (broken line) in which heating was not performed. In addition, it was confirmed that the mixing more speedily advanced in the analysis model in FIG. 39B (see FIG. 41), than in the analysis model in FIG. 39A (see FIG. 40). That is, the smaller the aspect ratio of the mixture in the storage portion 173 was (i.e., the closer to 1 the aspect ratio was), the more speedily the mixing advanced, and the more improved the dilution efficiency was.

(Experiment Method 3)

Simulation similar to Experiment method 2 was performed under a still different condition. As shown in FIG. 42, six kinds of analysis models having different conditions were set. The storage portions 173 of the analysis models of No. 1 to No. 6 respectively have different dimensions. The simulation was performed under a condition in which the same amount of liquid was stored in each of the six kinds of analysis models in which the respective storage portions 173 have different dimensions.

As the respective analysis models, a total of six kinds of the storage portion 173 (No. 1 to No. 6) were prepared by the following manner: two thicknesses of 0.5 mm and 0.8 mm were set for each of three kinds of dimension variations, i.e., (vertical dimension×horizontal dimension)=(43 mm×11.25 mm), (41.7 mm×12 mm), and (33.4 mm×15 mm). The gravity direction G was directed downward in FIG. 42, and was aligned with the longitudinal direction of the storage portion 173. The aspect ratio of the vertical dimension to the horizontal dimension of the storage portion 173 was about 3.82 (No. 1, No. 4), about 3.48 (No. 2, No. 5), and about 2.23 (No. 3, No. 6).

The capacity of the storage portion 173 in each analysis model was as shown in FIG. 42. When 180 μL of liquid was stored in each of the six kinds of the analysis models, the vertical dimension of the stored liquid varied as indicated by the hatching in FIG. 42. As a result, the aspect ratio of the vertical dimension to the horizontal dimension of the stored mixture was about 2.84 (No. 1), 2.5 (No. 2), 1.6 (No. 3), about 1.78 (No. 4), about 1.56 (No. 5), and 1 (No. 6).

Figure 43:
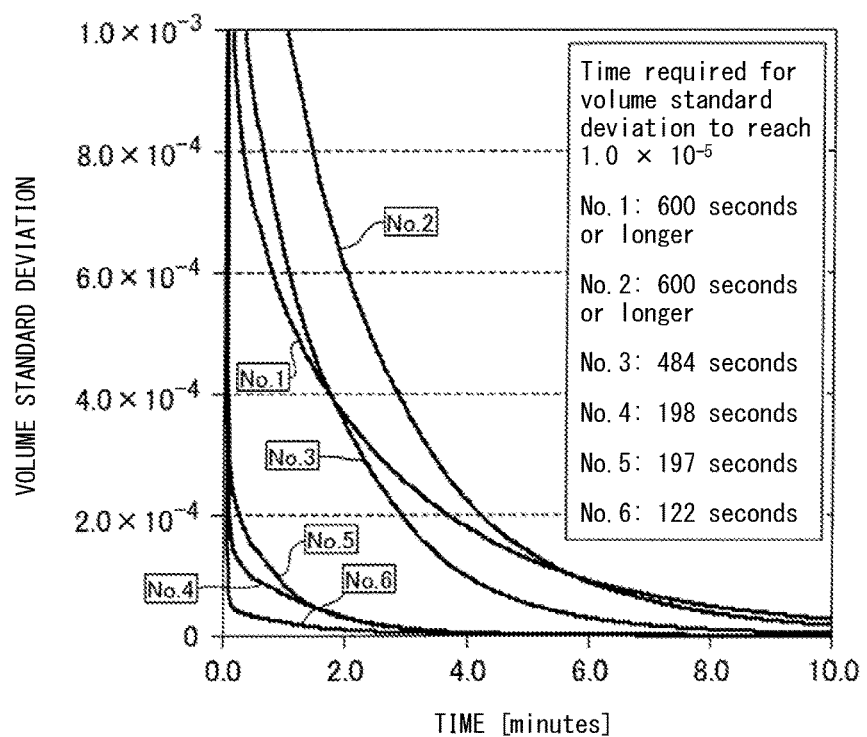
FIG. 43 shows results (No. 1 to No. 6) of the second simulation.

FIG. 43 is a graph showing the result of the simulation. As a measure for the advancing speed of the mixing, the time required from when the simulation started to when the volume standard deviation reached $1.0\times10^{-5}$ was calculated. The required time up to when the volume standard deviation reached $1.0\times10^{-5}$ was in the order of No. 1 to No. 6, from the longest of the required time. It is considered that the difference in the advancing speed of the mixing between the group of No. 1 to No. 3 and the group of No. 4 to No. 6 is caused by the difference in the thickness of the storage portion 173.

When compared within a group having the same thickness, as to the group of No. 1 to No. 3, the mixing advanced most speedily (484 seconds) in No. 3 which had the smallest aspect ratio (aspect ratio 1.6). Also as to the group of No. 4 to No. 6, the mixing advanced most speedily (122 seconds) in No. 6 which had the smallest aspect ratio (aspect ratio 1).

In this manner, the smaller the aspect ratio of the vertical dimension to the horizontal dimension of the mixture stored in the storage portion 173 was (i.e., the closer to 1 the aspect ratio was), the more speedily the mixing advanced and the more improved the dilution efficiency was. From this result, it is seen that, irrespective of the shape of the storage portion 173, the mixing through thermal convection can be efficiently advanced by adjusting the amount of the mixture stored in the storage portion 173 such that the aspect ratio of the vertical dimension to the horizontal dimension of the stored mixture satisfies a desired value.

Therefore, according to the present embodiment, as shown in FIG. 39 and FIG. 42, the following configuration is preferable. That is, in a state where either the longitudinal direction Y or the short direction X (see FIG. 32) of the main flat face 301 (see FIG. 3) of the sample processing chip 100 having a flat plate shape is aligned with the gravity direction G, the direction along the gravity direction G is set as the vertical direction of the storage portion 173, and the direction along the other of the longitudinal direction Y or the short direction X is set as the horizontal direction of the storage portion 173. Then, into the storage portion 173, the mixture is stored by a predetermined amount that realizes an aspect ratio (L1/L2) of a length L1 in the vertical direction by which the mixture occupies the storage portion 173 to a length L2 in the horizontal direction by which the mixture occupies the storage portion 173 is not less than 0.1 and not greater than 10. Accordingly, the mixing through thermal convection can be speedily advanced.

Moreover, the closer to 1 the aspect ratio of a vertical dimension L3 to a horizontal dimension L4 of the storage portion 173 itself is, the closer to 1 the aspect ratio of the mixture can be made, even when the mixture is stored close to the upper limit of the capacity of the storage portion 173. Thus, it is seen that dead space can be reduced when an appropriate amount of the mixture is stored.

Therefore, according to the present embodiment, as shown in FIG. 42, preferably, the storage portion 173 has a shape in which the aspect ratio (L3/L4) of the first length L3 of the storage portion 173 along the longitudinal direction Y of the first face 301 to the second length L4 of the storage portion 173 along the short direction X of the first face 301 is not less than 0.1 and not greater than 10. Accordingly, in a state of use in which the long side or the short side of the sample processing chip 100 is aligned with the gravity direction, the aspect ratio of the storage portion 173 can be set in a desired range. As a result, without increasing the size of the storage portion 173 more than necessary, it is also possible to easily make the aspect ratio of the mixture in the storage portion 173 closer to 1.

(Other Configuration Examples of Dilution Flow Path)

Figure 44:
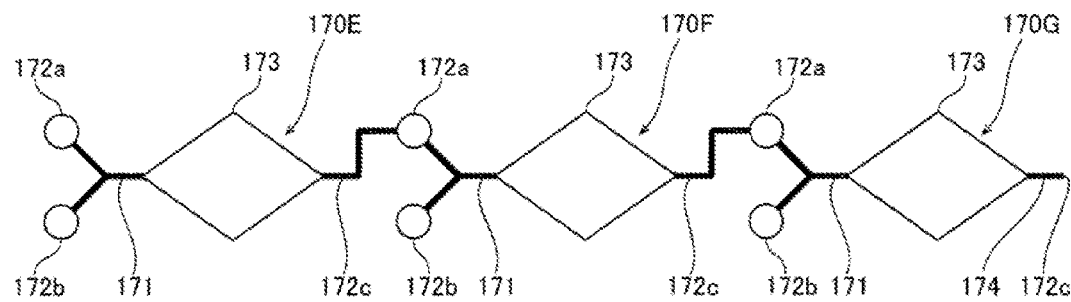
FIG. 44 shows another configuration example of the dilution flow path.

FIG. 44 shows another configuration example of the dilution flow path 170.

In the configuration example shown in FIG. 44, the sample processing chip 100 includes a plurality of the dilution flow paths 170 (170E, 170F, 170G) connected to one another in series. Of the mixture of the target component 10 and the diluent 18 diluted in the dilution flow path 170E in the former stage, a predetermined amount of the mixture is supplied to the dilution flow path 170F in the latter stage. Accordingly, in each of plurality of the dilution flow paths 170 which are connected to one another in series, the target component 10 can be sequentially diluted. Thus, a high dilution rate that cannot be obtained in a single dilution flow path 170 can be easily realized. In addition, simply by changing the number of serially connected fluid modules 200 that each has a single dilution flow path 170, for example, the dilution rate can be freely changed. Thus, even in a case where a single type of dilution flow path 170 is used, it is possible to flexibly manage various kinds of sample processing chips 100 for which required dilution rate and usage are different.

In the example shown in FIG. 44, three dilution flow paths 170 (170E, 170F, 170G) are connected to one another in series. The plurality of the dilution flow paths 170, as a whole, dilutes the target component 10 at a dilution rate obtained by multiplying the dilution rates of the individual dilution flow paths 170. Accordingly, a high dilution rate can be easily realized.

For example, if 1 µL of DNA is infused from the connection portion 172a of the dilution flow path 170E, 49 µL of a diluent is infused from the connection portion 172b, and the DNA and the diluent are mixed together through thermal convection in the storage portion 173, the DNA is diluted at a dilution rate of 50 fold.

The DNA diluted in the dilution flow path 170E is infused into the dilution flow path 170F. Specifically, 1 µL of the DNA diluted in the dilution flow path 170E is infused from the connection portion 172a of the dilution flow path 170F, and 49 µL of the diluent is infused from the connection portion 172b of the dilution flow path 170F. Then, the mixture of the DNA and the diluent is mixed through thermal convection in the storage portion 173 of the dilution flow path 170F. The DNA diluted at 50 fold in the dilution flow path 170E is further diluted at a rate of 50 fold in the dilution flow path 170F. As a result, DNA diluted at 2500 fold ($50^2$) is obtained.

The DNA diluted in the dilution flow path 170F is infused into the dilution flow path 170G. Specifically, 1 µL of the DNA diluted in the dilution flow path 170F is infused from the connection portion 172a of the dilution flow path 170G, and 49 µL of the diluent is infused from the connection portion 172b of the dilution flow path 170G. The mixture of the DNA and the diluent is mixed through thermal convection in the storage portion 173 of the dilution flow path 170G. The DNA diluted at 2500 fold through the dilution flow paths 170E and 170F is further diluted at a rate of 50 fold in the dilution flow path 170G. As a result, DNA diluted at 125000 fold ($50^3$) is obtained.

The dilution rate to be achieved can be controlled by the number of the dilution flow paths 170 to be connected in series and the amounts of DNA and the diluent to be infused into each flow path. For example, two dilution flow paths 170 (assuming that 170E and 170F are used) are connected to each other in series, and 0.1 µL of DNA and 149.9 µL of the diluent are infused into the dilution flow path 170E and mixed therein. 0.1 µL of the mixture diluted in the dilution flow path 170E is infused into the dilution flow path 170F, and diluted with 149.9 µL of the diluent. As a result, the dilution rate achieved through the two dilution flow paths 170 becomes 2.25 million fold ($1500^2$).

Preferably, in a plurality of the dilution flow paths 170, as a whole, the target component is diluted at a dilution rate of not less than $10^3$ fold and not greater than $10^7$ fold. Accordingly, even when DNA is preliminarily amplified to a number that allows the amplification result of the Pre-PCR to be sufficiently stable, the plurality of the dilution flow paths 170 allow the target component to be easily diluted to a dilution rate required in the emulsion forming process. For example, when the number of DNA after the Pre-PCR processing is about $10^8$ to $10^{12}$, about 46 fold to 460 thousand fold is required in the entirety of one or a plurality of the dilution flow paths 170. Thus, also when the number of DNA having been amplified is especially large, if the dilution rate is not less than $10^3$ fold and not greater than $10^7$ fold, sufficient dilution can be realized.

<Droplet Forming Flow Path>

Figure 45:
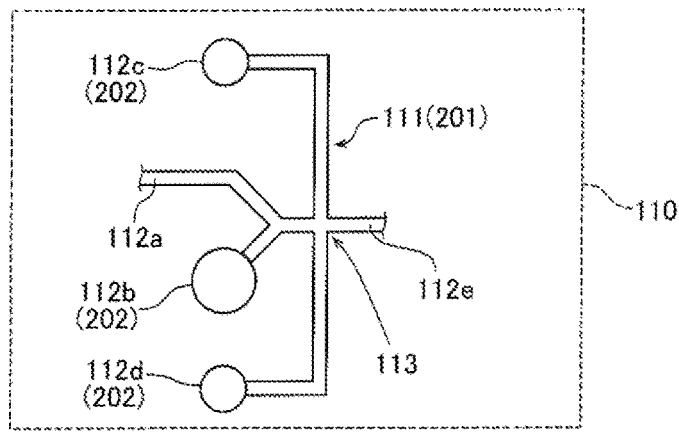
FIG. 45 shows a configuration example of a droplet forming flow path.

FIG. 45 shows a configuration example of the droplet forming flow path 110 to be used in formation of an emulsion. The droplet forming flow path 110 includes: a channel 111; connection portions 112a, 112b, 112c, and 112d into each of which a liquid such as a sample or a reagent is infused; and a connection portion 112e from which liquid is discharged. It should be noted that only either one of the connection portions 112a and 112b may be provided to the droplet forming flow path 110. The channel 111 includes a crossing part 113 at which at least two channels cross each other, for example.

For example, the liquid containing DNA amplified in the Pre-PCR flows in from the connection portion 112a, and a liquid containing the carrier 13 and the reagent 11 for amplification reaction is infused from connection portion 112b. In this example, the carrier 13 is magnetic particles. The liquids respectively infused from the connection portions 112a and 112b are mixed together in the channel 111, and flows into the crossing part 113. The particle size of the magnetic particle is 0.5 µm to 3 µm, for example. In order to send the liquids to the connection portions 112a and 112b, the pump 521 applies a pressure P (1000 mbar≤P≤10000 mbar).

For example, the dispersion medium 15 is infused from the connection portions 112c and 112d. The dispersion medium 15 is an oil for forming an emulsion, for example. The respective flows of the infused oil pass through different routes into the crossing part 113. In order to send the oil to the connection portions 112c and 112d, the pump 521 applies a pressure P (1000 mbar≤P≤10000 mbar). The flow of the mixture and the flows of the dispersion medium 15 cross one another in the crossing part 113, whereby an emulsion is formed.

In the present embodiment, in order to increase the resistance to the pressure applied by the pump 521, the thickness d of the base plate 300 is preferably set to 2 mm or greater. For example, if the liquid sending pressure is set to be about 8000 mbar, when the base plate 300 is too thin, a crack might be caused. By setting the thickness d of the base plate 300 to 2 mm or greater, occurrence of a crack in the base plate 300 is inhibited.

Figure 46:
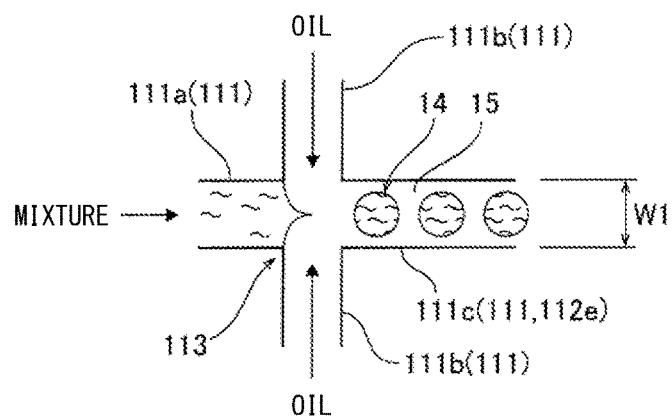
FIG. 46 is an enlarged view showing a first example of a crossing part in which an emulsion is formed.

FIG. 46 shows a configuration example of the crossing part 113.

In the example shown in FIG. 46, the droplet forming flow path 110 includes: a first channel 111a in which the mixture flows; second channels 111b in which the dispersion medium 15 non-miscible with the mixture flows; and the crossing part 113 at which the first channel 111a and the second channels 111b cross one another. Thus, the flows of the dispersion medium 15 apply shear force to the flow of the mixture, whereby droplets 14 of the mixture can be efficiently formed.

In the example shown in FIG. 46, the crossing part 113 is formed such that the first channel 111a and the second channels 111b orthogonally cross each other. In addition, at the crossing part 113, the first channel 111a and a third channel 111c which is connected to the connection portion 112e for discharge are formed in a linear shape, and the second channels 111b are connected, orthogonally, to the first channel 111a and the third channel 111c. At the crossing part 113, the two second channels 111b cross the single first channel 111a so as to sandwich the first channel 111a from both sides thereof.

A width W1 of each of the channels 111a to 111c at the crossing part 113 is not less than 5 μm and not greater than 100 for example. Accordingly, while assuring a sufficient generation speed of droplets 14 (i.e., the number of droplets generated per unit time), it is possible to suppress occurrence of clogging of the channels 111a to 111c. In the present embodiment, the width W1 of the channels 111a to 111c is about 20 μm.

The mixture of DNA and the reagent flows through the first channel 111a into the crossing part 113. The oil flows into the crossing part 113 from the second channels 111b extending in the up-down direction in FIG. 46. The mixture is cut into droplets 14 by the shear force that has occurred as a result of the mixture being sandwiched by the oil at the crossing part 113. The cut droplets 14 are each covered by the oil that has flowed into the crossing part 113, whereby an emulsion is formed. That is, in the droplet forming flow path 110, DNA as the target component 10 is encapsulated, by one molecule, into each droplet 14. The specimen flow in the form of an emulsion advances through the third channel 111c, to be transferred via the connection portion 112e into the adjacent second flow path 120.

The controller 530 controls the supply pressures for the mixture and the dispersion medium 15 of the liquid sending portion 520 such that the mixture and the dispersion medium 15 are transferred under the pressures into the droplet forming flow path 110, to form droplets 14. Accordingly, compared with a configuration in which a mixture is dropped into the dispersion medium 15 stored in a well, for example, droplets 14 can be continuously formed in the dispersion medium 15 to which pressure is being applied. As a result, droplets 14 can be generated at a high speed.

For example, the mixture of DNA and the reagent flows into the crossing part 113 at a flow rate of 0.4 μL/min to 7 μL/min, and the oil flows into the crossing part 113 at a flow rate of 1 μL/min to 50 μL/min. The flow rate is controlled by the pressure applied by the pump 521. For example, when the mixture of DNA and the reagent is caused to flow into the crossing part 113 at the flow rate of 2 μL/min (about 5200 mbar) and the oil is caused to flow into the crossing part 113 at the flow rate of 14 μL/min (about 8200 mbar), droplets 14 are formed by about 10 million/min.

The controller 530 controls the pressure of the liquid sending portion 520 such that droplets 14 are formed at a rate of not less than 600 thousand/minute and not greater than 18 million/minute. By forming droplets 14 at such a high speed, it is possible to shorten the time required in the sample processing. Meanwhile, when droplets 14 are formed at a high speed, it becomes difficult to accurately control the particle size of individual droplets 14, the variation in the generation speed, and the like. However, in the present embodiment, since droplets 14 after the amplification process are broken in the third flow path 130, accurate control of the particle size of droplets 14, generation speed thereof, and the like is not necessary. Thus, droplet formation can be performed at a high speed without influencing the accuracy of nucleic acid detection.

In order to form droplets 14 at a high speed in this manner, it is necessary to apply a high pressure to the sample processing chip 100. As described above, by setting the thickness d of the base plate 300 and selecting the material of the base plate 300, it is possible to easily obtain the base plate 300 that can bear a high pressure. Further, since through-holes 310 provided in the base plate 300 are used as ports 101 for liquid infusion, the pressure-resisting ability of the ports 101 for liquid infusion of the sample processing chip 100 can be easily increased. Forming each through-hole 310 in a simple shape such as a through-hole extending in the thickness direction also contributes to the enhancement of the pressure-resisting ability.

Figure 47:
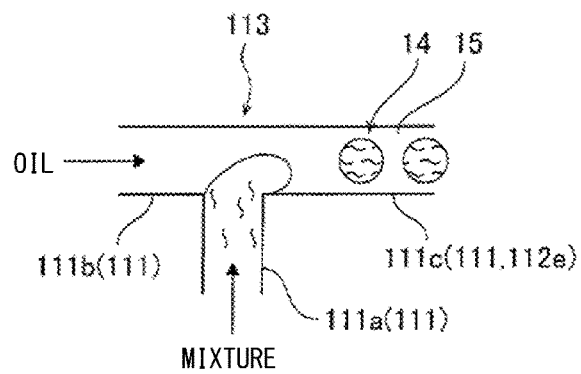
FIG. 47 is an enlarged view showing a second example of the crossing part in which an emulsion is formed.

In the example shown in FIG. 46, the crossing part 113 is formed in the shape of a cross composed of four channels 111 in total, i.e., one first channel 111a into which the mixture flows, two second channels 111b into which the oil flows, and one third channel 111c from which the emulsion flows out. In the example shown in FIG. 47, the crossing part 113 is formed in a T-shape composed of three channels 111. In the example shown in FIG. 47, the mixture flows in from a single first channel 111a, and the oil flows in from a single second channel 111b. By the shear force of the oil flow, the mixture is made into droplets in the oil, whereby an emulsion is formed. The specimen flow in the form of emulsion flows out from a single third channel 111c.

<Second Flow Path>

Figure 48:
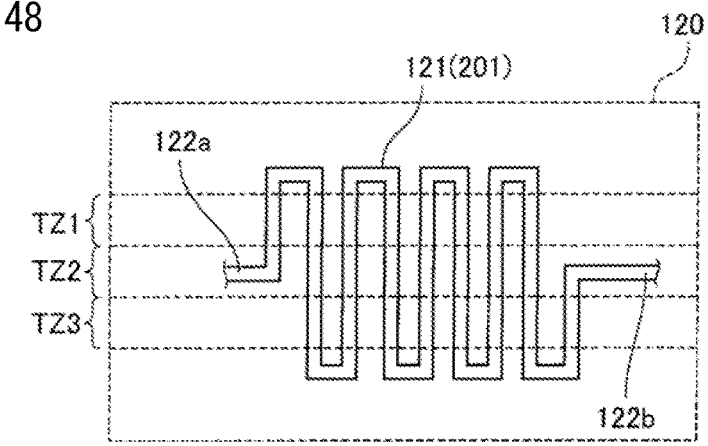
FIG. 48 shows a configuration example of a second flow path.

FIG. 48 shows a configuration example of the second flow path 120 to be used in the emulsion PCR. The second flow path 120 includes: a channel 121; a connection portion 122a into which liquid flows; and a connection portion 122b from which liquid is discharged.

The second flow path 120 is formed such that droplets 14 alternately pass a plurality of temperature zones TZ, for example. Accordingly, simply by transferring the droplets 14 in the second flow path 120, a thermal cycle process can be performed. That is, for example, compared with a configuration in which the droplets 14 are stopped in the second flow path 120 and the temperature of the heater unit 541 is cyclically varied, the process can be speedily performed. In addition, operation control on the sample processing apparatus 500 side for handling the sample processing chip 100 can be simplified. The number of temperature zones TZ may be a number other than three.

In the example shown in FIG. 48, the channel 121 has a meandering structure which passes a plurality of times a plurality of temperature zone TZ1 to TZ3 formed by the heater unit 541. The number of times by which the channel 121 passes the temperature zones TZ1 to TZ3 corresponds to the number of thermal cycles. That is, the second flow path 120 is formed in a shape in which the path crosses a plurality of temperature zones TZ, and reciprocates through the plurality of temperature zones TZ by the number of times that corresponds to the number of thermal cycles. Accordingly, simply by causing the emulsion containing the droplets 14 to pass through the second flow path 120, it is possible to easily perform a thermal cycle process by a desired number of cycles.

The number of thermal cycles for the emulsion PCR is set to about 40 cycles, for example. Thus, although depicted in a simplified manner in FIG. 48, the channel 121 is formed in a shape in which the path reciprocates or meanders by the number of times that corresponds to the number of cycles such that the path crosses the temperature zones TZ1 to TZ3 about 40 times.

As shown in FIG. 48, DNA in each droplet 14 is amplified while flowing in the channel 121. Each droplet 14 containing the amplified DNA is transferred via the connection portion 122b to the adjacent third flow path 130.

<Third Flow Path>

Figure 49:
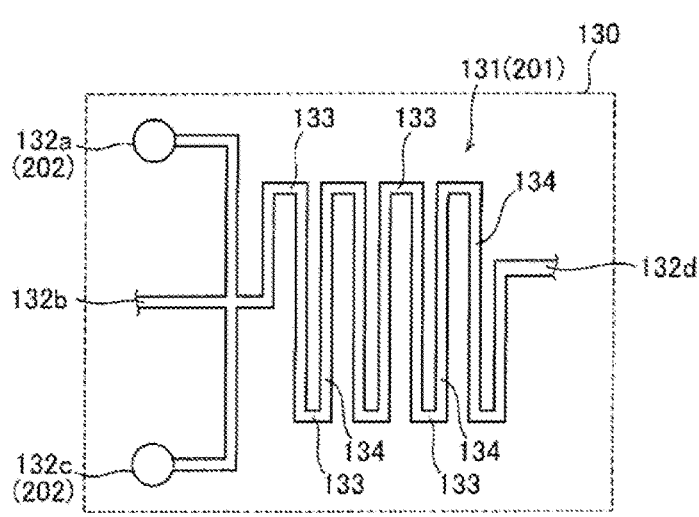
FIG. 49 shows a configuration example of a third flow path.

FIG. 49 shows a configuration example of the third flow path 130 to be used in breaking of the emulsion. The third flow path 130 has a function of mixing a plurality of liquids. The third flow path 130 includes: a channel 131; connection portions 132a, 132b, and 132c into each of which the emulsion, the reagent 16 for breaking droplets, or the like flows in; and a connection portion 132d from which liquid is discharged.

For example, the emulsion having been subjected to the emulsion PCR step flows in from the connection portion 132b, and a reagent for breaking droplets flows in from the connection portions 132a and 132c. The emulsion and the reagent for breaking droplets are mixed together while flowing in the channel 131, whereby the droplets 14 in the emulsion are broken. The channel 131 is formed in a shape that accelerates the mixing of the liquids.

For example, the third flow path 130 has a winding shape so as to generate a turbulent flow for mixing the droplets 14 and the reagent for breaking droplets. Accordingly, the droplets 14 and the reagent for breaking droplets are agitated while passing through the winding third flow path 130, and thus, the mixing can be accelerated.

Specifically, the third flow path 130 has a meandering shape, for example. Accordingly, a large number of curved or bent portions can be provided to the third flow path 130, and thus, the mixing can be more effectively accelerated. In the configuration example shown in FIG. 49, the third flow path 130 includes: a plurality of bent portions 133; and a plurality of linear portions 134 connecting the bent portions 133. In other words, the third flow path 130 has a turn-around structure in which each linear portion 134 is turned around at a bent portion 133 to the opposite side. Accordingly, by the liquid alternately passing a linear portion 134 and a bent portion 133, a turbulent flow can be repeatedly generated, whereby the liquid can be agitated. As a result, the mixing can be more effectively accelerated. The magnetic particles taken out from the droplets 14 are transferred via the connection portion 132d to the adjacent fourth flow path 140.

<Fourth Flow Path>

Figure 50:
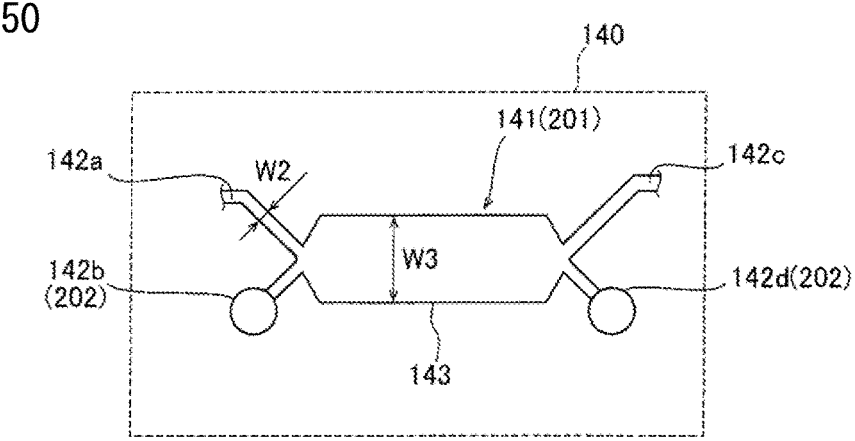
FIG. 50 shows a configuration example of a fourth flow path.

FIG. 50 shows a configuration example of the fourth flow path 140 to be used in a washing step (primary washing). The fourth flow path 140 includes: a channel 141; connection portions 142a and 142b into each of which liquid flows in; and connection portions 142c and 142d from each of which liquid is discharged.

The fourth flow path 140 includes a linear portion 143 in which magnetic particles are captured by magnetic force and the magnetic particles are moved in a reciprocating manner in the direction along the fourth flow path 140. Accordingly, the magnetic particle can be easily collected and washed on the linear portion 143. In addition, by moving the magnetic particles in a reciprocating manner in the washing liquid on the linear portion 143, it is possible to inhibit the magnetic particles from sticking together and aggregating. The linear portion 143 has a shape linearly extending in a predetermined direction, such as a substantially rectangular shape, for example. In the example shown in FIG. 50, the entirety of the channel 141 is formed as the linear portion 143. The linear portion 143 may be formed as a part of the channel 141.

In the example shown in FIG. 50, the connection portions 142a and 142b on the flow-in side are connected to one end side of the linear portion 143, and the connection portions 142c and 142d on the discharge side are connected to the other end side of the linear portion 143. One of the connection portions 142a and 142b is a connection portion for supplying the washing liquid, and the other of the connection portions 142a and 142b is a connection portion for supplying the magnetic particles. One of the connection portions 142c and 142d is a connection portion for discharging the washing liquid, and the other of the connection portions 142c and 142d is a connection portion for sending out the magnetic particles to the next flow path. Accordingly, operation of sending the magnetic particles into the fourth flow path 140, operation of causing the washing liquid to flow in the fourth flow path 140 while discharging the washing liquid therefrom, and operation of sending out the washed magnetic particles from the fourth flow path 140 can be performed by causing the respective liquids to flow in the same direction. This causes no backflow of the liquids, and thus, the washing step can be efficiently performed.

In the example shown in FIG. 50, the linear portion 143 has a flow path width W3 which is greater than a flow path width W2 of the connection portion 142a for causing a liquid to flow in. Accordingly, the linear portion 143 can have a wide shape that allows the magnetic particles to be sufficiently brought into contact with the washing liquid. As a result, the washing efficiency can be increased.

Figure 51:
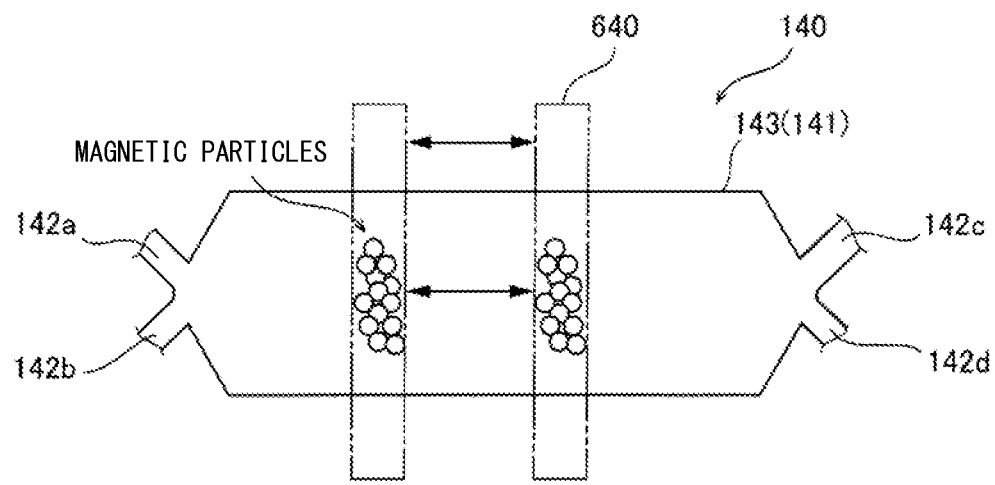
FIG. 51 shows an operation example of washing/concentrating magnetic particles in the fourth flow path.

FIG. 51 shows an example of operation of washing/concentrating the magnetic particles in the fourth flow path 140. The liquid containing the magnetic particles flows from the connection portion 142a into the channel 141. The magnetic particles in the liquid are concentrated by the magnetic force of the magnet 640. The magnet 640 can reciprocate in the longitudinal direction of the linear portion 143. The magnetic particles follow the reciprocating movement of the magnet 640, and are gathered while reciprocating in the linear portion 143.

The washing liquid is supplied from the connection portion 142b. The washing liquid flows in from the connection portion 142b, passes through the linear portion 143, and continuously flows toward the connection portion 142d. The connection portion 142d functions as a drain for discharging the washing liquid. The magnetic particles in the flow of the washing liquid reciprocate in the linear portion 143 by following the operation of the magnet 640, whereby the washing process is performed. By the magnetic particles following the operation of the magnet 640 and thus reciprocating in the linear portion 143, the magnetic particle can be inhibited from sticking together and aggregating.

In the primary washing step, a washing liquid containing alcohol is used. Through the primary washing using the washing liquid, an oil film on each magnetic particle is removed, and the amplified double-stranded DNA is denatured into single strands. The washed/concentrated magnetic particles are discharged from the connection portion 142c, to be transferred to the adjacent fifth flow path 150.

<Fifth Flow Path>

Figure 52:
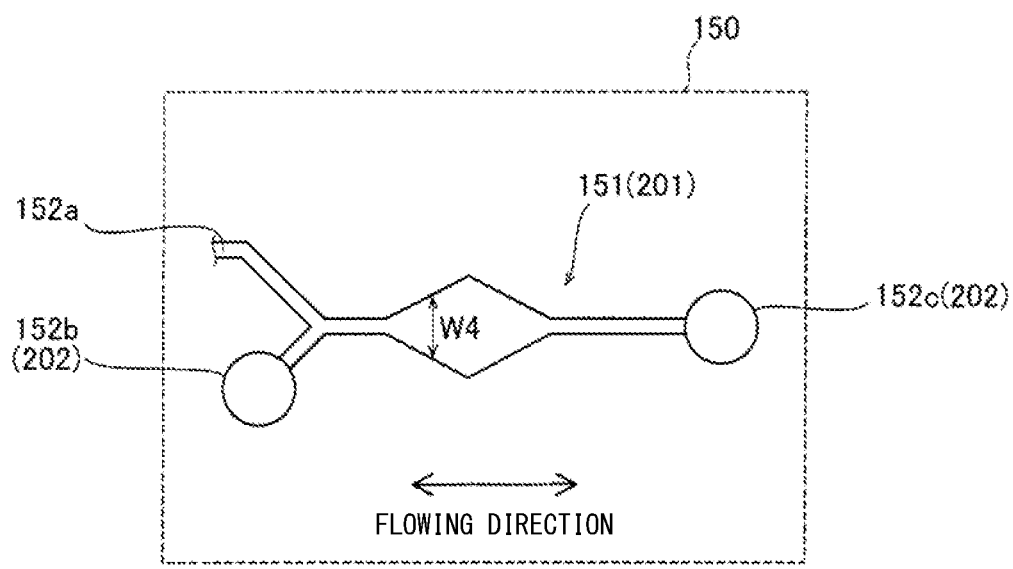
FIG. 52 shows a configuration example of a fifth flow path.

FIG. 52 shows a configuration example of the fifth flow path 150 to be used in the hybridization step. In the fifth flow path 150, the magnetic particles are mixed with a reagent containing a labeled substance, and then are subjected to thermal cycles. The fifth flow path 150 can have a configuration similar to that of the first flow path 160 shown in FIG. 33. That is, the fifth flow path 150 includes: connection portions 152a and 152b on one side for causing liquids to flow in; a connection portion 152c on the other side for causing liquid to flow out; and a channel 151 connecting the connection portions 152a and 152b on the flow-in side and the connection portion 152c on the flow-out side.

In the configuration example shown in FIG. 52, the liquid containing the magnetic particles is transferred from the connection portion 152a, and the reagent containing the labeled substance 17 is infused from the connection portion 152b, for example. Through the thermal cycles, DNA on the magnetic particles and the labeled substance 17 are bound together.

In the configuration example shown in FIG. 52, a flow path width W4 of the channel 151 of the fifth flow path 150 varies along the flowing direction of the liquid. That is, the width gradually increases from the upstream side of the channel 151 along the flowing direction, and then, is gradually reduced from the substantially center position toward the downstream side of the channel 151. In the example shown in FIG. 52, the channel 151 has a rhombic shape. By causing the flow path width W4 to be varied along the flowing direction, it is possible to control the flow rate of the liquid inside the channel 151. As a result, the flow rate can be controlled to a flow rate that is different from the flow rates in other flow paths and that is appropriate for binding the labeled substance 17 to the amplification product of the nucleic acid 10.

The secondary washing step after the hybridization (binding) between the amplification product of the nucleic acid 10 and the labeled substance 17 may be performed in the fifth flow path 150. For example, in FIG. 52, in a state where the magnetic particles are collected in the channel 151 by the magnet 640 (see FIG. 51), a washing liquid is infused from the connection portion 152b. In the secondary washing step, PBS is used as the washing liquid. Through the secondary washing using the washing liquid, unreacted labeled substance 17 that did not bind to DNA (including the labeled substance non-specifically attached to magnetic particles) is removed. In this case, as in the case of the fourth flow path 140 (see FIG. 50), it is preferable to provide the fifth flow path 150 with a connection portion 152 on the discharge side for draining. The magnetic particles including the labeled substance 17 after the secondary washing are discharged from the connection portion 152c.

On the downstream side of the fifth flow path 150 for performing hybridization, the fourth flow path 140 for performing the secondary washing may be added.

<Modification of Flow Path Configuration>

As another configuration example, it may be configured such that the primary washing, the hybridization, and the secondary washing are performed in a single fourth flow path 140 (see FIG. 51). In this case, the specimen after the emulsion breaking is introduced from the connection portion 142a into the channel 141, and the magnetic particles are collected by the magnet 640. The washing liquid containing alcohol for the primary washing, the labeled reagent for the hybridization, and the washing liquid (PBS) for the secondary washing are sequentially infused from the connection portion 142b, and then the respective step processes are performed. In this case, there is no need to provide the fifth flow path 150 on the downstream side of the fourth flow path 140.

(Description of Detection Step)

The magnetic particles including the labeled substance 17 after the secondary washing are detected by means of a flow cytometer and image analysis, for example. For detection by the flow cytometer, the magnetic particles including the labeled substance 17 are collected from the sample processing apparatus 500, and then transferred to a detection unit 550 or a flow cytometer provided outside the apparatus, for example. With respect to the magnetic particles including the labeled substance 17, fluorescence and the like based on labeling are detected by the detection unit 544 of the sample processing apparatus 500. Images of the magnetic particles including the labeled substance 17 are taken by the camera unit 545 of the sample processing apparatus 500, and the taken images are analyzed by the sample processing apparatus 500 or a computer connected to the sample processing apparatus 500.

It should be noted that the embodiments disclosed herein are merely illustrative in all aspects and should not be considered as restrictive. The scope of the present disclosure is defined not by the description of the above embodiments but by the scope of the claims, and includes meaning equivalent to the scope of the claims and all changes (modifications) within the scope.

What is claimed is:

1. A sample processing method for processing a target component in a sample by use of a sample processing chip having a storage portion and a droplet forming flow path, the sample processing method comprising:
   storing, in the storage portion, a mixture of the target component and a predetermined amount of a diluent for causing the target component to be encapsulated by one molecule or by one particle into a droplet;
   heating the mixture in the storage portion to cause thermal convection in the storage portion thereby to mix the target component and the diluent together; and
   in the droplet forming flow path, forming droplets in a dispersion medium, each droplet containing the diluted target component and a reagent that reacts with the target component.

2. The sample processing method of claim 1, wherein
   in a state where either a longitudinal direction or a short direction in a main flat face of the sample processing chip having a flat plate shape is aligned with the gravity direction, the mixture in the storage portion is heated to cause thermal convection in the storage portion.

3. The sample processing method of claim 2, wherein
   the mixture in a lower portion in the gravity direction of the storage portion is heated to form temperature distribution for causing thermal convection in the storage portion.

4. The sample processing method of claim 2, wherein
   in a state where either the longitudinal direction or the short direction in the main flat face of the sample processing chip having the flat plate shape is aligned with the gravity direction, if a direction along the gravity direction is set as a vertical direction of the storage portion and a direction along either the other of the longitudinal direction or the short direction is set as a horizontal direction of the storage portion,
   into the storage portion, the mixture is stored by a predetermined amount that realizes an aspect ratio of a length in the vertical direction by which the mixture occupies the storage portion to a length in the horizontal direction by which the mixture occupies the storage portion is not less than 0.1 and not greater than 10.

5. The sample processing method of claim 1, wherein the mixture is heated to a temperature of not less than 50° C. and not higher than 85° C. to cause thermal convection in the storage portion.

6. The sample processing method of claim 1, wherein the mixture is heated for a predetermined time of less than 10 minutes, thereby to complete mixing of the target component and the diluent together.

7. A sample processing chip to be set in a sample processing apparatus and configured to process a target component in a sample supplied by the sample processing apparatus, the sample processing chip comprising:
a dilution flow path including a storage portion in which to store a mixture of the target component and a predetermined amount of a diluent configured to cause the target component to be encapsulated by one molecule or by one particle into a droplet, the dilution flow path configured to mix the target component and the diluent together, by causing thermal convection in the storage portion by heat generated by a heating portion disposed in the sample processing apparatus; and
a droplet forming flow path configured to form droplets in a dispersion medium, each droplet containing the target component diluted in the dilution flow path and a reagent that reacts with the target component.

8. The sample processing chip of claim 7, comprising:
a plurality of fluid modules in which the dilution flow path and the droplet forming flow path are formed, respectively;
a base plate on which the plurality of fluid modules are disposed; and
a connection flow path configured to connect the fluid modules disposed on the base plate, and configured to move the target component from the dilution flow path to the droplet forming flow path.

9. The sample processing chip of claim 8, wherein the base plate has a thickness of not less than 0.1 mm and not greater than 5 mm.

10. The sample processing chip of claim 7, comprising a plurality of the dilution flow paths connected to each other in series, wherein
of the mixture of the target component and the diluent diluted in dilution flow path in a former stage, a predetermined amount of the mixture is supplied to the dilution flow path in a latter stage.

11. The sample processing chip of claim 10, wherein in the plurality of the dilution flow paths, as a whole, the target component is diluted at a dilution rate obtained by multiplying dilution rates of the individual dilution flow paths.

12. The sample processing chip of claim 10, wherein in the plurality of the dilution flow paths, as a whole, the target component is diluted at a dilution rate of not less than $10^3$ fold and not greater than $10^7$ fold.

13. The sample processing chip of claim 7, wherein in the dilution flow path, the target component is diluted at a dilution rate of not less than 25 fold and not greater than 1500 fold.

14. The sample processing chip of claim 8, wherein the dilution flow path is formed so as to extend along a main surface of the base plate, and includes a first flow path configured to supply liquid to the storage portion, and
the storage portion has a shape in which, in a direction along the main surface, a flow path width of the storage portion is increased relative to a flow path width of the first flow path.

15. The sample processing chip of claim 14, wherein the storage portion has a shape in which an aspect ratio of a first length of the storage portion along a longitudinal direction of the main surface to a second length of the storage portion along a short direction of the main surface is not less than 0.1 and not greater than 10.

16. The sample processing chip of claim 7, wherein the dilution flow path further includes a second flow path configured to send out liquid in the storage portion to the droplet forming flow path, and
the second flow path has a flow path width smaller than a maximum flow path width of the storage portion.

17. The sample processing chip of claim 7, wherein the droplet forming flow path includes:
a first channel in which the mixture of the target component and the reagent flows;
a second channel in which the dispersion medium non-miscible with the mixture flows; and
a crossing part at which the first channel and the second channel cross each other.

18. The sample processing chip of claim 7, wherein the dilution flow path is formed from a cycloolefin polymer or a cycloolefin copolymer.

19. The sample processing chip of claim 8, wherein the dilution flow path and the droplet forming flow path are respectively provided in the fluid modules formed from materials different from each other.

20. A sample processing apparatus configured to process a target component in a sample by use of the sample processing chip of claim 7, the sample processing apparatus comprising:
a setting portion in which to set the sample processing chip;
a liquid sending portion configured to supply to the sample processing chip a liquid containing the target component and a diluent for diluting the target component, and transfer the liquid and the diluent; and
a heating portion configured to heat a mixture of the diluent and the target component supplied to the storage portion in the sample processing chip, to cause thermal convection in the storage portion.

\* \* \* \* \*